(12) United States Patent
Glossop

(10) Patent No.: US 12,350,348 B2
(45) Date of Patent: Jul. 8, 2025

(54) COMPOUNDS AND THERAPEUTIC USES THEREOF

(71) Applicant: AVVINITY THERAPEUTICS LIMITED (GB/GB), London (GB)

(72) Inventor: Melanie Glossop, Sandwich (GB)

(73) Assignee: AVVINITY THERAPEUTICS LIMITED (GB/GB), London (GB)

( * ) Notice: Subject to any disclaimer, the term of this patent is extended or adjusted under 35 U.S.C. 154(b) by 1091 days.

(21) Appl. No.: 17/284,379

(22) PCT Filed: Oct. 10, 2019

(86) PCT No.: PCT/GB2019/052886
§ 371 (c)(1),
(2) Date: Apr. 9, 2021

(87) PCT Pub. No.: WO2020/074909
PCT Pub. Date: Apr. 16, 2020

(65) Prior Publication Data
US 2021/0346514 A1 Nov. 11, 2021

(30) Foreign Application Priority Data

Oct. 10, 2018 (GB) .................................... 1816553

(51) Int. Cl.
| | | |
|---|---|---|
| C07K 16/28 | (2006.01) | |
| A61K 47/54 | (2017.01) | |
| A61K 47/68 | (2017.01) | |
| C07K 16/30 | (2006.01) | |
| C07K 17/10 | (2006.01) | |

(52) U.S. Cl.
CPC ........ *A61K 47/6889* (2017.08); *A61K 47/549* (2017.08); *A61K 47/6803* (2017.08); *A61K 47/6807* (2017.08); *A61K 47/6851* (2017.08); *C07K 16/28* (2013.01); *C07K 16/2863* (2013.01); *C07K 16/2887* (2013.01); *C07K 16/30* (2013.01); *C07K 17/10* (2013.01); *C07K 2317/24* (2013.01); *C07K 2317/55* (2013.01); *C07K 2317/56* (2013.01)

(58) Field of Classification Search
CPC ................ C07K 16/28; C07K 16/2887; C07K 16/2863; C07K 17/10; C07K 2317/24; C07K 2317/55; C07K 2317/56; A61K 47/549; A61K 47/6801; A61K 47/6803; A61K 47/6851; A61K 47/6889; A61K 47/6807
See application file for complete search history.

(56) References Cited

U.S. PATENT DOCUMENTS

| | | | | |
|---|---|---|---|---|
| 2009/0060930 A1* | 3/2009 | Mautino | ............ | A61K 39/0011 424/277.1 |
| 2013/0149331 A1 | 6/2013 | Wang et al. | | |
| 2014/0112975 A1* | 4/2014 | Kiessling | ............. | A61K 47/543 424/130.1 |
| 2016/0256388 A1* | 9/2016 | Galili | .................... | A61K 38/177 |
| 2021/0198381 A1* | 7/2021 | Wu | .................... | A61K 47/6851 |

FOREIGN PATENT DOCUMENTS

| | | |
|---|---|---|
| WO | 2007146847 A2 | 12/2007 |
| WO | 2008057235 A2 | 5/2008 |
| WO | 2014151423 A1 | 9/2014 |
| WO | 2016196682 A1 | 12/2016 |
| WO | 2018185495 A1 | 10/2018 |
| WO | WO-2018187636 A1 * | 10/2018 |
| WO | 2018203087 A1 | 11/2018 |

OTHER PUBLICATIONS

Bhattacharya et al. Impact of genetic variation on three dimensional structure and function of proteins. PLoS One 12(3): e0171355, 2017.*
Bork, P. Powers and pitfalls in sequence analysis: the 70% hurdle. Genome Res 10: 398-400, 2000.*
Bork, P. Go hunting in sequence databases but watch out for the traps. Trends in Genetics 12(10): 425-427, 1996.*
Brenner. S.E. Errors in genome annotation. Trends in Genetics 15:132-133, 1999.*
Brorson et al. Mutational analysis of avidity and fine specificity of anti-levan antibodies. J Immunol 163: 6694-6701, 1999.*
Brummell et al. Probing the combining site of an anti-carbohydrate antibody by saturation-mutagenesis: role of the heavy-chain CDR3 residues. Biochem 32(4): 1180-1187, 1993.*
Burks et al. In vitro scanning saturation mutagenesis of an antibody binding pocket. Proc Natl Acad Sci USA 94(2): 412-417, 1997.*
Cassett et al. A peptide mimetic of an anti-CD4 monoclonal antibody by rationale design. Biochem Biophys Res Comm 307: 198-205, 2003.*
Chen et al. Selection and analysis of an optimized anti-VEGF antibody: crystal structure of an affinity-matured Fab in complex with antigen. J Mol Biol 293: 865-881, 1999.*
Colman, P.M. Effects of amino acid sequence changes on antibody-antigen interactions. Research in Immunol. 145:33-36, 1994.*
De Pascalis et al. Grafting and "abbreviated" complementarity-determining regions containing specificity-determining residues essential for ligand contact to engineer a less immunogenic humanized monoclonal antibody. J Immunol 169: 3076-3084, 2002.*
Doerks et al. Protein annotation: detective work for function prediction. Trends in Genetics 14:248-250, 1998.*
Fenton et al. Rheostat positions: a new classification of protein positions relevant to pharmacogenomics. Medicinal Chem Res 29: 1133-1146, 2020.*
Guo et al. Protein tolerance to random amino acid change. Proc Natl Acad Sci USA 101(25): 9205-9210, 2004.*
Holm et al. Functional mapping and single chain construction of the anti-cytokeratin 8 monoclonal antibody TS1. Mol Immunol 44: 1075-1084, 2007.*

(Continued)

*Primary Examiner* — Bridget E Bunner

(57) ABSTRACT

The invention relates to novel compounds with the ability to link an immune response to a defined therapeutic target, to the use of the compounds in treating cancer and infectious diseases, to compositions containing the compounds, processes for their preparation and to novel intermediates used in the process.

21 Claims, 31 Drawing Sheets

Specification includes a Sequence Listing.

(56) References Cited

OTHER PUBLICATIONS

Jang et al. The structural basis for DNA binding by an anti-DNA autobody. Mol Immunol 35: 1207-1217, 1998.*
Kobayashi et al. Tryptophan H33 plays an important role in pyrimidine (6-4) pyrimidone photoproduct binding by a high affinity antibody. Protein Engineer 12(10): 879-884, 1999.*
MacCallum et al. Antibody-antigen interactions: contact analysis and binding site topography. J Mol Biol 262: 732-745, 1996.*
Paul, William E., Fundamental Immunology, 3rd Edition, Raven Press, New York, Chapt. 8, pp. 292-295 (1993).*
Rudikoff et al. Single amino acid substitution altering antigen-binding specificity. Proc Natl Acad Sci USA 79: 1979-1983, 1982.*
Sela-Culang et al. The structural basis of antibody-antigen recognition. Front Immunol 4: 302, 2013 (13 total pages).*
Skolnick et al. From genes to protein structure and function: novel applications of computational approaches in the genomic era. Trends Biotechnol 18(1):34-39 2000.*
Smith et al. The challenges of genome sequence annotation or "the devil is in the details". Nature Biotechnol 15: 1222-1223, 1997.*
Tokuriki et al. Stability effects of mutations and protein evolvability. Curr Opin Structural Biol 19: 596-604, 2009.*
Vajdos et al. Comprehensive functional maps of the antigen-binding site of an anti-ErbB2 antibody obtained with shotgun scanning mutagenesis. J Mol Biol 320: 415-428, 2002.*
Vasudevan et al. A single amino acid change in the binding pocket alters specificity of an anti-integrin antibody AP7.4 as revealed by its crystal structure. Blood Cells Mol Diseases 32: 176-181, 2004.*
Wu et al. Humanization of a murine monoclonal antibody by simultaneous optimization of framework and CDR residues. J Mol Biol. 294: 151-162, 1999.*
Zhang et al. Comprehensive optimization of a single-chain variable domain antibody fragment as a targeting ligand for a cytotoxic nanoparticle. mAbs 7(1): 42-52, 2015.*
Carlson et al. Selective Tumor Cell Targeting Using Low-Affinity, Multivalent Interactions. ACS Chem Biol 2(2): 119-127, 2007.*
Naicker et al. Design and synthesis of aGal-conjugated peptide T20 as novel antiviral agent for HIV-immunotargeting. Org Biomol Chem 2: 660-664, 2004.*
Owen et al. Bifunctional Ligands that Target Cells Displaying the avb3 Integrin. ChemBioChem 8: 68-82, 2007.*
Perdomo et al. Neutralization of HIV-1 by redirection of natural antibodies. Proc Natl Acad Sci 105(34): 12515-12520, 2008.*
Wenlan Chen et al: "–Rhamnose Antigen: A Promising Alternative to [alpha]-Gal for Cancer Immunotherapies", ACS Chemical Biology, vol. 6, No. 2, Feb. 18, 2011, pp. 185-191, XP55043321, ISSN: 1554-8929, DOI: 10.1021/cb100318z.

* cited by examiner

SEQUENCE LISTING

<160> NUMBER OF SEQ ID NOS: 6

<210> SEQ ID NO 1
<211> LENGTH: 449
<212> TYPE: PRT
<213> ORGANISM: Artificial
<220> FEATURE:
<223> OTHER INFORMATION: Monoclonal Antibody

<400> SEQUENCE: 1

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
        260                 265                 270

Pro Glu Val Lys Phe Asn Trp Tyr Val Asp Gly Val Glu Val His Asn
    275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 2
<211> LENGTH: 214
<212> TYPE: PRT
<213> ORGANISM: Artificial
<220> FEATURE:
<223> OTHER INFORMATION: Monoclonal Antibody

<400> SEQUENCE: 2

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
                20                  25                  30

Ile His Trp Tyr Gln Gln Arg Thr Asn Gly Ser Pro Arg Leu Leu Ile
            35                  40                  45

Lys Tyr Ala Ser Glu Ser Ile Ser Gly Ile Pro Ser Arg Phe Ser Gly
        50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

```
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210
```

<210> SEQ ID NO 3
<211> LENGTH: 451
<212> TYPE: PRT
<213> ORGANISM: Artificial
<220> FEATURE:
<223> OTHER INFORMATION: Monoclonal Antibody

<400> SEQUENCE: 3

```
Gln Val Gln Leu Gln Gln Pro Gly Ala Glu Leu Val Lys Pro Gly Ala
1               5                   10                  15
Ser Val Lys Met Ser Cys Lys Ala Ser Gly Tyr Thr Phe Thr Ser Tyr
            20                  25                  30
Asn Met His Trp Val Lys Gln Thr Pro Gly Arg Gly Leu Glu Trp Ile
        35                  40                  45
Gly Ala Ile Tyr Pro Gly Asn Gly Asp Thr Ser Tyr Asn Gln Lys Phe
    50                  55                  60
Lys Gly Lys Ala Thr Leu Thr Ala Asp Lys Ser Ser Ser Thr Ala Tyr
65                  70                  75                  80
Met Gln Leu Ser Ser Leu Thr Ser Glu Asp Ser Ala Val Tyr Tyr Cys
                85                  90                  95
Ala Arg Ser Thr Tyr Tyr Gly Gly Asp Trp Tyr Phe Asn Val Trp Gly
            100                 105                 110
Ala Gly Thr Thr Val Thr Val Ser Ala Ala Ser Thr Lys Gly Pro Ser
        115                 120                 125
Val Phe Pro Leu Ala Pro Ser Ser Lys Ser Thr Ser Gly Gly Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Lys Ala Glu Pro Lys Ser Cys
    210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
```

-continued

```
Glu Asp Pro Glu Val Lys Phe Asn Trp Tyr Val Asp Gly Val Glu Val
            275                 280                 285

His Asn Ala Lys Thr Lys Pro Arg Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
    450
```

<210> SEQ ID NO 4
<211> LENGTH: 213
<212> TYPE: PRT
<213> ORGANISM: Artificial
<220> FEATURE:
<223> OTHER INFORMATION: Monoclonal Antibody

<400> SEQUENCE: 4

```
Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175
```

```
Thr Leu Thr Leu Ser Lys Ala Asp Tyr Glu Lys His Lys Val Tyr Ala
            180                 185                 190
Cys Glu Val Thr His Gln Gly Leu Ser Ser Pro Val Thr Lys Ser Phe
        195                 200                 205
Asn Arg Gly Glu Cys
    210
```

<210> SEQ ID NO 5
<211> LENGTH: 449
<212> TYPE: PRT
<213> ORGANISM: Artificial
<220> FEATURE:
<223> OTHER INFORMATION: Monoclonal Antibody

<400> SEQUENCE: 5

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Asn Ile Lys Asp Thr
            20                  25                  30
Tyr Ile His Trp Val Arg Gln Ala Pro Gly Lys Gly Leu Glu Trp Val
        35                  40                  45
Ala Arg Ile Tyr Pro Thr Asn Gly Tyr Thr Arg Tyr Ala Asp Ser Val
    50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ser Arg Trp Gly Gly Asp Gly Phe Tyr Ala Met Asp Tyr Trp Gly Gln
            100                 105                 110
Gly Thr Leu Val Thr Val Ser Ser Ala Ser Thr Lys Gly Pro Ser Val
        115                 120                 125
Phe Pro Leu Ala Pro Ser Ser Lys Ser Thr Ser Gly Gly Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
```

```
Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
                435                 440                 445

Gly

<210> SEQ ID NO 6
<211> LENGTH: 214
<212> TYPE: PRT
<213> ORGANISM: Artificial
<220> FEATURE:
<223> OTHER INFORMATION: Monoclonal Antibody

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

COMPOUNDS AND THERAPEUTIC USES THEREOF

CROSS-REFERENCE TO RELATED APPLICATIONS

The present application is a U.S. National Stage entry under 35 U.S.C. § 371 of International Application No. PCT/GB2019/052886 filed on Oct. 10, 2019, designating the United States of America and published in English on Apr. 16, 2020, which claims priority to GB Application No. 1816553.0 filed Oct. 10, 2018, each of which is hereby incorporated by reference in its entirety.

FIELD OF THE INVENTION

The invention relates to novel compounds with the ability to link an immune response to a defined therapeutic target, to the use of said compounds in treating cancer and infectious diseases, to compositions containing said compounds, processes for their preparation and to novel intermediates used in said process.

BACKGROUND OF THE INVENTION

There is a need to find novel ways to recruit an individual's immune system to fight disease. The human immune system continually surveys the body seeking foreign signals to identify potentially harmful pathogens or mutated human cells (that could become a cause of cancerous growth) and targets them for elimination. Natural antibodies exist that can be recruited to said pathogens or mutated human cells to drive the immune system to eliminate the threat.

Cancer is a group of diseases involving abnormal cell growth with the potential to invade or spread to other parts of the body. In 2012, cancer occurred in about 14.1 million people. It caused about 8.2 million deaths or 14.6% of all human deaths. The most common types of cancer in males are lung cancer, prostate cancer, colorectal cancer and stomach cancer. In females the most common types are breast cancer, colorectal cancer, lung cancer, and cervical cancer. It is well established that the immune response plays a vital role in the identification and elimination of cancerous cells. Drugs exist that fight cancer by boosting an individual's immune system to help fight the cancer. There is a need to be able to better target the immune response specifically to the cancer cell and to generate a broader range of the patient's own tumour associated antigens. Targeting pre-existing natural antibodies to the patient's own tumour could meet this need. There is an urgent need to identify novel ways of treating bacterial, viral and fungal infections. Antimicrobial drug resistance is becoming a major global health threat. For example, it is estimated that more than 2 million people in the US are infected with bacteria resistant to one class of antibiotics every year (Centers for Disease Control and Prevention, 2013).

An innovative approach to the treatment of infectious disease or cancer was disclosed in WO 2005/079423 which describes an immunity linker which contains two binding moieties. The first binding moiety is capable of binding to an immune response component of an individual. The second binding moiety is capable of binding to any compound or foreign material such as antigens, pathogens, chemicals, or endogenous materials such as altered cells found in cancer. The resultant effect of said immunity linker molecule is that the pre-existing immune response of the individual is diverted towards the target, i.e. the cancer cell or specific pathogen. Examples of said first binding moieties include compounds or agents which are recognised by the immune system of said individual as foreign and which would therefore trigger an immune response.

Typical examples of first binding moieties include the small molecule hapten dinitrophenyl (DNP), alpha-Gal or β-1,6-glucan. Another such example is a carbohydrate molecule capable of binding to human serum antibodies such as anti-Rhamnose (i.e. L-Rhamnose) resulting in target cell destruction (Kiessling et al (2014) ChemBioChem 15 (10), 1393-1398; US 2014/0112975; Li et al (2016) ACS Chem. Biology 11 (5), 1205-1209), Wall et al (2018) ACS Chem. Biology (13) 2130-2142.

The α-Gal epitope (Galα1,3Galα1,4GlcNAc-R) is a unique carbohydrate, naturally produced on glycolipids and glycoproteins to display multiple epitopes on branched oligosaccharides (J.Immunology (2007), 178 (7), 4676-87). The alpha-Gal epitope is synthesised, for example, by the transferase alpha1-, 3-GT, an enzyme well known to catalyse the synthesis of Galα-1,3-Gal on multiple glycosylation sites (WO 98/34957). Although this method is efficient, the synthesis is reliant on existing or engineered glycosylation sites, and only enables one alpha-Gal unit per conjugation site.

There is therefore an attractive need for a suitable modular approach to either one or multi-presentation of alpha-Gal trisaccharide or rhamnose units to optimally harness the natural immune system.

One strategy for selectively directing the immune system is to employ and exploit multivalent recognition of haptens on a cell surface (Kiessling et al ACS Chem Biol. (2007) 119-127), as stable and long-lived complexes of antibodies increase the productivity of the immune response. Therefore, there is a need for potent cell-targeting agents (second binding moieties) that simultaneously present multivalent haptens by exploiting the numerous amino acid conjugation sites present on a peptide scaffold for selectively destroying unwanted cells.

US 2013/0149331 describes immunogenic compositions comprising a T-cell antigen in association with a rhamnose monosaccharide and/or Forssman disaccharide.

Examples of said second binding moieties include antibodies or fragments thereof that bind to a specific target molecule and present opportunity for inherent multivalency. Further examples of said second binding moieties include established therapeutic antibodies or functional fragments thereof. Cells or pathogens targeted in this manner can be recognised by the immune system as foreign and marked for destruction. Thus, natural antibodies can be mobilised to these tumour cells or pathogens and harness the immune system to eliminate the threat.

SUMMARY OF THE INVENTION

According to a first aspect of the invention, there is provided a compound of formula (I) or a pharmaceutically acceptable salt thereof:

$$[F—S_1—X]_2\text{-}L \qquad (I)$$

wherein:
F represents rhamnose or a carbohydrate molecule capable of binding to a human anti-alpha-galactosyl antibody;
$S_1$ represents a spacer selected from a $—(CH_2)_a—$ or $—(CH_2)_b—(CH_2—CH_2—O)_c—(CH_2)_d—$ group, wherein one to ten of said $—CH_2—$ groups may optionally be substituted by one or more groups selected from —O—, —S—, =N(H)—, —C(=O)—, —C(O)NH—, —NHC(O)—;

a represents an integer selected from 1 to 35;
b represents an integer selected from 0 to 5;
c represents an integer selected from 1 to 20;
d represents an integer selected from 1 to 20;
X represents an antibody or antigen binding fragment attachment moiety;
z represents an integer selected from 1 to 50; and
L represents a binding moiety selected from an antibody or antigen binding fragment thereof.

BRIEF DESCRIPTION OF THE FIGURES

FIG. 1.

FIG. 2.

FIG. 3.

FIG. 4.

FIG. 5.

FIG. 6.

FIG. 7.

DETAILED DESCRIPTION OF THE INVENTION

Figure 1A:
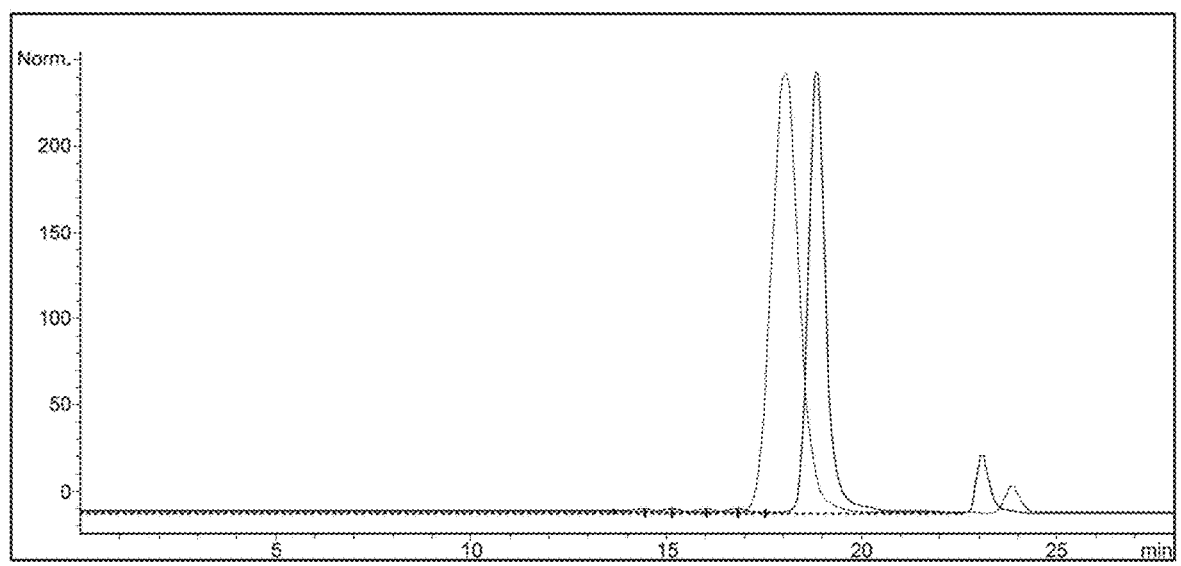
(FIG. 1A) SEC analysis of Example 1 (peak labelled "1") and Cetuximab-Fab (peak labelled "2")

According to a first aspect of the invention, there is provided a compound of formula (I) or a pharmaceutically acceptable salt thereof:

wherein:
F represents rhamnose or a carbohydrate molecule capable of binding to a human anti-alpha-galactosyl antibody;
$S_1$ represents a spacer selected from a —$(CH_2)_a$— or —$(CH_2)_b$—$(CH_2$—$CH_2$—$O)_c$—$(CH_2)_d$— group, wherein one to ten of said-$CH_2$-groups may optionally be substituted by one or more groups selected from —O—, —S—, =N(H)—, —C(=O)—, —C(O)NH— and —NHC(O)—;
a represents an integer selected from 1 to 35;
b represents an integer selected from 0 to 10;
c represents an integer selected from 1 to 20;
d represents an integer selected from 1 to 20;
X represents an antibody or antigen binding fragment attachment moiety;
z represents an integer selected from 1 to 50; and
L represents a binding moiety selected from an antibody or antigen binding fragment thereof.

The invention includes the description and use of novel immunoconjugate linkers that enable capability to display one or multiple epitopes of carbohydrates in addition to conjugation to single or multiple sites on a chosen antibody or fragment thereof, thus enabling the optimal recruitment of natural antibodies concomitant with retaining target binding efficacy. The invention provides for one skilled in the art to fine tune the optimal number of carbohydrates per chosen antibody or fragment thereof for optimal anti-rhamnose recruitment and retain target efficacy.

Monoclonal antibodies have greatly improved the outcome of patients suffering from cancer however certain patient populations demonstrate intrinsic resistance to these therapies and, while good outcomes can be observed, these may be short-lived and acquired resistance to mAb therapy remains an issue and increased antibody efficacy is desirable. Tumours can demonstrate or evolve mechanisms resulting in resistance or reduced response to antibody treatment such as through increased receptor expression or changes to the signalling pathway or reduced immune response (Reslan, L. Mabs 2009, 3, 222). For example, patients can show intrinsic resistance to cetuximab resulting from expression of the KRAS mutation which affects EGFR signalling (Lievre, A, J. Clin. Oncol. 2008, 26, 374). In addition, where patients initially respond well to cetuximab, the majority will eventually acquire resistance (Bianco, R. Endocr. Relat. Cancer 2005, S159; Brand, TM. Cancer Biol. Ther. 2011, 11, 777).

A further example of resistance to a therapeutic antibody is seen in the case of non-Hodgkin lymphoma patients treated with rituximab (an anti-CD20 monoclonal antibody). Resistance to Rituximab is observed in around half of treatment-naïve patients. Patients who show an initial response to rituximab therapy will frequently acquire resistance. Resistance mechanisms are complex and strategies to overcome resistance have shown limited success in patients (Best Pract. Res. Clin. Haematol. 2011, 203-216) thus there remains a compelling need to improve the activity of therapeutic antibodies to increase and prolong patient responses.

Many approaches have been adopted to improve upon the efficacy of therapeutic antibodies including antibody drug conjugates (ADCs), antibody toxin conjugates (immunotoxins) and engineered antibodies with enhanced effector mechanisms e.g. increased antibody dependent cellular cytotoxicity (ADCC). Despite these efforts, few therapies have achieved clinical success with side effects such as toxicity remaining a key issue (Beck, A. Nat. Rev. Drug. Discov. 2017), Thus there is a need for new strategies to modify mAbs to enhance efficacy, to improve patient outcomes.

Monoclonal antibody fragments such as Fab, Fab', Fab'2, $Fab_2$, $Fab_3$, $F(ab)_2$, Fv, scFv, diabody, triabody, tetrabody, nanobody are also known in the field of oncology. A number of advantages over full length mAbs have been reported; including increased tumour penetration resulting from their smaller size, easier production (they can be expressed in *E. coli* or yeast resulting in increased convenience and more efficient scale up) and reduced immunogenicity. Fragments such as scFvs or Fab fragments can however suffer from reduced efficacy when compared to full length mAbs. For example, the lack of an Fc domain on a Fab fragment eliminates the potential for ADCC driven efficacy, often a component of the anti-tumour response (Nelson, A. L. mAbs 2009, 2, 77).

In one embodiment, L represents a single domain antibody (sdAb). Such a single domain antibody (sdAb) is also known as a nanobody and typically comprises an antibody fragment consisting of a single monomeric variable antibody domain.

Thus the benefits of antibody fragments are often offset by the loss of function associated with them. The compounds of the present invention utilise the multiple lysine and cysteine conjugation sites accessible on a mAb or Fab. The protein scaffold acts as a skeleton for optimal hapten display, as such multiple loading may be beneficial to both antibody recruitment and target binding.

For both mAbs and their fragments, controlled, site specific conjugation is well known in the art e.g. through the incorporation of additional cysteine residues. Such an approach offers several advantages, in particular by allowing derivatisation of the mAb or fragment without disruption of the target binding epitopes and by enabling the loading to be controlled i.e. a fixed stoichiometry is achieved (Shen, B. Q. Nat. Biotechnol. 2012, 30, 184). One limitation of site specific conjugation is that a low loading of the conjugated moiety may result which can limit efficacy.

Linker Definitions

In one embodiment, $S_1$ represents a spacer selected from:
—$(CH_2)_a$— wherein one of said —$CH_2$— groups may optionally be substituted by one or more groups selected from —O—, —S—, =N(H)—, —C(=O)—, —C(O)NH— and —NHC(O)— (such as —$(CH_2)_8$—CO—); or
—$(CH_2)_b$—$(CH_2$—$CH_2$—$O)_c$—$(CH_2)_d$—, wherein one to five of said —$CH_2$— groups may optionally be substituted by one or more groups selected from —O—, —S—, =N(H)—, —C(=O)—, —C(O)NH— and —NHC(O)— (such as —$(CH_2)_2$—O—$(CH_2)_2$—NHCO—$(CH_2CH_2O)_4$—$(CH_2)_2$—NHCO—$(CH_2)_3$—CO—).

In a further embodiment, $S_1$ represents a spacer selected from:
—$(CH_2)_a$— wherein one of said —$CH_2$— groups may optionally be substituted by one or more groups selected from —C(=O)— (such as —$(CH_2)_8$—CO—); or
—$(CH_2)_b$—$(CH_2$—$CH_2$—$O)_c$—$(CH_2)_d$—, wherein four of said —$CH_2$— groups may optionally be substituted by one or more groups selected from —O—, —C(=O)— and —NHC(O)— (such as —$(CH_2)_2$—O—$(CH_2)_2$—NHCO—$(CH_2CH_2O)_4$—$(CH_2)_2$—NHCO—$(CH_2)_3$—CO—).

It will be appreciated that a, b, c and d are selected to maintain a suitable linker length between groups F and L. Examples of suitable linker lengths between F and L range from about 5 Å to about 50 Å or more in length, about 6 Å to about 45 Å, about 7 Å to about 40 Å, about 8 Å to about 35 Å, about 9 Å to about 30 Å, about 10 Å to about 25 Å, about 11 Å to about 20 Å, about 12 Å to about 15 Å. Thus, in one embodiment, a, b, c and d represent a total integer of no more than 45, such as between 5 and 45, such as between 7 and 42, such as no more than 30, such as between 5 and 30, such as between 9 and 17.

In one embodiment, a represents an integer selected from 1 to 30. In a further embodiment, a represents an integer selected from 5 to 25. In a further embodiment, a represents an integer selected from 8 to 20. In a further embodiment, a represents an integer selected from 9 to 15. In a further embodiment, a represents an integer selected from 9.

In one embodiment, b represents an integer selected from 0 to 8. In a further embodiment, b represents an integer selected from 2 to 6. In one embodiment, b represents an integer selected from 6.

In one embodiment, c represents an integer selected from 1 to 10. In a further embodiment, c represents an integer selected from 1 to 5. In a further embodiment, c represents an integer selected from 4.

In one embodiment, d represents an integer selected from 1 to 15. In a further embodiment, d represents an integer selected from 1 to 10. In a further embodiment, d represents an integer selected from 2 to 8. In a further embodiment, d represents an integer selected from 7.

In a further embodiment, z represents an integer selected from 1 to 40. In a further embodiment, z represents an integer selected from 1 to 36. In a further embodiment, z represents an integer selected from 4 to 30 (such as 4.3, 7.2, 8.3, 12 and 12-18).

Alpha Gal

In one embodiment, F represents a carbohydrate molecule capable of binding to a human anti-alpha-galactosyl antibody. References herein to the term "carbohydrate molecule capable of binding to a human anti-alpha-galactosyl antibody" include sugar (i.e. carbohydrate) moieties capable of binding to an immune response component (i.e. an anti-alpha-galactosyl antibody) of said human and consequently eliciting an immune response in a human. In one embodiment, said anti-alpha-galactosyl antibody is an anti-alpha-galactosyl IgG antibody or an anti-alpha-galactosyl IgM antibody. Examples of such carbohydrate molecules include alpha-galactosyl compounds and modified derivatives thereof. Further examples of suitable carbohydrate molecules include the alpha-gal epitopes listed in US 2012/0003251 as being suitable for use in the selective targeting and killing of tumour cells, the epitopes of which are herein incorporated by reference. In one embodiment, F is selected from galactosyl-alpha-1,3-galactosyl-beta-1,4-N-acetylglucosamine, alpha1-3 galactobiose, alpha1-3-beta1-4-galactotriose or galilipentasaccharide.

In one particular embodiment, F has a structure as shown in one of the following formulae:

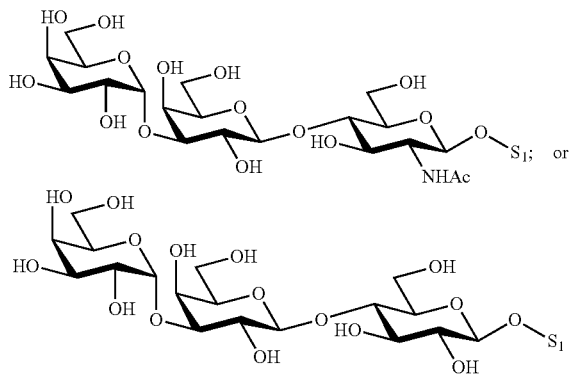

wherein $S_1$ refers to the point of attachment to the $S_1$ group.

In one particular embodiment, F has a structure as shown in the following formula:

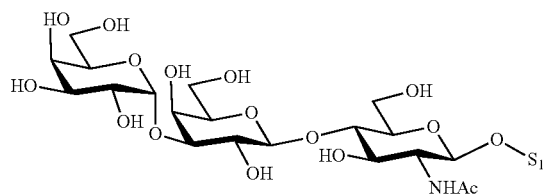

wherein $S_1$ refers to the point of attachment to the $S_1$ group.

Rhamnose

In one embodiment, F represents rhamnose. References herein to the term "rhamnose" include (2R,3R,4R,5R,6S)-6-Methyloxane-2,3,4,5-tetrol (also known as isodulcit, α-L-Rhamnose, L-Rhamnose, L-Mannomethylose, α-L-Rha, α-L-Rhamnoside, α-L-Mannomethylose, 6-Deoxy-L-mannose, Rhamnopyranose and Rhamnopyranoside). Rhamnose (Rha, Rham) is a naturally occurring deoxy sugar. It can be classified as either a methyl-pentose or a 6-deoxy-hexose. Rhamnose occurs in nature in its L-form as L-rhamnose (6-deoxy-L-mannose). In one embodiment, F is selected from L-rhamnose. L-rhamnose is an L-configured, deoxy-sugar monosaccharide capable of binding to and recruiting anti-L-Rha antibodies found in human sera.

In one particular embodiment, F has a structure as shown in one of the following formulae:

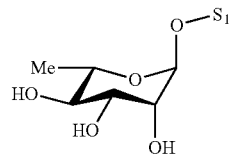

wherein $S_1$ refers to the point of attachment to the $S_1$ group.

Antibodies and Antigen Binding Fragments Thereof

References herein to the terms "antibody" or "antibodies" refer to molecules or active fragments of molecules that bind to known antigens, particularly to immunoglobulin molecules and to immunologically active portions of immunoglobulin molecules, i.e. molecules that contain a binding site that immunospecifically binds an antigen. The immunoglobulin according to the invention can be of any class (IgG, IgM, IgD, IgE, IgA and IgY) or subclass (e.g. IgG1, IgG2, IgG3, IgG4, IgA1 and IgA2) or subclasses (isotypes) of immunoglobulin molecule (e.g. IgG in IgG1, IgG2, IgG3, and IgG4, or IgA in IgA1 and IgA2).

Within the scope of the present invention the terms "antibody" or "antibodies" include monoclonal, polyclonal, chimeric, single chain, bispecific, human and humanized antibodies as well as active fragments thereof. Examples of active fragments of molecules that bind to known antigens include Fab, F(ab')2, scFv and Fv fragments, including the products of an Fab immunoglobulin expression library and epitope-binding fragments of any of the antibodies and fragments mentioned above.

As used herein, the term "monoclonal antibody" refers to an antibody that is mass produced in the laboratory from a single clone and that recognizes only one antigen. Monoclonal antibodies are typically made by fusing a normally short-lived, antibody-producing B cell to a fast-growing cell, such as a cancer cell (sometimes referred to as an "immortal" cell). The resulting hybrid cell, or hybridoma, multiplies rapidly, creating a clone that produces large quantities of the antibody. For the purpose of the present invention, "monoclonal antibody" is also to be understood to comprise antibodies that are produced by a mother clone which has not yet reached full monoclonality.

As used herein, the term "chimeric antibody" refers to a monoclonal antibody comprising a variable region, i.e., binding region, from mouse and at least a portion of a constant region derived from a different source or species, usually prepared by recombinant DNA techniques. Chimeric antibodies comprising a mouse variable region and a human constant region are exemplary embodiments. Such mouse/human chimeric antibodies are the product of expressed immunoglobulin genes comprising DNA segments encoding mouse immunoglobulin variable regions and DNA segments encoding human immunoglobulin constant regions. Other forms of "chimeric antibodies" encompassed by the present disclosure are those in which the class or subclass has been modified or changed from that of the original antibody. Such "chimeric" antibodies are also referred to as "class-switched antibodies." Methods for producing chimeric antibodies involve conventional recombinant DNA and gene transfection techniques now well known in the art. See, e.g., Morrison, S. L., et al., *Proc. Natl. Acad Sci. USA* 81 (1984) 6851-6855; U.S. Pat. Nos. 5,202,238 and 5,204,244.

As used herein the term "humanized antibody" or "humanized version of an antibody" refers to antibodies in which the framework or "complementarity determining regions" (CDR) have been modified to comprise the CDR of an immunoglobulin of different specificity as compared to that of the parent immunoglobulin. In some exemplary embodiments, the CDRs of the VH and VL are grafted into the framework region of human antibody to prepare the "humanized antibody." See e.g. Riechmann, L., et al., Nature 332 (1988) 323-327; and Neuberger, M. S., et al., Nature 314 (1985) 268-270. The heavy and light chain variable framework regions can be derived from the same or different human antibody sequences. The human antibody sequences can be the sequences of naturally occurring human antibodies. Human heavy and light chain variable framework regions are listed e.g. in Lefranc, M.-P., Current Protocols in Immunology (2000)—Appendix 1P A. 1P. 1-A. 1P. 37 and are accessible via IMGT, the international ImMunoGeneTics information System® (imgt.cines.fr) or via vbase.mrc-cpe.cam.ac.uk, for example. Optionally the framework region can be modified by further mutations. Exemplary CDRs correspond to those representing sequences recognizing the antigens noted above for chimeric antibodies. In some embodiments, such humanized version is chimerized with a human constant region. The term "humanized antibody" as used herein also comprises such antibodies which are modified in the constant region to generate the properties according to the disclosure, especially in regard to Clq binding and/or FcR binding, e.g. by "class switching" i.e. change or mutation of Fc parts (e.g. from lgG1 to lgG4 and/or lgG1/lgG4 mutation).

As used herein the term "human antibody" is intended to include antibodies having variable and constant regions derived from human germ line immunoglobulin sequences. Human antibodies are well-known in the state of the art (van Dijk, M. A., and van de Winkel, J. G., Curr. Opin. Chem. Biol. 5 (2001) 368-374). Human antibodies can also be produced in transgenic animals (e.g., mice) that are capable, upon immunization, of producing a full repertoire or a selection of human antibodies in the absence of endogenous immunoglobulin production. Transfer of the human germline immunoglobulin gene array in such germ-line mutant mice results in the production of human antibodies upon antigen challenge (see, e.g., Jakobovits, A., et al., Proc. Natl. Acad. Sci. USA 90 (1993) 2551-2555; Jakobovits, A., et al., Nature 362 (1993) 255-258; Brueggemann, M. D., et al., Year Immunol. 7 (1993) 33-40). Human antibodies can also be produced in phage display libraries (Hoogenboom, H. R., and Winter, G., J. Mol. Biol. 227 (1992) 381-388; Marks, J. D., et al., J. Mol. Biol. 222 (1991) 581-597). The techniques of Cole, A., et al. and Boerner, P., et al. are also available for the preparation of human monoclonal antibodies (Cole, A., et al., Monoclonal Antibodies and Cancer Therapy, Liss, A. R. (1985) p. 77; and Boerner, P., et al., J. Immunol. 147 (1991) 86-95). As already mentioned, according to the instant disclosure the term "human antibody" as used herein also comprises such antibodies which are modified in the constant region to generate the properties according to the disclosure, for example in regard to Clq binding and/or FcR binding, e.g. by "class switching" i.e. change or mutation of Fc parts (e.g. from lgG1 to lgG4 and/or lgG1/lgG4 mutation).

As used herein "single chain antibody" refers to single chain Fv molecules (scFv), wherein a VH domain and a VL domain are linked by a peptide linker which allows the two domains to associate to form an antigen binding site (Bird et al., 1988, Science 242:423-426, Huston et al., 1988, Proc. Natl. Acad. Sci. U.S.A. 85:5879-5883 or a bispecific single chain Fv (WO 03/11161).

As used herein the term "bispecific antibodies" refers to antibodies that bind to two (or more) different antigens.

As used herein the term "antibody fragments" refers to a portion of a full-length antibody, for example possibly a variable domain thereof, or at least an antigen binding site thereof.

Examples of antibody fragments include diabodies, single-chain antibody molecules, and multispecific antibodies formed from antibody fragments. scFv antibodies are, e.g., described in Huston, J. S., Methods in Enzymol. 203 (1991) 46-88. Antibody fragments can be derived from an antibody of the present invention by a number of art-known techniques. For example, purified monoclonal antibodies can be cleaved with an enzyme, such as pepsin, and subjected to HPLC gel filtration. The appropriate fraction containing Fab fragments can then be collected and concentrated by membrane filtration and the like. For further description of general techniques for the isolation of active fragments of antibodies, see for example, Khaw, B. A. et al. J. Nucl. Med. 23:1011-1019 (1982); Rousseaux et al. Methods Enzymology, 121:663-69, Academic Press, 1986.

As used herein the term "specific" and "specifically" are used interchangeably to indicate that other biomolecules do not significantly bind to the antibody that is specifically binding to the biomolecule of interest. In some embodiments, the level of binding to a biomolecule other than a peptide comprising an epitope within a peptide results in a negligible (e.g., not determinable) binding affinity by means of ELISA or an affinity determination.

By "negligible binding" a binding is meant, which is at least about 85%, particularly at least about 90%, more particularly at least about 95%, even more particularly at least about 98%, but especially at least about 99% and up to 100% less than the binding to a peptide comprising an epitope within a peptide.

As used herein the term "epitope" refers to a site on a target molecule (e.g., an antigen, such as a protein) to which an antigen-binding molecule (e.g., an antibody or antibody fragment) binds. Epitopes can be formed both from contiguous or adjacent noncontiguous residues (e.g., amino acid residues) of the target molecule. Epitopes formed from contiguous residues (e.g., amino acid residues) typically are also called linear epitopes. An epitope typically includes at least 5 and up to about 12 residues, mostly between 6 and 10 residues (e.g. amino acid residues).

As used herein, the term "CDR" refers to the hypervariable region of an antibody. The term "hypervariable region", "HVR", or "HV", when used herein refers to the regions of an antibody variable domain which are hypervariable in sequence and/or form structurally defined loops. Generally, antibodies comprise six hypervariable regions; three in the VH (H1, H2, H3), and three in the VL (L1, L2, L3). A number of hypervariable region delineations are in use and are encompassed herein. The Kabat Complementarity Determining Regions are based on sequence variability and are the most commonly used (Kabat et al., Sequences of Proteins of Immunological Interest, 5th Ed. Public Health Service, National Institutes of Health, Bethesda, Md. (1991)). The letters "HC" and "LC" preceding the term "CDR" refer, respectively, to a CDR of a heavy chain and a light chain.

As used herein, the terms "homology" and "identity" are used interchangeably. Calculations of sequence homology or identity between sequences are performed as follows.

In order to determine the percent (%) identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 75%, 80%, 82%, 84%, 85%, 86%, 87%, 88%, 89%, 90%, 91%, 92%, 93%, 94%, 95%, 96%, 97%, 98%, 99%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman et al. (1970) *J. Mol. Biol.* 48:444-453) algorithm which has been incorporated into the GAP program in the GCG software package (available at www.gcg.com), using either a BLOSUM 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) are a BLOSUM 62 scoring matrix with a gap penalty of 12, a gap extend penalty of 4, and a frameshift gap penalty of 5.

Alternatively, the percent identity between two amino acid or nucleotide sequences can be determined using the algorithm of Meyers et al. (1989) CABIOS 4:11-17) which has been incorporated into the ALIGN program (version 2.0), using a PAM120 weight residue table, a gap length penalty of 12 and a gap penalty of 4.

As used herein the term "conservative amino acid substitution" refers to replacement of an amino acid residue with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

In one embodiment, the antibody is a polyclonal antibody. In one embodiment, the antibody is a humanized antibody, a human antibody, a murine antibody or a chimeric antibody.

In one embodiment, the antigen binding fragment thereof is an antigen-binding fragment (Fab) or a single-chain variable fragment (scFv). In a further embodiment, said fragment is selected from the group consisting of Fab, Fab', F(ab)2, F(ab')2, and scFv. It will be appreciated that $X_1$ can represent any suitable antibody or antigen binding fragment attachment moiety and that the choice of said group will depend upon the amino acid residue selected as the attachment point within the antibody.

In one embodiment, X represents —S— or —N(H)—. In a further embodiment, X represents-N(H)—. In this embodiment, L is conjugated to compounds of formula (I) according to one of the two following structures:

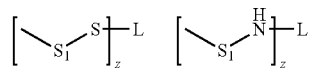

wherein $S_1$ and z are as defined herein and L represents an antibody or antigen binding fragment thereof terminated with reactive thiol or lysine groups. Such reacting thiol or cysteine groups may be available on the antibody or antigen binding fragment thereof or they may be introduced through site specific modifications to the peptide chain, to deliver additional points of conjugation via engineered amino acid residues (Nat. Biotechnol. 2008, 925; Nat. Biotechnol. 2012, 184). Alternatively, site specific amino acids may be incorporated into the desired peptide chain to enable orthogonal chemical reactivity for site specific conjugation (OPRD (2016), 20, 852-866). Examples of amino acids with orthogonal reactivity include p-acetylphenylalanine (pAcPhe, J. Mol. Biol. 2011, 595), para-azidomethyl-1-phenylalanine (pAMF, Bioconjug. Chem 2014, 351), N6-((2-azidoethoxy) carbonyl)-L-lysine (Bioconjug. Chem. 2015, 2249).

It will be appreciated that the antibody or antigen binding fragments of the present invention will be configured to bind to a therapeutic target which is either a cancer cell or a specific pathogen.

In one embodiment, the antibody or antigen binding fragments are configured to bind to a cancer cell. In a further embodiment, the antibody or antigen binding fragments specifically bind to a tumour-associated antigen whose cell surface expression on a tumour cell is different to its expression on a healthy cell.

In a preferred embodiment, the antibody or antigen binding fragment binds to a target on a cancer cell or pathogen. Preferred targets include: EGFR, HER2, HER3, CD22, EpCAM, PSMA, PSCA, FLT-3, CD30, CD20, CD33, CD23, CD2, CD37, CD25, CD73, CD47, LGR-5, CD80, CD86, CD70, CD74, CD40, CD19, CD79b, CA-125, c-met, CXCR4, DR5, PD-1, PD1L, LeY, MUC1, MUC2, MUC3, MUC4, MUC5ac, MIP-1A, MIP-1B, KIT, TRAIL receptor (R1 and R2), CXCR4, CEACAM, IGF-1R, carbonic anhydrase IX, PDGFRa, CD137, CD276, mesothelin, VEGFR, P-cadherin, CD56, bacterial Psl, bacterial lipopolysaccharide, galactan-lll epitope of bacterial LPS, bacterial PcrV, RSV F protein, ROR1, BAFF-R, CD40, CD52, CD71, CD38, CD269, CD319, CD307, CD7, CD123 and CD135.

In a yet preferred embodiment, the antibody or antigen binding fragment binds to a target on a cancer cell or pathogen. Preferred targets include: EGFR, HER2, HER3, CD22, EpCAM, PSMA, PSCA, FLT-3, CD30, CD20, CD33, CD23, CD2, CD37, CD25, CD73, CD47, LGR-5, CD80, CD86, CD70, CD74, CD40, CD19, CD79b, CA-125, c-met, CXCR4, DR5, PD-1, PDIL, LeY, MUC1, MUC2, MUC3, MUC4, MUC5ac, MIP-1A, MIP-1B, KIT, TRAIL receptor (R1 and R2), CXCR4, CEACAM, IGF-1R, carbonic anhydrase IX, PDGFRa, CD137, CD276, mesothelin, VEGFR, P-cadherin, CD56, bacterial Psl, bacterial lipopolysaccharide, galactan-Ill epitope of bacterial LPS, bacterial PcrV and RSV F protein.

Anti-EGFR Antibodies

In a further embodiment, the antibody or antigen binding fragment is an Epidermal Growth Factor Receptor (EGFR) binding epitope. EGFR is well known to be over-expressed in several human cancer types. The high expression on certain cancer cells makes EGFR an attractive target for new therapies. In one embodiment, the EGFR binding antibody or antigen binding fragment is an epitope which binds to any of the EGFR subfamily selected from: EGFR (ErbB-1), HER2/c-neu (ErbB-2), Her 3 (ErbB-3) and Her 4 (ErbB-4). Examples of suitable EGFR binding antibodies include but are not limited to Cetuximab, Nimotuzumab, Matuzumab, Zalutumumab, and Panitumumab.

In one embodiment, said antibody or antigen binding fragment thereof is selected from an EGFR antibody or a fragment thereof, such as cetuximab, cetuximab Fab or nimotuzumab, in particular an EGFR antibody or fragment thereof, such as cetuximab, cetuximab Fab, having at least 80% sequence identity to SEQ ID NOS: 1 and 2:

*Anal. Chem.* 80, 1737-45; and (c) IMGT database available at www.imgt.org; www.drugbank.ca or WO 2016/196682.

In a further embodiment the cetuximab antibody or antigen binding fragment thereof recognises and specifically binds EGFR and has heavy and light chain variable domains having at least 80%, 82%, 84%, 85%, 86%, 87%, 88%, 89%, 90%, 91%, 92%, 93%, 94%, 95%, 96%, 97%, 98%, 99%, or 100% sequence identity to SEQ ID NOS: 1 and 2.

In a further embodiment, fragments of EGFR binding antibodies may be selected as examples of L. Typical examples include but are not limited to cetuximab Fab (Li, S. et al (2005) Cancer Cell 7, 301-311); cetuximab scFv (U.S. Pat. No. 7,060,808); Panitumumab Fab (Sickmier E. A. et al (2016) PLOSOne 11, 9, e0163366); Panitumumab scFv (U.S. Pat. No. 6,235,883) and D2C7 scFv (US 2013/0022598; Clin Cancer Res 2013, 19 (17), 4717-4727).

Anti-CD20 Antibodies

In a further embodiment, the antibody or antigen binding fragment is a CD20 binding epitope. Removal of CD20 expressing cells (e.g. B cells), is well known to have therapeutic benefit in the treatment of haematological cancers such as leukemias and lymphomas. Examples of suitable CD20 binding antibodies include but are not limited to rituximab, ocrelizumab, ofatumumab and obinutuzumab.

In one embodiment, said antibody or antigen binding fragment thereof is selected from a CD20 antibody or a

| Sequence ID NO | Sequence |
|---|---|
| Cetuximab Heavy chain (SEQ ID NO: 1) | QVQLKQSGPGLVQPSQSLSITCTVSGFSLTNYGVHWVRQSP GKGLEWLGVIWSGGNTDYN TPFTSRLSINKDNSKSQVFFKMNSLQSNDTAIYYCARALTYYD YEFAYWGQGTLVTVSAA STKGPSVFPLAPSSKSTSGGTAALGCLVKDYFPEPVTVSWNS GALTSGVHTFPAVLQSSG LYSLSSVVTVPSSSLGTQTYICNVNHKPSNTKVDKKVEPKSCD KTHTCPPCPAPELLGGP SVFLFPPKPKDTLMISRTPEVTCVVVDVSHEDPEVKFNWYVD GVEVHNAKTKPREEQYNS TYRVVSVLTVLHQDWLNGKEYKCKVSNKALPAPIEKTISKAKG QPREPQVYTLPPSRDEL TKNQVSLTCLVKGFYPSDIAVEWESNGQPENNYKTTPPVLDS DGSFFLYSKLTVDKSRWQ QGNVFSCSVMHEALHNHYTQKSLSLSPGK |
| Cetuximab Light chain (SEQ ID NO: 2) | DILLTQSPVILSVSPGERVSFSCRASQSIGTNIHWYQQRTNGS PRLLIKYASESISGIPS RFSGSGSGTDFTLSINSVESEDIADYYCQQNNNWPTTFGAGT KLELKRTVAAPSVFIFPP SDEQLKSGTASVVCLLNNFYPREAKVQWKVDNALQSGNSQE SVTEQDSKDSTYSLSSTLT LSKADYEKHKVYACEVTHQGLSSPVTKSFNRGEC |

In a further embodiment, the EGFR antibody is cetuximab, a hybrid mouse/human chimeric antibody comprising both heavy and light chain sequences as disclosed in (a) Li et al. (2005) *Cancer Cell* 7, 301-11; (b) Dubois et al. (2008)

fragment thereof, such as rituximab or rituximab Fab, in particular a CD20 antibody or fragment thereof, such as rituximab or rituximab Fab, having at least 80% sequence identity to SEQ ID NOS: 3 and 4:

| Rituximab Heavy chain (SEQ ID NO: 3) | QVQLQQPGAELVKPGASVKMSCKASGYTFTSYNMHWVKQTPGRGLEWIGAIYPG NGDTSY NQKFKGKATLTADKSSSTAYMQLSSLTSEDSAVYYCARSTYYGGDWYFNVWGAGT TVTVS AASTKGPSVFPLAPSSKSTSGGTAALGCLVKDYFPEPVTVSWNSGALTSGVHTFPAV LQS SGLYSLSSVVTVPSSSLGTQTYICNVNHKPSNTKVDKKAEPKSCDKTHTCPPPAPELL G GPSVFLFPPKPKDTLMISRTPEVTCVVVDVSHEDPEVKFNWYVDGVEVHNAKTKPR EEQY |

```
                          -continued
           NSTYRVVSVLTVLHQDWLNGKEYKCKVSNKALPAPIEKTISKAKGQPREPQVYTLPP
           SRD
           ELTKNQVSLTCLVKGFYPSDIAVEWESNGQPENNYKTTPPVLDSDGSFFLYSKLTVDK
           SR
           WQQGNVFSCSVMHEALHNHYTQKSLSLSPGK Rituximab Light  QIVLSQSPAILSASPGEKVTMTCRASSSVSYIHWFQQKPGSSPKPWIYATSNLASGVP
chain (SEQ ID NO: VR
4)
                 FSGSGSGTSYSLTISRVEAEDAATYYCQQWTSNPPTFGGGTKLEIKRTVAAPSVFIFPP
                 S
                 DEQLKSGTASVVCLLNNFYPREAKVQWKVDNALQSGNSQESVTEQDSKDSTYSLSS
                 TLTL
                 SKADYEKHKVYACEVTHQGLSSPVTKSFNRGEC
```

In a further embodiment, the CD20 antibody is rituximab, a hybrid mouse/human chimeric antibody comprising both heavy and light chain sequences as disclosed in (a) U.S. Pat. No. 5,736,137, (b) Wang, B. et al (2013) *Analyst* 138, 3058-3065 and (c) IMGT database available at www.imgt.org; www.drugbank.ca.

In a further embodiment the rituximab antibody or antigen binding fragment thereof recognises and specifically binds CD20 and has heavy and light chain variable domains having at least 80%, 82%, 84%, 85%, 86%, 87%, 88%, 89%, 90%, 91%, 92%, 93%, 94%, 95%, 96%, 97%, 98%, 99%, or 100% sequence identity to SEQ ID NOS: 3 and 4.

In a further embodiment, fragments of CD20 binding antibodies may be selected as examples of L. Typical examples include but are not limited to rituximab Fab (Du, J. et al (2007) *J. Biological Chem.* 282, 15073-15080).

In a further embodiment, the CD20 antibody or fragment thereof is selected from rituximab or rituximab Fab.

Anti-HER-2 Antibodies

In a further embodiment, the antibody or antigen binding fragment is a HER-2 binding epitope. Examples of suitable HER-2 binding antibodies include but are not limited to trastuzumab and pertuzumab.

In a further embodiment, the antibody is trastuzumab, a humanised antibody comprising both heavy and light chain sequences as disclosed in (a) Carter, P. L. et al. (1992) *Proc. Natl. Acad. Sci.* USA 89, 4285-9; (b) Kyoto Encyclopedia of Genes and Genomes (KEGG). (KEGG DRUG entry D03257); and (c) IMGT database available at www.imgt.org.

In one embodiment, said antibody or antigen binding fragment thereof is selected from a HER2 antibody or a fragment thereof, such as trastuzumab or trastuzumab Fab, in particular a HER2 antibody or fragment thereof, such as trastuzumab or trastuzumab Fab, having at least 80% sequence identity to SEQ ID NOS: 5 and 6:

```
Sequence ID NO        Sequence

Trastuzumab Heavy     EVQLVESGGG  LVQPGGSLRL  SCAASGFNIK  DTYIHWVRQA
chain (SEQ ID NO: 5)  PGKGLEWVAR  IYPTNGYTRY  ADSVKGRFTI  SADTSKNTAY  LQMNSLRAED
                      TAVYYCSRWG
                      GDGFYAMDYW  GQGTLVTVSS  ASTKGPSVFP  LAPSSKSTSG  GTAALGCLVK
                      DYFPEPVTVS
                      WNSGALTSGV  HTFPAVLQSS  GLYSLSSVVT  VPSSSLGTQT  YICNVNHKPS
                      NTKVDKKVEP
                      KSCDKTHTCP  PCPAPELLGG  PSVFLFPPKP  KDTLMISRTP  EVTCVVVDVS
                      HEDPEVKFNW
                      YVDGVEVHNA  KTKPREEQYN  STYRVVSVLT  VLHQDWLNGK  EYKCKVSNKA
                      LPAPIEKTIS
                      KAKGQPREPQ  VYTLPPSREE  MTKNQVSLTC  LVKGFYPSDI  AVEWESNGQP
                      ENNYKTTPPV
                      LDSDGSFFLY  SKLTVDKSRW  QQGNVFSCSV  MHEALHNHYT  QKSLSLSPG Trastuzumab light     DIQMTQSPSS  LSASVGDRVT  ITCRASQDVN  TAVAWYQQKP
chain (SEQ ID NO: 6)  GKAPKLLIYS  ASFLYSGVPS  RFSGSRSGTD  FTLTISSLQP  EDFATYYCQQ
                      HYTTPPTFGQ
                      GTKVEIKRTV  AAPSVFIFPP  SDEQLKSGTA  SVVCLLNNFY  PREAKVQWKV
                      DNALQSGNSQ
                      ESVTEQDSKD  STYSLSSTLT  LSKADYEKHK  VYACEVTHQG  LSSPVTKSFN
                      RGEC
```

Pathogen Specific Antibody Targets

In an alternative embodiment, the antibody or antigen binding fragments are configured to bind to a specific pathogen. In a further embodiment, the antibody or antigen binding fragments are configured to bind *S. aureus* and *Pseudomonas aeruginosa* bacteria. Examples of suitable antibodies include but are not limited to those reported in WO 2015/196011, WO 2012/170807 and WO 2014/074528.

Conjugates

Any antibody or fragment thereof disclosed herein may be conjugated to the linkers described herein containing one or more rhamnose. The invention pertains to the ability to choose the optimal number of rhamnose units per antibody or Fab fragment whilst retaining efficacy of the antibody or fragment thereof. The type of conjugation may be selected by one skilled in the art to enable the highest yield and purity of the isolated material based on the terminal functionality of the linker and the surface reactivity or selected reactive site of the antibody or fragment thereof. In some embodiments conjugation is facilitated by a thiol addition to a maleimide moiety. Alternatively conjugation may be facilitated by the amide bond formation between an amino group and an activated ester such as an NHS ester.

When a conjugate includes several reactive sites leading to multiple conjugation reactions, it is to be understood that the aforementioned ranges may refer to the actual or average number of linker molecules per antibody or fragment thereof.

As used herein, the term 'LAR' (Linker: Antibody Ratio) refers to the actual number or average number of linker molecules that have successfully conjugated to the antibody or fragment thereof. LAR is equivalent to the value of the integer defined herein as "z". Various methods of determining the linker loading are known in the art.

Conjugate Properties

In any of the various embodiments described herein, an antibody or fragment thereof will be capable of retaining its binding efficacy to its target whilst enabling optimal recruitment of anti-Gal. In one embodiment, cetuximab retains its ability to bind EGFR whilst being conjugated to an average of up to five, such as up to twenty.

In some embodiments, a conjugate of the invention may exhibit one or more of the following properties:
a) Conjugation of the linkers to the antibody or fragment thereof may not significantly alter the binding efficacy to the target over the unconjugated counterpart;
b) Conjugation of the hapten containing linkers may enable high levels of LAR without concomitantly high levels of aggregation due to the hydrophilic properties of the carbohydrates;
c) Addition of the hapten containing linkers may enable the antibody or fragment thereof to be more stable;
d) A preference for heavy or light chain conjugation depending on the chosen linker and/or conjugation approach;
e) Conjugation of the linkers to the antibody or fragment thereof may lead to an enhanced pharmacokinetic profile;
f) The resulting bifunctional antibodies and fragments thereof may exhibit enhanced EC50 binding properties to the target.

Salts and Derivatives Thereof

A reference to a compound of formula (I) and sub-groups thereof also includes ionic forms, salts, solvates, isomers (including geometric and stereochemical isomers), tautomers, N-oxides, esters, isotopes and protected forms thereof, for example, as discussed below; preferably, the salts or tautomers or isomers or N-oxides or solvates thereof; and more preferably, the salts or tautomers or N-oxides or solvates thereof, even more preferably the salts or tautomers or solvates thereof. Hereinafter, compounds and their ionic forms, salts, solvates, isomers (including geometric and stereochemical isomers), tautomers, N-oxides, esters, isotopes and protected forms thereof as defined in any aspect of the invention (except intermediate compounds in chemical processes) are referred to as "compounds of the invention".

Compounds of formula (I) can exist in the form of salts, for example acid addition salts or, in certain cases salts of organic and inorganic bases such as carboxylate, sulfonate and phosphate salts. All such salts are within the scope of this invention, and references to compounds of formula (I) include the salt forms of the compounds. In one embodiment, the compound of formula (I) exists as the phosphate salt.

The salts of the present invention can be synthesized from the parent compound that contains a basic moiety by conventional chemical methods such as methods described in Pharmaceutical Salts: Properties, Selection, and Use, P. Heinrich Stahl (Editor), Camille G. Wermuth (Editor), ISBN: 3-90639-026-8, Hardcover, 388 pages, August 2002. Generally, such salts can be prepared by reacting the base forms of these compounds with the appropriate base or acid in water or in an organic solvent, or in a mixture of the two; generally, nonaqueous media such as ether, ethyl acetate, ethanol, isopropanol, or acetonitrile are used.

Acid addition salts (mono- or di-salts) may be formed with a wide variety of acids, both inorganic and organic. Examples of acid addition salts include mono- or di-salts formed with an acid selected from the group consisting of acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (+)-DL-lactic), lactobionic, maleic, malic, (−)-L-malic, malonic, (+)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-amino-salicylic, sebacic, stearic, succinic, sulfuric, tannic, (+)-L-tartaric, thiocyanic, p-toluenesulfonic, undecylenic and valeric acids, as well as acylated amino acids and cation exchange resins.

One particular group of salts consists of salts formed from acetic, hydrochloric, hydriodic, phosphoric, nitric, sulfuric, citric, lactic, succinic, maleic, malic, isethionic, fumaric, benzenesulfonic, toluenesulfonic, methanesulfonic (mesylate), ethanesulfonic, naphthalenesulfonic, valeric, acetic, propanoic, butanoic, malonic, glucuronic and lactobionic acids. One particular salt is the hydrochloride salt. Another particular salt is the hydrogensulfate salt, also known as a hemisulfate salt.

Salts further include, by way of example only, sodium, potassium, calcium, magnesium, ammonium, tetraalkylammonium, and the like.

Where the compounds of formula (I) contain an amine function, these may form quaternary ammonium salts, for example by reaction with an alkylating agent according to methods well known to the skilled person. Such quaternary ammonium compounds are within the scope of formula (I).

The compounds of the invention may exist as mono- or di-salts depending upon the pKa of the acid from which the salt is formed.

The salt forms of the compounds of the invention are typically pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Pharmaceutically acceptable solvates of the compound of the invention are within the scope of the invention.

Compounds of formula (I) containing an amine function may also form N-oxides. A reference herein to a compound of formula (I) that contains an amine function also includes the N-oxide.

Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle.

N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4$^{th}$ Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (mCPBA), for example, in an inert solvent such as dichloromethane.

It will be appreciated by those skilled in the art that certain protected derivatives of compounds of formula (I), which may be made prior to a final deprotection stage, may not possess pharmacological activity as such, but may, in certain instances, be administered orally or parenterally and thereafter metabolised in the body to form compounds of the invention which are pharmacologically active. Such derivatives may therefore be described as "prodrugs". All such prodrugs of compounds of the invention are included within the scope of the invention. Examples of pro-drug functionality suitable for the compounds of the present invention are described in Drugs of Today, Volume 19, Number 9, 1983, pp 499-538 and in Topics in Chemistry, Chapter 31, pp 306-316 and in "Design of Prodrugs" by H. Bundgaard, Elsevier, 1985, Chapter 1 (the disclosures in which documents are incorporated herein by reference). It will further be appreciated by those skilled in the art, that certain moieties, known to those skilled in the art as "pro-moieties", for example as described by H. Bundgaard in "Design of Prodrugs" (the disclosure in which document is incorporated herein by reference) may be placed on appropriate functionalities when such functionalities are present within compounds of the invention.

Also included within the scope of the compound and various salts of the invention are polymorphs thereof.

Compounds of formula (I) may exist in a number of different geometric isomeric, and tautomeric forms and references to compounds of formula (I) include all such forms. For the avoidance of doubt, where a compound can exist in one of several geometric isomeric or tautomeric forms and only one is specifically described or shown, all others are nevertheless embraced by formula (I).

The present invention includes all pharmaceutically acceptable isotopically-labeled compounds of the invention, i.e. compounds of formula (I), wherein one or more atoms are replaced by atoms having the same atomic number, but an atomic mass or mass number different from the atomic mass or mass number usually found in nature.

Examples of isotopes suitable for inclusion in the compounds of the invention comprise isotopes of hydrogen, such as $^2$H(D) and $^3$H(T), carbon, such as $^{11}$C, $^{13}$C and $^{14}$C, fluorine, such as $^{18}$F, nitrogen, such as $^{13}$N and $^{15}$N, oxygen, such as $^{15}$O, $^{17}$O and $^{18}$O.

Certain isotopically-labelled compounds of formula (I), for example, those incorporating a radioactive isotope, are useful in drug and/or substrate tissue distribution studies. The compounds of formula (I) can also have valuable diagnostic properties in that they can be used for detecting or identifying the formation of a complex between a labelled compound and other molecules, peptides, proteins, enzymes or receptors. The detecting or identifying methods can use compounds that are labelled with labelling agents such as radioisotopes, enzymes, fluorescent substances, luminous substances (for example, luminol, luminol derivatives, luciferin, aequorin and luciferase), etc. The radioactive isotopes tritium, i.e. $^3$H (T), and carbon-14, i.e. $^{14}$C, are particularly useful for this purpose in view of their ease of incorporation and ready means of detection.

Substitution with heavier isotopes such as deuterium, i.e. $^2$H (D), may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining target occupancy.

Isotopically-labeled compounds of formula (I) can generally be prepared by conventional techniques known to those skilled in the art or by processes analogous to those described in the accompanying Examples and Preparations using appropriate isotopically-labeled reagents in place of the non-labeled reagent previously employed.

Methods for the Preparation of Compounds of Formula (I)

In this section, as in all other sections of this application unless the context indicates otherwise, references to formula (I) also include all other sub-groups and examples thereof as defined herein.

The compounds pertaining to the invention described herein may be prepared in a stepwise synthetic sequence as illustrated in the Processes and Schemes below. Compounds of formula (I) can be prepared in accordance with synthetic methods well known to the skilled person. For example, one skilled in the art will appreciate that the chemical steps and choice of protecting groups may be managed in any order to enable synthetic success.

In some embodiments, a compound of formula (A) may comprise a linker ($S_B$) that comprises one or more linker components. Exemplary linker components include but are not limited to 6-maleimidocaproyl (MC), maleimidopropanoyl (MP), valine-citrulline (vc) alanine-phenylalanine (ala-phe), N-succinimidyl 4-(2-pyridylthio) pentanoate (SPP) and 4-(n-maleimidomethyl)cyclohexane 1-carboxylate (SMCC).

In some embodiments, a compound of formula (A) may comprise a linker ($S_B$) that is capable of reacting with a free thiol on an antibody to form a covalent bond. The compounds of the invention expressly contemplate but are not limited to antibody conjugates prepared with linker reagents: BMPEO, BMPS, EMCS, GMBS, HBVS, LC-SMCC, MBS, MPBH, SBAP, SIA, SIAB, SMCC, SMPB, sulfo-EMCS, sulfo-GMBS, sulfo-KMUS, sulfo-MBS, sulfo-SIAB, sulfo-SMCC, sulfo-SMPB and SVSB. Other functional groups besides pyrrolidine-2,5-dione (maleimide) which are reactive with a thiol group on an antibody include iodoacetamide, bromocetamide, vinyl pyridine disulphide, pyridyl disulphide, isocyanate, isothiocyanate, activated esters, sulfonyl chlorides and acid chlorides.

In some embodiments, a linker has the functionality that is capable of reacting with electrophilic groups on an antibody. Exemplary electrophilic groups include but are not limited to aldehyde, ketone and carbonyl groups. Additionally a heteroatom of the reactive functionality of the linker may react with an electrophilic group on an antibody. Typical examples include but are not limited to hydrazine, oxime, amino, hydrazide, thiosemicarbazone, hydrazine carboxylate and aryl hydrazide.

In some embodiments, a compound of formula (A) may comprise a linker ($S_B$) that is capable of reacting with a free amine on an antibody to form a covalent bond. The compounds of the invention expressly contemplate but are not limited to antibody conjugates prepared using carboxylic acid activating agents such as: N-hydroxysuccinimide (NHS), 2-succinimido-1,1,3,3-tetra-methyluronium tetrafluoroborate (TSTU), and benzotriazol-1-yl-oxytripyrrolidinophosphonium hexafluorophosphate (PyBOP).

According to a further aspect of the invention there is provided a process for preparing a compound of formula (I) as defined hereinbefore which comprises:
(a) preparing a compound of formula (IA) wherein X represents —NH— by reacting a compound of formula (IIA) wherein $S_1$ is terminated with a N-hydroxysuccinimide group with compounds of formula (IIIA) wherein the antibody or antigen binding fragment contains at least one reactive amino group:

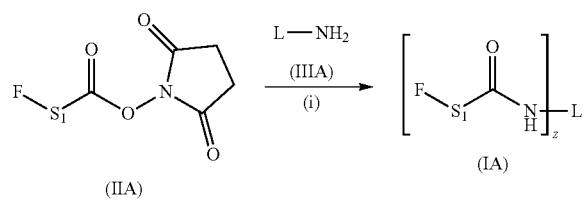

wherein F, $S_1$ and L are as defined hereinbefore; or
(b) preparing a compound of formula (IB) wherein $X_1$ represents —S— by reacting a compound of formula (IIIB) wherein the antibody or antigen binding fragment contains at least one reactive thiol group with a compound of formula (IIB) wherein $S_1$ is terminated with maleimide:

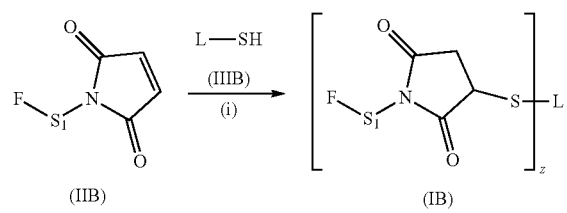

wherein F, $S_1$ and L are as defined hereinbefore; and/or
(c) interconversion of a compound of formula (I) or protected derivative thereof to a further compound of formula (I) or protected derivative thereof.

Process (a) typically comprises an amide bond formation reaction in the presence of an activated ester. Typical conditions comprise incubation of the linker-NHS ester with antibodies or fragments thereof that contain a reactive amino, in a suitable buffer at room temperature. Typical Linker: Antibody ratios (LAR) are dependent on the number of free amino groups present on the antibody or fragment thereof in combination with the choice of linker equivalents used, but typically range from 2-20.

Process (b) typically comprises a thiol-maleimide reaction; a Michael addition reaction of a reactive thiol group with an α, β-unsaturated ketone such as maleimide. Preferred conditions comprise incubation of the linker-maleimide intermediates with antibodies or fragments thereof that contain a reactive thiol, in a suitable buffer as described herein at room temperature. Typical Linker: Antibody ratios (LAR) are dependent on the number of free thiol groups present on the antibody or fragment thereof, but typically range from 2-8.

Process (c) typically comprises interconversion procedures known by one skilled in the art. For example, in compounds of formula (I), a first substituent may be converted by methods known by one skilled in the art into a second, alternative substituent. A wide range of well known functional group interconversions are known by a person skilled in the art for converting a precursor compound to a compound of formula (I) and are described in *Advanced Organic Chemistry* by Jerry March, 4th Edition, John Wiley & Sons, 1992. For example possible metal catalysed functionalisations such as using organo-tin reagents (the Stille reaction), Grignard reagents and reactions with nitrogen nucleophiles are described in 'Palladium Reagents and Catalysts' [Jiro Tsuji, Wiley, ISBN 0-470-85032-9] and Handbook of OrganoPalladium Chemistry for Organic Synthesis [Volume 1, Edited by Ei-ichi Negishi, Wiley, ISBN 0-471-31506-0].

If appropriate, the reactions previously described in processes (a) and (b) are followed or preceded by one or more reactions known to the skilled of the art and are performed in an appropriate order to achieve the requisite substitutions defined above to afford other compounds of formula (I). Non-limiting examples of such reactions whose conditions can be found in the literature include:
protection of reactive functions,
deprotection of reactive functions,
halogenation,
dehalogenation,
dealkylation,
alkylation and arylation of amine, aniline, alcohol and phenol,
Mitsunobu reaction on hydroxyl groups,
cycloaddition reactions on appropriate groups,
reduction of nitro, esters, cyano, aldehydes,
transition metal-catalyzed coupling reactions,
acylation,
sulfonylation/introduction of sulfonyl groups,
saponification/hydrolysis of ester groups,
amidification or transesterification of ester groups,
esterification or amidification of carboxylic groups,
halogen exchange,
nucleophilic substitution with amine, thiol or alcohol,
reductive amination,
oxime formation on carbonyl and hydroxylamine groups,
S-oxidation,
N-oxidation,
salification.

Compounds of formula (IIA) and (IIB) are either commercially available or prepared according to the methods described herein or referenced herein.

One skilled in the art will appreciate that one may choose the appropriate combination of steps described above to generate the highest yields for the Examples and Preparations described herein.

Pharmaceutical Compositions

While it is possible for the compound of formula (I) to be administered alone, it is preferable to present it as a pharmaceutical composition (e.g. formulation).

Thus, according to a further aspect, the invention provides a pharmaceutical composition, and methods of making a pharmaceutical composition comprising (e.g admixing) at least one compound of the invention together with one or more pharmaceutically acceptable excipients and optionally other therapeutic or prophylactic agents, as described herein.

It will be appreciated that when the pharmaceutical composition comprises one or more further therapeutic agents, said agents may comprise further differing compounds of formula (I).

The pharmaceutically acceptable excipient(s) can be selected from, for example, carriers (e.g. a solid, liquid or semi-solid carrier), adjuvants, diluents, fillers or bulking agents, granulating agents, coating agents, release-controlling agents, binding agents, disintegrants, lubricating agents, preservatives, antioxidants, buffering agents, suspending agents, thickening agents, flavouring agents, sweeteners, taste masking agents, stabilisers or any other excipients conventionally used in pharmaceutical compositions. Examples of excipients for various types of pharmaceutical compositions are set out in more detail below.

The term "pharmaceutically acceptable" as used herein pertains to compounds, materials, compositions, and/or dosage forms which are, within the scope of sound medical judgment, suitable for use in contact with the tissues of a subject (e.g. human) without excessive toxicity (i.e. generally recognised as safe (GRAS)), irritation, allergic response, or other problem or complication, commensurate with a reasonable benefit/risk ratio. Each carrier, excipient, etc. must also be "acceptable" in the sense of being compatible with the other ingredients of the formulation.

Pharmaceutical compositions containing compounds of the invention can be formulated in accordance with known techniques, see for example, Remington's Pharmaceutical Sciences, Mack Publishing Company, Easton, PA, USA.

The pharmaceutical compositions can be in any form suitable for parenteral, intranasal, intrabronchial, sublingual, ophthalmic, otic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery. The delivery can be by bolus injection, short term infusion or longer term infusion and can be via passive delivery or through the utilisation of a suitable infusion pump or syringe driver.

Pharmaceutical formulations adapted for parenteral administration include aqueous and non-aqueous sterile injection solutions which may contain anti-oxidants, buffers, bacteriostats, co-solvents, surface active agents, organic solvent mixtures, cyclodextrin complexation agents, emulsifying agents (for forming and stabilizing emulsion formulations), liposome components for forming liposomes, gellable polymers for forming polymeric gels, lyophilisation protectants and combinations of agents for, inter alia, stabilising the active ingredient in a soluble form and rendering the formulation isotonic with the blood of the intended recipient. Pharmaceutical formulations for parenteral administration may also take the form of aqueous and non-aqueous sterile suspensions which may include suspending agents and thickening agents (R. G. Strickly, Solubilizing Excipients in oral and injectable formulations, Pharmaceutical Research, Vol 21 (2) 2004, p 201-230).

The formulations may be presented in unit-dose or multi-dose containers, for example sealed ampoules, vials and prefilled syringes, and may be stored in a freeze-dried (lyophilised) condition requiring only the addition of the sterile liquid carrier, for example water for injections, immediately prior to use.

The pharmaceutical formulation can be prepared by lyophilising a compound of the invention. Lyophilisation refers to the procedure of freeze-drying a composition. Freeze-drying and lyophilisation are therefore used herein as synonyms.

Extemporaneous injection solutions and suspensions may be prepared from sterile powders, granules and tablets.

Pharmaceutical compositions of the present invention for parenteral injection can also comprise pharmaceutically acceptable sterile aqueous or non-aqueous solutions, dispersions, suspensions or emulsions as well as sterile powders for reconstitution into sterile injectable solutions or dispersions just prior to use.

Examples of suitable aqueous and non-aqueous carriers, diluents, solvents or vehicles include water, ethanol, polyols (such as glycerol, propylene glycol, polyethylene glycol, and the like), carboxymethylcellulose and suitable mixtures thereof, vegetable oils (such as sunflower oil, safflower oil, corn oil or olive oil), and injectable organic esters such as ethyl oleate. Proper fluidity can be maintained, for example, by the use of thickening or coating materials such as lecithin, by the maintenance of the required particle size in the case of dispersions, and by the use of surfactants.

The compositions of the present invention may also contain adjuvants such as preservatives, wetting agents, emulsifying agents, and dispersing agents. Prevention of the action of microorganisms may be ensured by the inclusion of various anti-bacterial and antifungal agents, for example, paraben, chlorobutanol, phenol, sorbic acid, and the like. It may also be desirable to include agents to adjust tonicity such as sugars, sodium chloride, and the like. Prolonged absorption of the injectable pharmaceutical form may be brought about by the inclusion of agents which delay absorption such as aluminium monostearate and gelatin.

In one preferred embodiment of the invention, the pharmaceutical composition is in a form suitable for i.v. administration, for example by injection or infusion. For intravenous or subcutaneous administration, the solution can be dosed as is, or can be injected into an infusion bag (containing a pharmaceutically acceptable excipient, such as 0.9% saline or 5% dextrose), before administration.

In another preferred embodiment, the pharmaceutical composition is in a form suitable for subcutaneous (s.c.) administration.

The compound of the invention may be formulated with a carrier and administered in the form of nanoparticles, the increased surface area of the nanoparticles assisting their absorption. In addition, nanoparticles offer the possibility of direct penetration into the cell. Nanoparticle drug delivery systems are described in "Nanoparticle Technology for Drug Delivery", edited by Ram B Gupta and Uday B. Kompella, Informa Healthcare, ISBN 9781574448573, published 13th March 2006. Nanoparticles for drug delivery are also described in J. Control. Release, 2003, 91 (1-2), 167-172, and in Sinha et al., Mol. Cancer Ther. August 1, (2006) 5, 1909.

The pharmaceutical compositions typically comprise from approximately 1% (w/w) to approximately 95% (w/w) active ingredient and from 99% (w/w) to 5% (w/w) of a pharmaceutically acceptable excipient or combination of excipients. Preferably, the compositions comprise from approximately 20% (w/w) to approximately 90% (w/w) active ingredient and from 80% (w/w) to 10% of a pharmaceutically acceptable excipient or combination of excipients. The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, pre-filled syringes, dragées, tablets or capsules.

The pharmaceutically acceptable excipient(s) can be selected according to the desired physical form of the formulation and can, for example, be selected from diluents (e.g solid diluents such as fillers or bulking agents; and liquid diluents such as solvents and co-solvents), disintegrants, buffering agents, lubricants, flow aids, release controlling (e.g. release retarding or delaying polymers or waxes) agents, binders, granulating agents, pigments, plasticizers, antioxidants, preservatives, flavouring agents, taste masking agents, tonicity adjusting agents and coating agents.

The skilled person will have the expertise to select the appropriate amounts of ingredients for use in the formulations. For example tablets and capsules typically contain 0-20% disintegrants, 0-5% lubricants, 0-5% flow aids and/or 0-99% (w/w) fillers/or bulking agents (depending on drug dose). They may also contain 0-10% (w/w) polymer binders, 0-5% (w/w) antioxidants, 0-5% (w/w) pigments. Slow release tablets would in addition contain 0-99% (w/w) release-controlling (e.g. delaying) polymers (depending on dose). The film coats of the tablet or capsule typically contain 0-10% (w/w) polymers, 0-3% (w/w) pigments, and/or 0-2% (w/w) plasticizers.

Parenteral or subcutaneous formulations typically contain 0-20% (w/w) buffers, 0-50% (w/w) cosolvents, and/or 0-99% (w/w) Water for Injection (WFI) (depending on dose and if freeze dried). Formulations for intramuscular depots may also contain 0-99% (w/w) oils.

The compounds of the invention can also be formulated as solid dispersions. Solid dispersions are homogeneous extremely fine disperse phases of two or more solids. Solid solutions (molecularly disperse systems), one type of solid dispersion, are well known for use in pharmaceutical technology (see (Chiou and Riegelman, J. Pharm. Sci., 60, 1281-1300 (1971)) and are useful in increasing dissolution rates and increasing the bioavailability of poorly water-soluble drugs.

The pharmaceutical formulations may be presented to a patient in "patient packs" containing an entire course of treatment in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions. One example of a patient pack includes a prefilled syringe. Such pre-filled syringes already contain the drug substance. The front end portion of a pre-filled syringe to which a needle is to be attached is sealed with a nozzle cap. Prior to injection, the nozzle cap is removed from the front end portion and a needle is attached thereto. A gasket is then slid by pushing a plunger rod toward the front end portion so that the drug is expelled.

Compositions for nasal delivery include ointments, creams, sprays, patches, gels, liquid drops and inserts (for example intraocular inserts). Such compositions can be formulated in accordance with known methods.

Examples of formulations for rectal or intra-vaginal administration include pessaries and suppositories which may be, for example, formed from a shaped moldable or waxy material containing the active compound. Solutions of the active compound may also be used for rectal administration.

Compositions for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active compound together with an inert solid powdered diluent such as lactose.

The compound of the invention will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within these ranges, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

The active compound will be administered to a patient in need thereof (for example a human or animal patient) in an amount sufficient to achieve the desired therapeutic effect.

Therapeutic Uses

According to a further aspect of the invention, there is provided a compound of formula (I) as defined herein for use in therapy.

It will be appreciated that the therapeutic use of the compounds of the invention is determined by the selection of the antibody or antigen binding fragment thereof.

For example, in the embodiment when the antibody or antigen binding fragment thereof is an EGFR antibody (e.g. cetuximab or nimotuzumab) or a fragment thereof the compound of formula (I) is for use in the treatment of cancer.

Thus, according to a further aspect of the invention there is provided a compound of formula (I) as defined herein wherein the antibody or antigen binding fragment thereof is an EGFR antibody (e.g. cetuximab or nimotuzumab) or a fragment thereof for use in the treatment of cancer.

According to a further aspect of the invention there is provided a method of treating cancer which comprises administering to an individual in need thereof a compound of formula (I) as defined herein wherein the antibody or antigen binding fragment thereof is EGFR antibody (e.g. cetuximab or nimotuzumab) or a fragment thereof.

Furthermore, in the embodiment when the antibody or antigen binding fragment thereof is a pathogen specific antibody or a fragment thereof, the compound of formula (I) is for use in the treatment of a bacterial infection.

Thus, according to a further aspect of the invention there is provided a compound of formula (I) as defined herein wherein the antibody or antigen binding fragment thereof is a pathogen specific antibody or a fragment thereof, for use in the treatment of a bacterial infection.

According to a further aspect of the invention there is provided a method of treating a bacterial infection which comprises administering to an individual in need thereof a compound of formula (I) as defined herein wherein the antibody or antigen binding fragment thereof is a pathogen specific antibody or a fragment thereof.

The compound of the invention is generally administered to a subject in need of such administration, for example a human or animal patient, preferably a human.

The compound of the invention will typically be administered in amounts that are therapeutically or prophylactically useful and which generally are non-toxic. However, in certain situations (for example in the case of life threatening diseases), the benefits of administering a compound of the invention may outweigh the disadvantages of any toxic effects or side effects, in which case it may be considered desirable to administer a compound of the invention in amounts that are associated with a degree of toxicity.

The compound of the invention may be administered over a prolonged term (i.e. chronic administration) to maintain beneficial therapeutic effects or may be administered for a short period only (i.e. acute administration). Alternatively they may be administered in a continuous manner or in a manner that provides intermittent dosing (e.g. a pulsatile manner).

A typical daily dose of the compound of the invention can be in the range from 100 picograms to 100 milligrams per kilogram of body weight, more typically 5 nanograms to 25 milligrams per kilogram of bodyweight, and more usually 10 nanograms to 15 milligrams per kilogram (e.g. 10 nanograms to 10 milligrams, and more typically 1 microgram per kilogram to 20 milligrams per kilogram, for example 1 microgram to 10 milligrams per kilogram) per kilogram of bodyweight although higher or lower doses may be administered where required. The compound of the invention can either be administered on a daily basis or on a repeat basis every 2, or 3, or 4, or 5, or 6, or 7, or 10 or 14, or 21, or 28 days for example. Alternatively, the compound of the invention can be administered by infusion, multiple times per day.

The compound of the invention may be administered in a range of doses, for example 1 to 1500 mg, 2 to 800 mg, or 5 to 500 mg, e.g. 2 to 200 mg or 10 to 1000 mg, particular examples of doses including 10, 20, 50 and 80 mg. The compound of the invention may be administered once or more than once each day. The compound of the invention can be administered continuously (i.e. taken every day without a break for the duration of the treatment regimen). Alternatively, the compound of the invention can be administered intermittently (i.e. taken continuously for a given period such as a week, then discontinued for a period such as a week and then taken continuously for another period such as a week and so on throughout the duration of the treatment regimen). Examples of treatment regimens involving intermittent administration include regimens wherein administration is in cycles of one week on, one week off; or two weeks on, one week off; or three weeks on, one week off; or two weeks on, two weeks off; or four weeks on two weeks off; or one week on three weeks off—for one or more cycles, e.g. 2, 3, 4, 5, 6, 7, 8, 9 or 10 or more cycles.

In one particular dosing schedule, a patient will be given an infusion of a compound of the invention for periods of one hour daily for up to ten days in particular up to five days for one week, and the treatment repeated at a desired interval such as two to four weeks, in particular every three weeks.

More particularly, a patient may be given an infusion of a compound of the invention for periods of one hour daily for 5 days and the treatment repeated every three weeks.

In another particular dosing schedule, a patient is given an infusion over 30 minutes to 1 hour followed by maintenance infusions of variable duration, for example 1 to 5 hours, e.g. 3 hours.

In a further particular dosing schedule, a patient is given a continuous infusion for a period of 12 hours to 5 days, and in particular a continuous infusion of 24 hours to 72 hours.

Ultimately, however, the quantity of compound of the invention administered and the type of composition used will be commensurate with the nature of the disease or physiological condition being treated and will be at the discretion of the physician.

It will be appreciated that the compound of the invention can be used as a single agent or in combination with other therapeutic agents. Combination experiments can be performed, for example, as described in Chou T C, Talalay P. Quantitative analysis of dose-effect relationships: the combined effects of multiple drugs or enzyme inhibitors. Adv Enzyme Regulat 1984; 22:27-55.

Where the compound of the invention is administered in combination therapy with one, two, three, four or more other therapeutic agents (preferably one or two, more preferably one), the agents can be administered simultaneously or sequentially. In the latter case, the two or more agents will be administered within a period and in an amount and manner that is sufficient to ensure that an advantageous or synergistic effect is achieved. When administered sequentially, they can be administered at closely spaced intervals (for example over a period of 5-10 minutes) or at longer intervals (for example 1, 2, 3, 4 or more hours apart, or even longer periods apart where required), the precise dosage regimen being commensurate with the properties of the therapeutic agent(s). These dosages may be administered for example once, twice or more per course of treatment, which may be repeated for example every 7, 14, 21 or 28 days.

It will be appreciated that the preferred method and order of administration and the respective dosage amounts and regimes for each component of the combination will depend on the particular other medicinal agent and compound of the invention being administered, their route of administration, the particular tumour being treated and the particular host being treated. The optimum method and order of administration and the dosage amounts and regime can be readily determined by those skilled in the art using conventional methods and in view of the information set out herein.

The weight ratio of the compound of the invention and the one or more other therapeutic agent(s) when given as a combination may be determined by the person skilled in the art. Said ratio and the exact dosage and frequency of administration depends on the particular compound of the invention and the other therapeutic agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compound of present invention. A particular weight ratio for the compound of the invention and another therapeutic agent may range from 1/10 to 10/1, more in particular from 1/5 to 5/1, even more in particular from 1/3 to 3/1.

Anti-Cancer Therapy

Examples of cancers (and their benign counterparts) which may be treated (or inhibited) include, but are not limited to tumours of epithelial origin (adenomas and carcinomas of various types including adenocarcinomas, squamous carcinomas, transitional cell carcinomas and other carcinomas) such as carcinomas of the bladder and urinary tract, breast, gastrointestinal tract (including the esophagus, stomach (gastric), small intestine, colon, rectum and anus), liver (hepatocellular carcinoma), gall bladder and biliary system, exocrine pancreas, kidney, lung (for example adenocarcinomas, small cell lung carcinomas, non-small cell lung carcinomas, bronchioalveolar carcinomas and mesotheliomas), head and neck (for example cancers of the tongue, buccal cavity, larynx, pharynx, nasopharynx, tonsil, salivary glands, nasal cavity and paranasal sinuses), ovary, fallopian tubes, peritoneum, vagina, vulva, penis, cervix, myometrium, endometrium, thyroid (for example thyroid follicular carcinoma), adrenal, prostate, skin and adnexae (for example melanoma, basal cell carcinoma, squamous cell carcinoma, keratoacanthoma, dysplastic naevus); haematological malignancies (i.e. leukemias, lymphomas) and premalignant haematological disorders and disorders of borderline malignancy including haematological malignancies and related conditions of lymphoid lineage (for example acute lymphocytic leukemia [ALL], chronic lymphocytic leukemia [CLL], B-cell lymphomas such as diffuse large B-cell lymphoma [DLBCL], follicular lymphoma, Burkitt's lymphoma, mantle cell lymphoma, T-cell lymphomas and leukaemias, natural killer [NK] cell lymphomas, Hodgkin's lymphomas, hairy cell leukaemia, monoclonal gammopathy of uncertain significance, plasmacytoma, multiple myeloma, and post-transplant lymphoproliferative disorders), and haematological malignancies and related conditions of myeloid lineage (for example acute myelogenousleukemia [AML], chronic myelogenousleukemia [CML], chronic myelomonocyticleukemia [CMML], hypereosinophilic syndrome, myeloproliferative disorders such as polycythaemia vera, essential thrombocythaemia and primary myelofibrosis, myeloproliferative syndrome, myelodysplastic syndrome, and promyelocyticleukemia); tumours of mesenchymal origin, for example sarcomas of soft tissue, bone or cartilage such as osteosarcomas, fibrosarcomas, chondrosarcomas, rhabdomyosarcomas, leiomyosarcomas, liposarcomas, angiosarcomas, Kaposi's sarcoma, Ewing's sarcoma, synovial sarcomas, epithelioid sarcomas, gastrointestinal stromal tumours, benign and malignant histiocytomas, and dermatofibrosarcomaprotuberans; tumours of the central or peripheral nervous system (for example astrocytomas, gliomas and glioblastomas, meningiomas, ependymomas, pineal tumours and schwannomas); endocrine tumours (for example pituitary tumours, adrenal tumours, islet cell tumours, parathyroid tumours, carcinoid tumours and medullary carcinoma of the thyroid); ocular and adnexal tumours (for example retinoblastoma); germ cell and trophoblastic tumours (for example teratomas, seminomas, dysgerminomas, hydatidiform moles and choriocarcinomas); and paediatric and embryonal tumours (for example medulloblastoma, neuroblastoma, Wilms tumour, and primitive neuroectodermal tumours); or syndromes, congenital or otherwise, which leave the patient susceptible to malignancy (for example Xeroderma Pigmentosum).

In one embodiment, the cancer is a solid tumor. In a further embodiment, the cancer is breast cancer, ovarian cancer, cervical cancer, colorectal cancer, liver cancer, prostate cancer or lung cancer.

In one embodiment, the cancer comprises a haematological malignancy. In a further embodiment, the haematological malignancy is one of myeloma, non-Hodgkin's lymphoma or chronic lymphocytic leukaemia.

Examples of other anticancer therapeutic agents or treatments that may be administered together (whether concurrently or at different time intervals) with the compound of the invention include but are not limited to:
Topoisomerase I inhibitors;
Antimetabolites;
Tubulin targeting agents;
DNA binder and topoisomerase II inhibitors;
Alkylating Agents;
Monoclonal Antibodies;
Anti-Hormones;
Signal Transduction Inhibitors;
Proteasome Inhibitors;
DNA methyl transferases;
Cytokines and retinoids;
Chromatin targeted therapies;
Radiotherapy; and
Other therapeutic or prophylactic agents, such as immunotherapy agents.

The compound of the invention may also be administered in conjunction with non-chemotherapeutic treatments such as radiotherapy, photodynamic therapy, gene therapy; surgery and controlled diets.

For use in combination therapy with another chemotherapeutic agent, the compound of the invention and one, two, three, four or more other therapeutic agents can be, for example, formulated together in a dosage form containing two, three, four or more therapeutic agents i.e. in a unitary pharmaceutical composition containing all components. In an alternative embodiment, the individual therapeutic agents may be formulated separately and presented together in the form of a kit, optionally with instructions for their use.

Anti-Infective Therapy

Examples of infective agents include any pathogen such as a bacteria, fungus, parasite or virus. Thus, in one embodiment, the disease or disorder mediated by and/or caused by an infective agent is bacterial infection.

Examples of such as bacterial infection include infection by the following bacteria: *Staphylococcus* sp. such as *Staphylococcus aureus* (including methicillin resistant *Staphylococcus aureus* (MRSA)), Clostridia sp (e.g. *Clostridium difficile, Clostridium tetani* and *Clostridium botulinum*), *Enterobacter* species, *Mycobacterium tuberculosis, Shigella* sp. such as Shigelladysenteriae, *Campylobacter* sp. such as *Campylobacter jejuni, Enterococcus* sp. such as *Enterococcus faecalis, Bacillus anthracis, Yersinia pestis, Bordetella pertussis, Streptococcal species, Salmonella thyphimurim, Salmonella enterica, Chlamydia* species, Treponemapallidum, *Neisseria gonorrhoeae*, Borreliaburgdorferi, *Vibrio cholerae, Corynebacterium diphtheriae, Helicobacter pylori*, Gram-negative pathogens, such as *Acinetobacter baumannii, Pseudomonas aeruginosa, Klebsiella pneumoniae*, and *Escherichia coli* (and including strains that are resistant to one or more classes of antibiotics, especially multi-drug resistant (MDR) strains).

Vaccine Therapy

According to a further aspect of the invention, there is provided a vaccine comprising an immunoconjugate as defined herein.

According to a further aspect of the invention, there is provided an adjuvant comprising an immunoconjugate as defined herein.

EXAMPLES

The invention will now be illustrated, but not limited, by reference to the specific embodiments described in the following Examples. Compounds are named using an automated naming package such as AutoNom (MDL) or ChemDraw or are as named by the chemical supplier.

The following synthetic procedures are provided for illustration of the methods used; for a given preparation or step the precursor used may not necessarily derive from the individual batch synthesised according to the step in the description given.

Analytical Methods
UPLC
　Column: Waters Acquity UPLC BEH C18 1.7 µm 2.1*50 mm Part no. 186002350
　Mobile phase A: Water
　Mobile phase B: Acetonitrile
　Mobile phase C: 2% v/v Ammonia (35% v/v) in Water
　Flow rate: 0.8 mL/min
　Column Temp: 40° C.
　Gradient start: 350 µL before injection
　Data collection: Diode Array 215-350 nm 1.2 nm resolution
UPLC Method 1

| Time / mins | A (%) | B (%) | C (%) |
|---|---|---|---|
| 0.0 | 93 | 2 | 5 |
| 4.0 | 0 | 95 | 5 |
| 4.6 | 0 | 95 | 5 |

Abbreviations
　Wherein the following abbreviations have been used, the following meanings apply: aq. is aqueous;
　is chemical shift in ppm;
　DMF is dimethylformamide;
　DMSO is dimethylsulphoxide;
　DSG is di-(N-succinimydyl) glutarate;
　HATU is O-(7-azabenzotriazol-1-yl)-N,N,N',N'-tetramethyluronium hexafluorophosphate;
　HCl is hydrochloric acid;
　HPLC is high performance liquid chromatography;
　µ is micro;
　m is multiplet;
　Mal is maleimide;
　MeCN is acetonitrile;
　MeOH is methanol;
　mins is minutes;
　mL is millilitre;
　MMTr is monomethoxytrityl;
　MS is mass spectrometry;
　NHS is N-hydroxysuccinimide; or N-hydroxysuccinimidyl;
　NMR is nuclear magnetic resonance;
　Pd/C is (typically 5%-10%) palladium on charcoal hydrogenation catalyst (water-wet);
　ppm is parts per million;
　Rt is retention time;
　s is singlet;
　TEA is triethylamine; and
　TFA is trifluoroacetic acid.

Preparations 1-9 describe the methods used to prepare intermediates from the key linker molecules required for conjugation into the Examples, as described by processes (a)-(c).

Preparation 1
Alpha-Gal-Linker-NHS

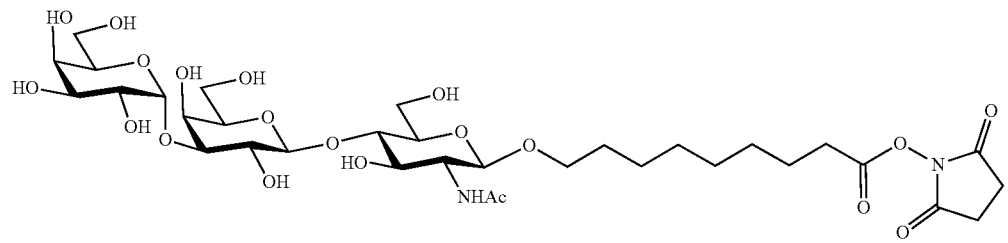

The alpha-Gal-$(CH_2)_8$—COO—NHS linker was purchased from V-Labs Inc.

Preparation 2
Rhamnose-Linker-NHS

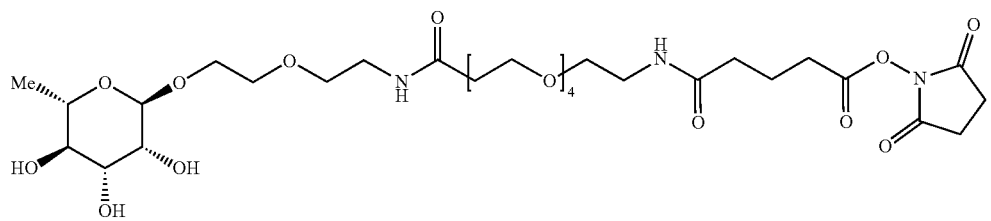

A solution of the Rhamnose-Linker-NH$_2$ (Preparation 3, 24 mmol) was dissolved in 1:1 anhydrous DMF: DMSO (1062 µL) with stirring. Di-(N-succinimidyl) glutarate (39.49 mg, 120 mmol) was added as a 300 mM solution in 1:1 anhydrous DMF: DMSO (400 µL). The reaction was stirred for 1 hour at room temperature under a positive nitrogen atmosphere. The reaction was purified using reverse phase column chromatography (10×250 mm Hichrom ACE 10) eluting with 1-50% MeCN in 1% TFA in water. The desired fractions were lyophilised to dryness over 24 hours to afford the desired compound that was taken directly on to the next step.

Preparation 3

1-Amino-N-(2-(2-(((2R,3R,4R,5R,6S)-3,4,5-Trihydroxy-6-Methyltetrahydro-2H-Pyran-2-Yl)Oxy)Ethoxy)Ethyl)-3,6,9,12-Tetraoxapentadecan-15-Amide

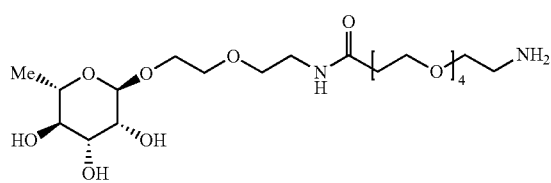

To a solution of benzyl (15-oxo-21-(((2R,3R,4R,5R,6S)-3,4,5-trihydroxy-6-methyltetrahydro-2H-pyran-2-yl)oxy)-3,6,9,12,19-pentaoxa-16-azahenicosyl) carbamate (Preparation 4, 242 mg, 382 µmol) in MeOH/water (1:1 v: v, 20 mL) was added 5% Pd/C (25 mg). The reaction was de-gassed under vacuum and stirred under a hydrogen atmosphere (Balloon pressure) for 18 hours overnight. The reaction was filtered through a syringe filter (0.2 µm) and concentrated in vacuo to afford the title compound as a colourless oil (161 mg, 85%). UPLC (Method 1): Rt=1.94 mins, MS m/z ES$^+$499.4 [M+H]$^+$ Preparation 4

Benzyl (15-Oxo-21-(((2R,3R,4R,5R,6S)-3,4,5-Trihydroxy-6-Methyltetrahydro-2H-Pyran-2-Yl)Oxy)-3,6,9,12,19-Pentaoxa-16-Azahenicosyl) Carbamate

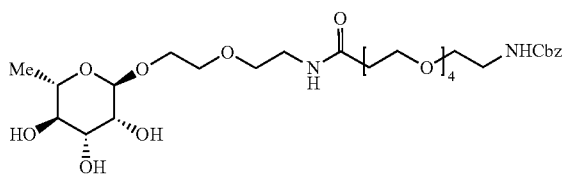

To a solution 3-oxo-1-phenyl-2,7, 10, 13, 16-pentaoxa-4-azanonadecan-19-oic acid (153 mg, 385 µmol) in DMF (5 mL) was added TEA (161 µL, 1.16 mmol) and a solution of (2R,3R,4R,5R,6S)-2-(2-(2-aminoethoxy) ethoxy)-6-methyltetrahydro-2H-pyran-3,4,5-triol (WO2018 006063, 145 mg, 578 µmol) in DMF (5 mL) to afford a colourless solution. HATU was added (220 mg, 578 µmol) and the reaction was stirred for 1 hour. The reaction was concentrated in vacuo and the residue purified using reverse phase column chromatography eluting with 5-45% MeCN in water modified with 0.1% TEA to afford the title compound as a colourless glass (242 mg, 99%).

UPLC (Method 1): Rt=1.35 mins, MS m/z ES$^+$633.3 [M+H]$^+$

EXAMPLES

Monomer Content by Size Exclusion HPLC (SEC)

The aggregate content of each conjugate was assessed by chromatography on a TOSOH TSKgel G3000SWXL 7.8 mm×30 cm, 5 µm column at 0.5 mL/min in 10% IPA, 0.2M Potassium Phosphate, 0.25M Potassium Chloride, pH 6.95. Samples were loaded neat and data collected at 214, 252 and 280 nm. All reported data are at 280 nm. Data for the respective Examples is exemplified in FIGS. 1-6.

MS Analysis

The Fab fragment conjugates were analysed by mass spectrometry as described below: Instrument: Waters Synapt G2-Si Samples were introduced by microLC on a Waters Acquity m-class UPLC.

Method: 1 µL of each sample was desalted on-line on a microbore C4 column and the resulting mass/charge envelopes were processed with the maxent algorithm to give uncharged masses for the intact proteins.

Data for the respective Examples is exemplified in FIGS. 1-6.

LAR

Linker loading has either been calculated using MS analysis or estimated using SDS-PAGE gel analysis. It will be appreciated that there will batch to batch variation with respect to the linker-antibody ratios (LARs). For example, certain linker-antibody combinations will generate varying LAR values.

Antibody Conjugates (Cetuximab)

Cetuximab (Merck Serono; Lot No: 223155, exp: 09/2020, with a molecular weight of 152,000 Da was used for the conjugations below. Calculations were based on an Abs$_{0.1\%}$ 280 nm of 1.45 cm$^{-1}$ mg/mL$^{-1}$, a UV analysis of 4.7 mg/mL and calibration curves by SEC at 214 nm.

Digestion of Cetuximab to Cetuximab-Fab

Figure 7A:
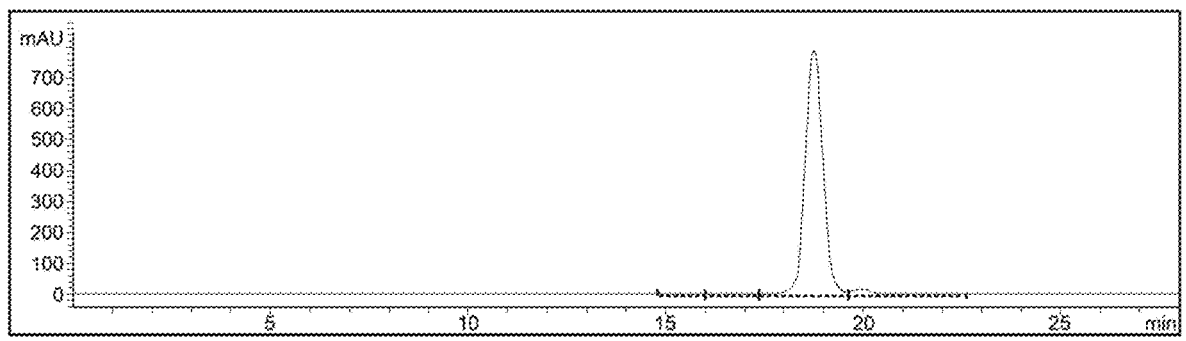
(FIG. 7A) SEC analysis of cetuximab-Fab.
Figure 7B:
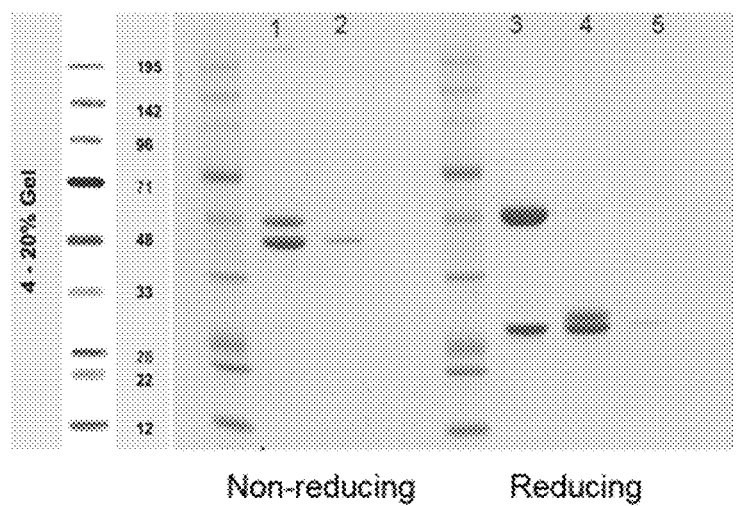
(FIG. 7B) SDS-PAGE analysis of cetuximab-Fab.
Figure 7C:
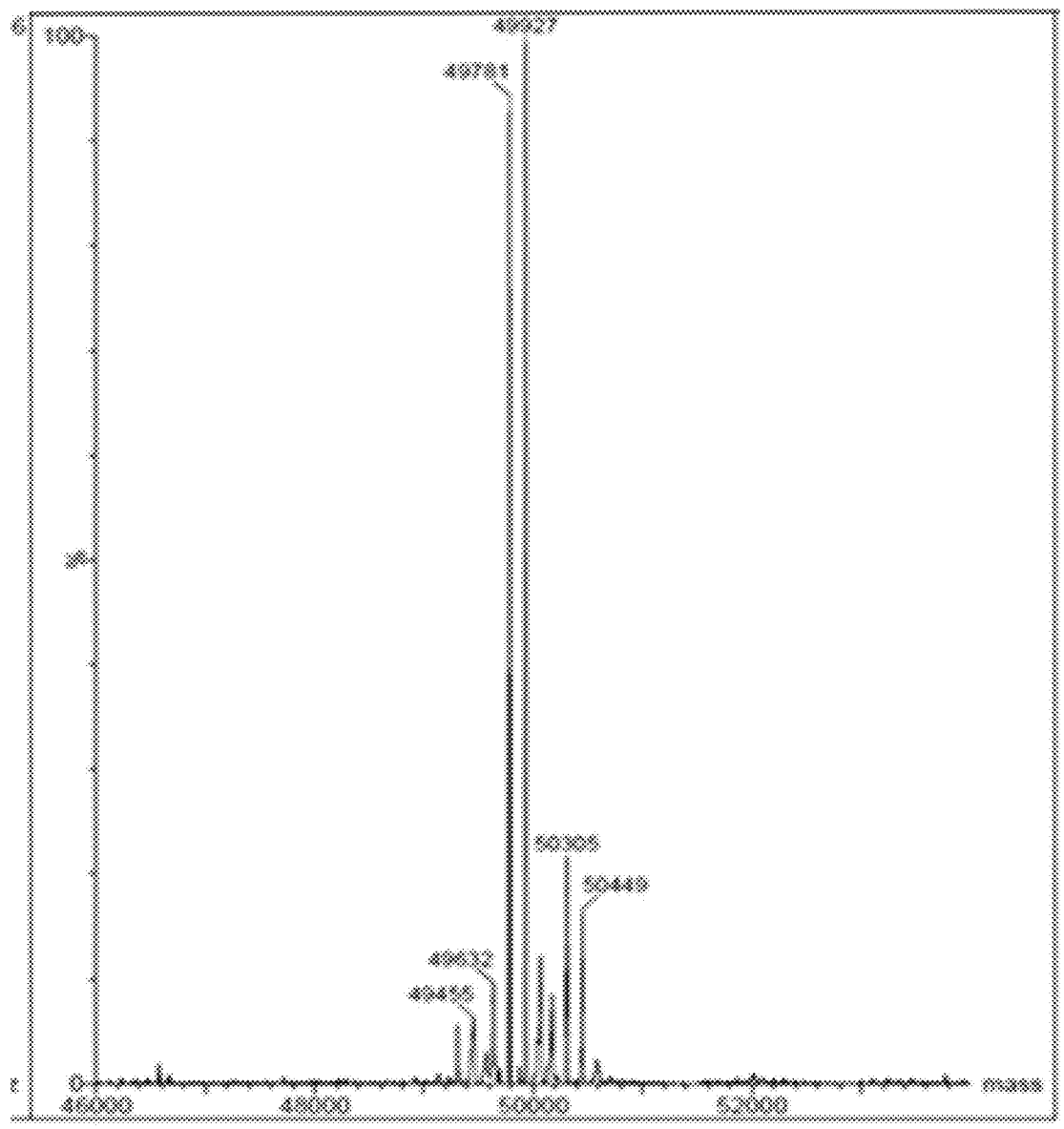
(FIG. 7C) MS analysis of cetuximab-Fab.
Figure 8A:
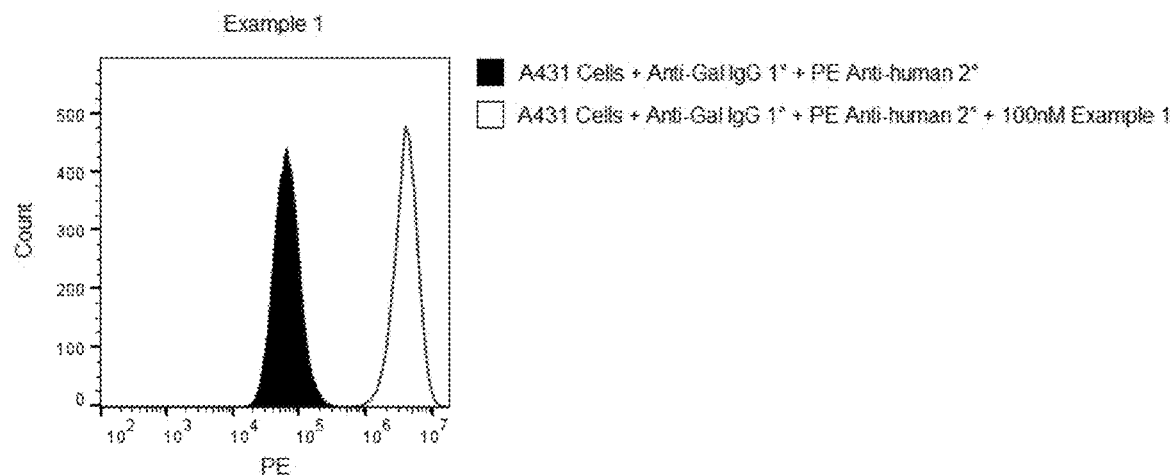
FIG. 8: Demonstrates the capture of anti-alpha galactosyl IgG antibodies to the cell surface using Examples 1-4, (FIGS. 8A-8D, respectively). The shift in fluorescence intensity (PE) occurs due to the binding event at each end of the molecule.
Figure 8B:
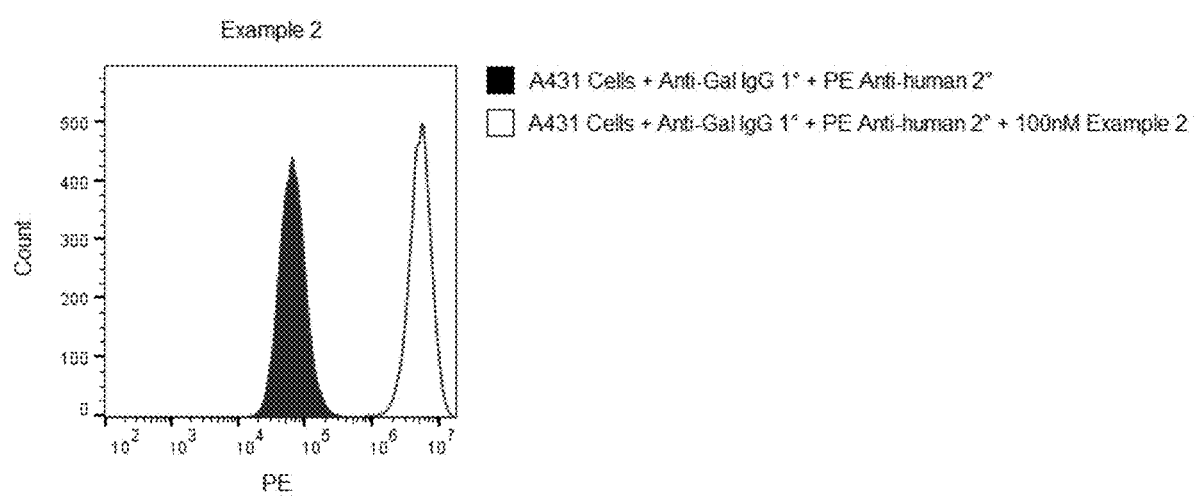
Figure 8C:
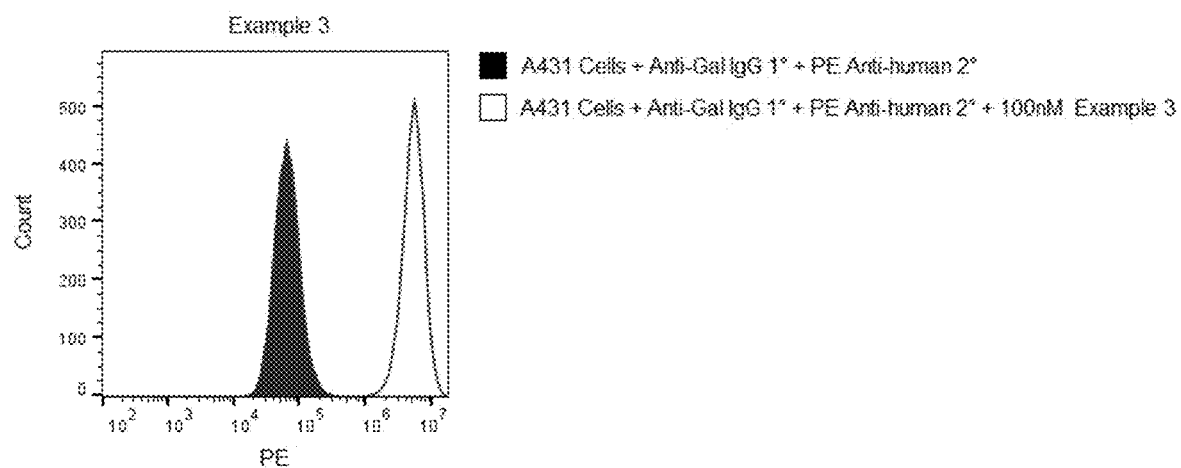
Figure 8D:
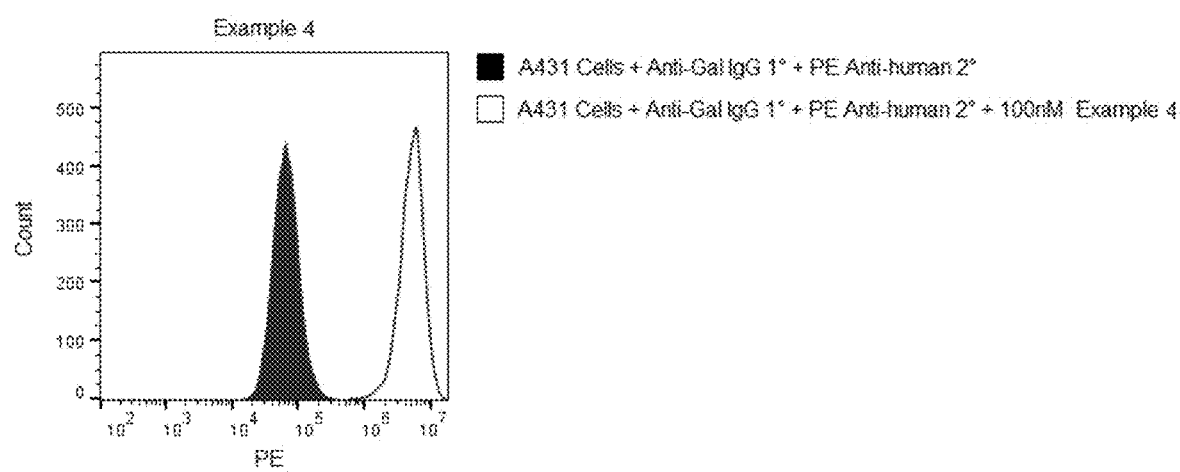

Cetuximab (60 mg, 4.7 mg/mL) was buffer exchanged into digestion buffer (20 mM NaPi, 20 mM cysteine, 10 mM EDTA at pH=7) and concentrated to 3 mL at 20 mg/mL. Immobilised papain (3 mL, Thermo Fisher #20341, loading: 250 µg/mL resin, activity: 16-40 BAEE/mg papain) was equilibrated in digestion buffer and incubated with the concentrated cetuximab at 37° C. for 15 hours. The digest products were collected by filtration and eluted through a protein A column. The non-binding Fab fragments passed through the column and the flow through was collected. The Fab fragments were subject to discontinuous diafiltration via vivaspin centrifugation (10 kDa MWCO filter) into 50 mM NaPi, 150 mM NaCl and 2 mM EDTA at pH=8. The final concentration achieved was 5.6 mg/ml (see FIGS. 7A-7C).

Cetuximab Buffer Exchange

Cetuximab (20 mg) was bound to Protein A resin (GE Healthcare, HiTrap MabSelect Sure, 1 mL) and column washed with a solution of 50 mM KPi, 50 mM NaCl and 2 mM EDTA at pH=8. The antibody was eluted with 100 mM citrate buffer at pH=3 and buffer exchanged into Lysine conjugation buffer (50 mM NaPi, 150 mM NaCl, 2 mM EDTA, pH=8) with concentration to approximately 6 mg/mL. The solution was analysed by SEC to afford cetuximab in a solution suitable for lysine conjugation (18.2 mg, 91% yield, at 6.4 mg/mL, 100% monomer content).

General Lysine Conjugation Method

The above solution of cetuximab or cetuximab-Fab was incubated with 20, 40 or [60+40] molar equivalents of 50 mM Preparation 1 or 25 mM Preparation 2 with 10% v/v DMF co-solvent for 2 hours at 30° C. SEC analysis was used to confirm successful conjugation and the reaction was quenched by the addition of glycine to 1 mM. The conjugates were desalted into PBS pH=7.4 via G25 resin filtration. The remaining unbound linker was removed with 12x diavolume diafiltration in PBS pH=7.4 with a 10 or 30 kDa MWCO filter. The solution was concentrated to 2-3 mg/mL and 0.2 μM filtered to afford the desired conjugate.

Example 1

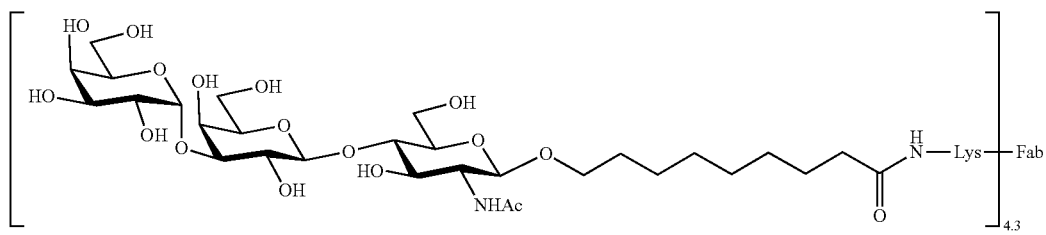

Example 1 was prepared according to the General Lysine Conjugation Method using 20 equivalents of Preparation 1 and cetuximab-Fab.

Av. LAR: 4.3; Av. total no of alpha-Gal units: 4.3

Figure 1B:
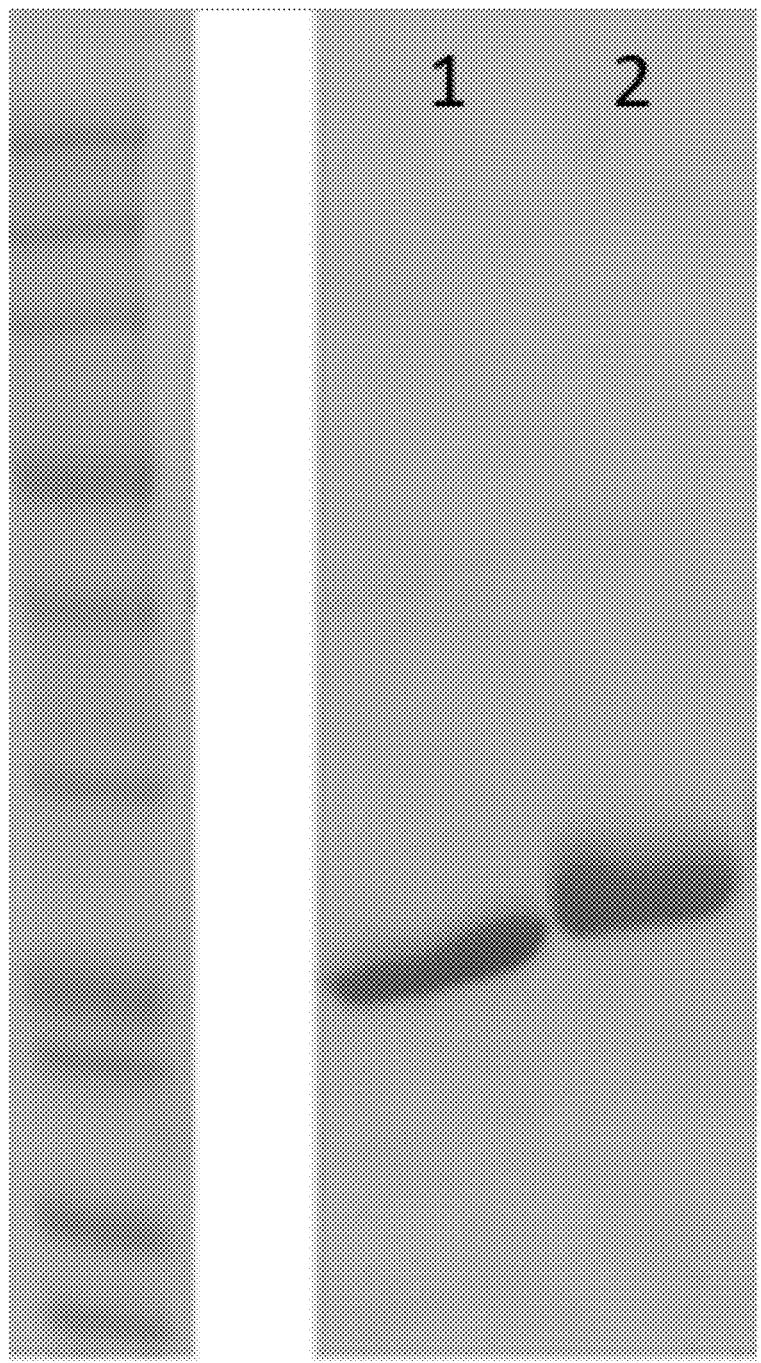
(FIG. 1B) SDS-PAGE analysis of Example 1 (lane 2) and Cetuximab-Fab (lane 1)
Figure 1C:
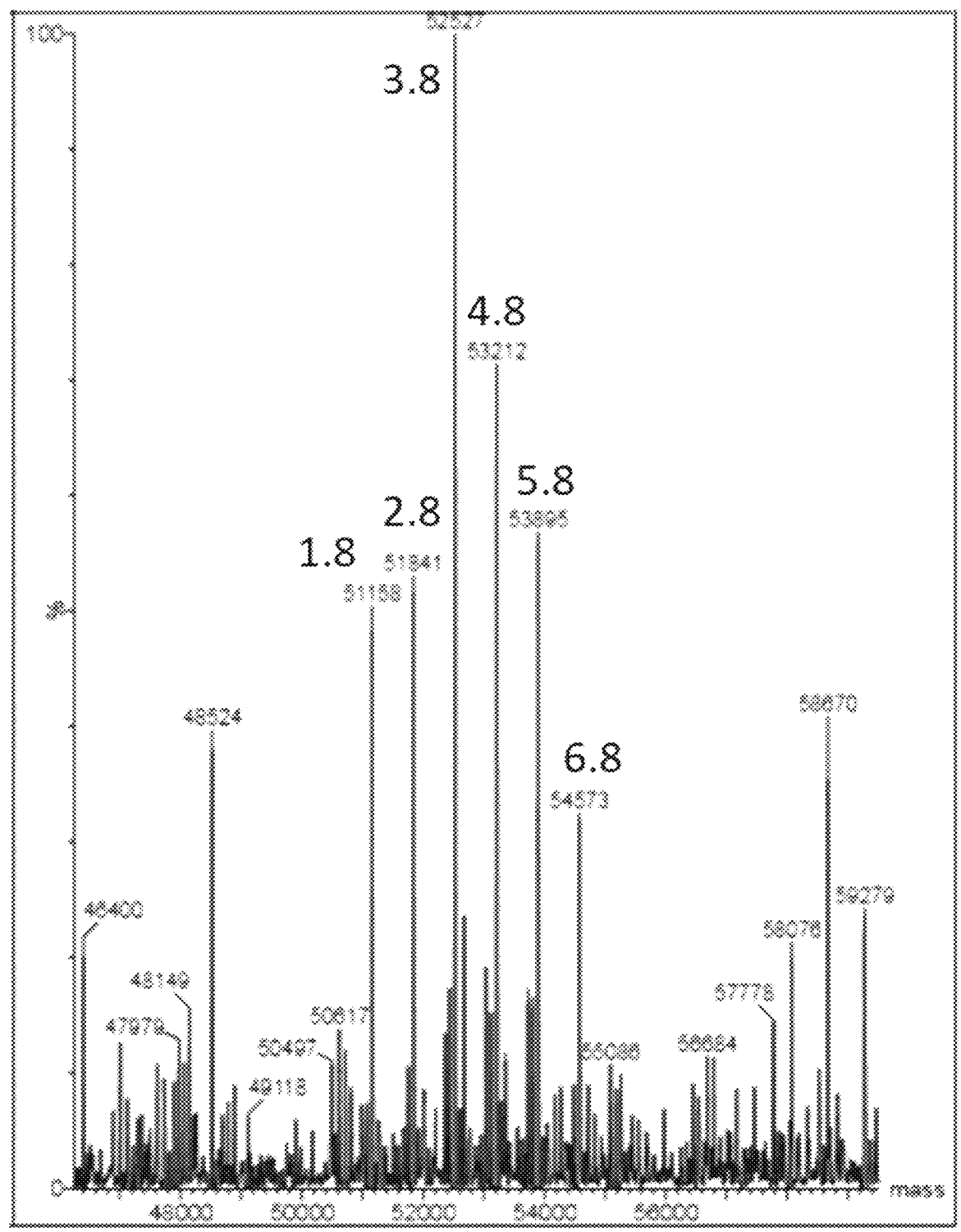
(FIG. 1C) MS analysis of Example 1.

SEC Analysis: Rt=18.02 minutes, 98.3% monomer content (FIGS. 1A-1C).

Example 2

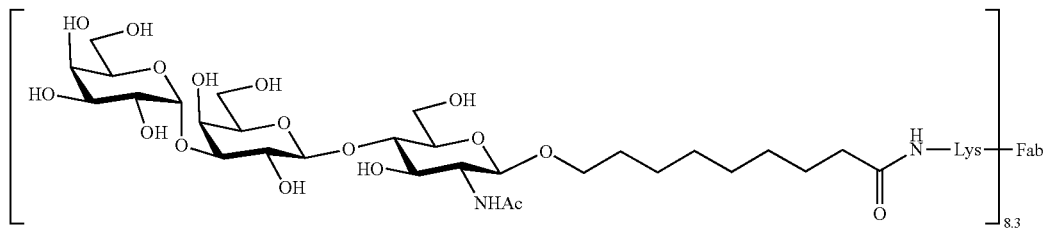

Example 2 was prepared according to the General Lysine Conjugation Method using 40 equivalents of Preparation 1 and cetuximab-Fab.

Av. LAR: 8.3; Av. total no of alpha-Gal units: 8.3

Figure 2A:
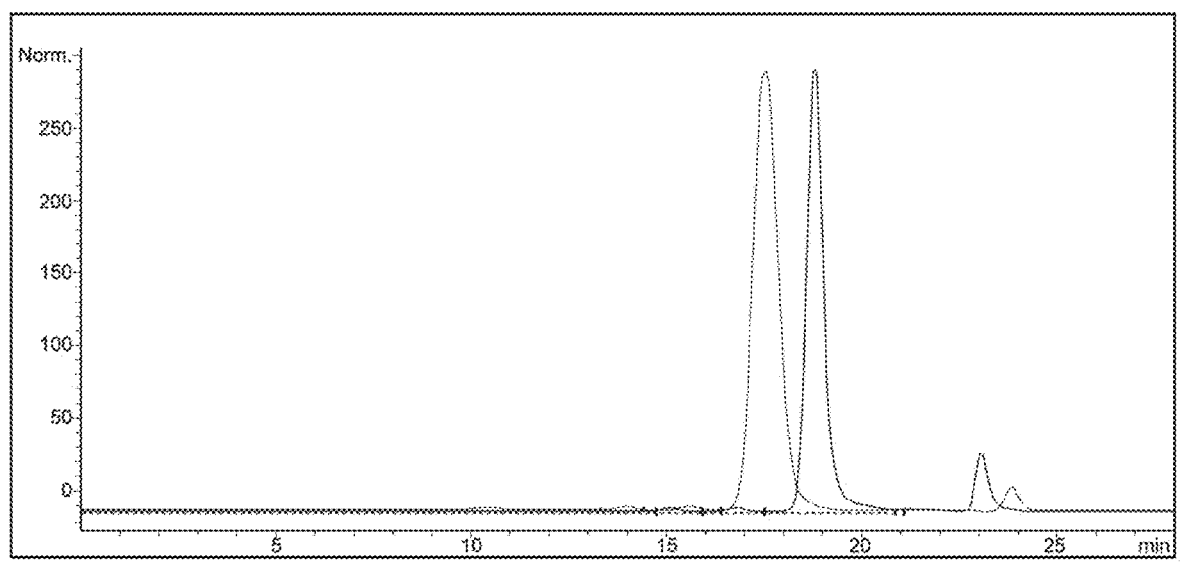
(FIG. 2A) SEC analysis of Example 2 (peak labelled "1") and Cetuximab-Fab (peak labelled "2")
Figure 2B:
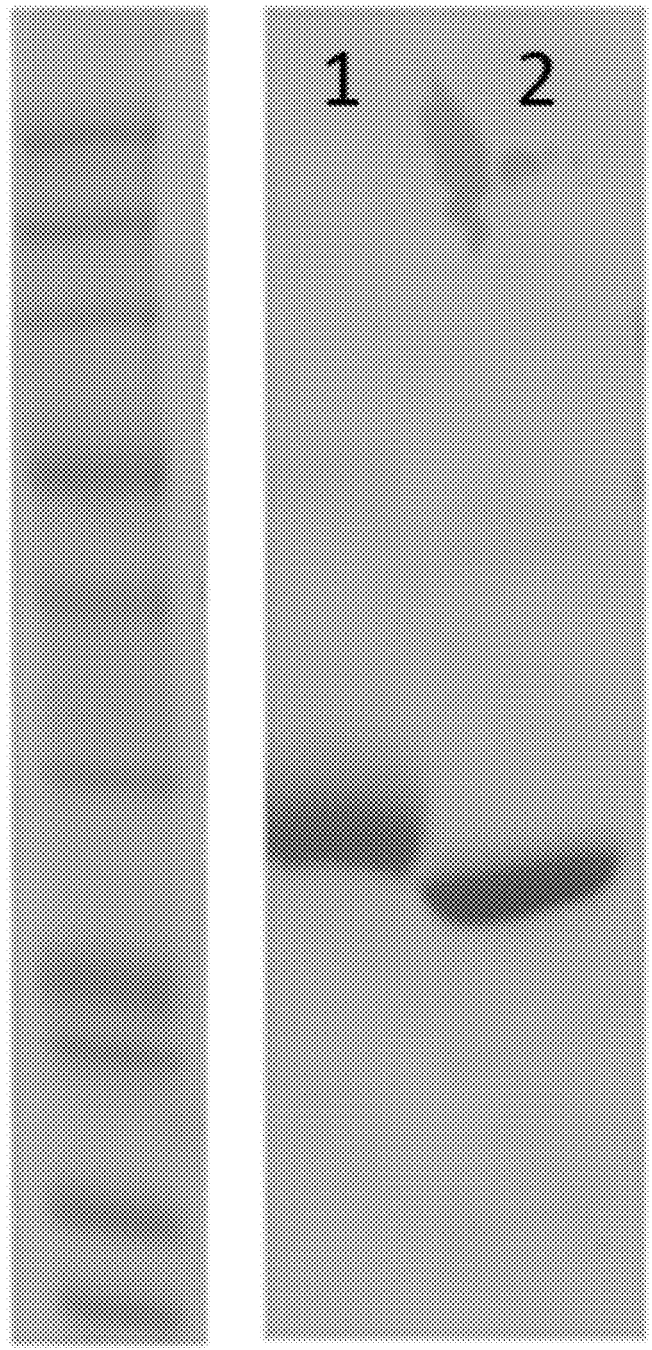
(FIG. 2B) SDS-PAGE analysis of Example 2 (lane 1) and Cetuximab-Fab (lane 2)
Figure 2C:
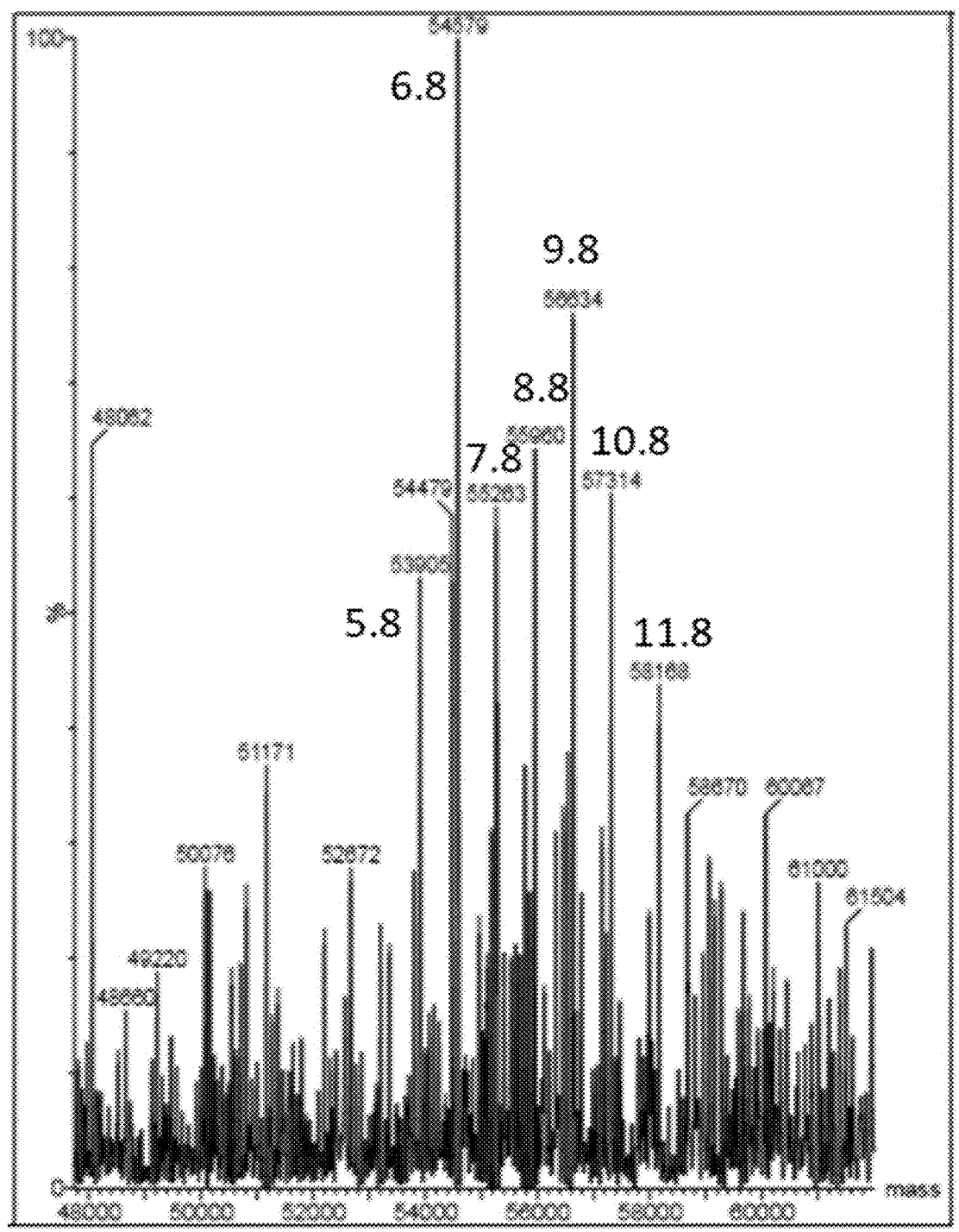
(FIG. 2C) MS analysis of Example 2.

SEC Analysis: Rt=17.54 minutes, 98.3% monomer content (FIGS. 2A-2C).

Example 3

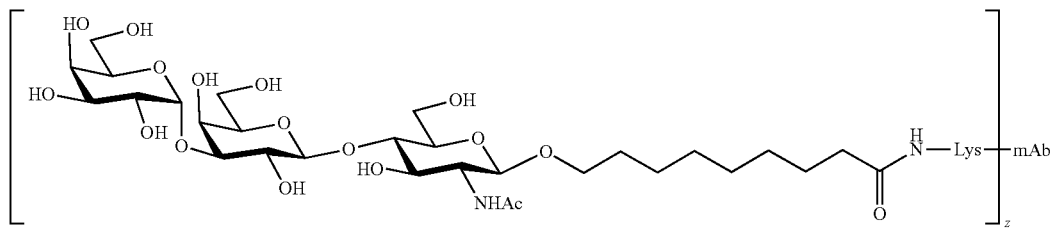

Example 3 was prepared according to the General Lysine Conjugation Method using 40 equivalents of Preparation 1 and cetuximab.

Estimated Av. LAR: z=12-18; Av. total no of alpha-Gal units: 12-18

Figure 3A:
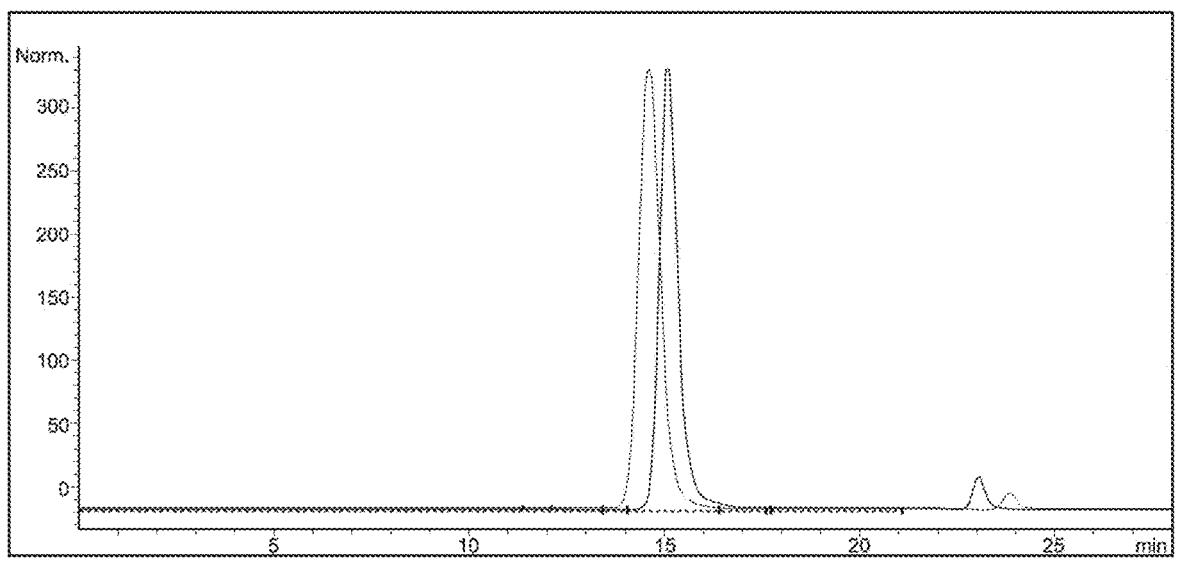
(FIG. 3A) SEC analysis of Example 3 (peak labelled "1") and Cetuximab (peak labelled "2")
Figure 3B:
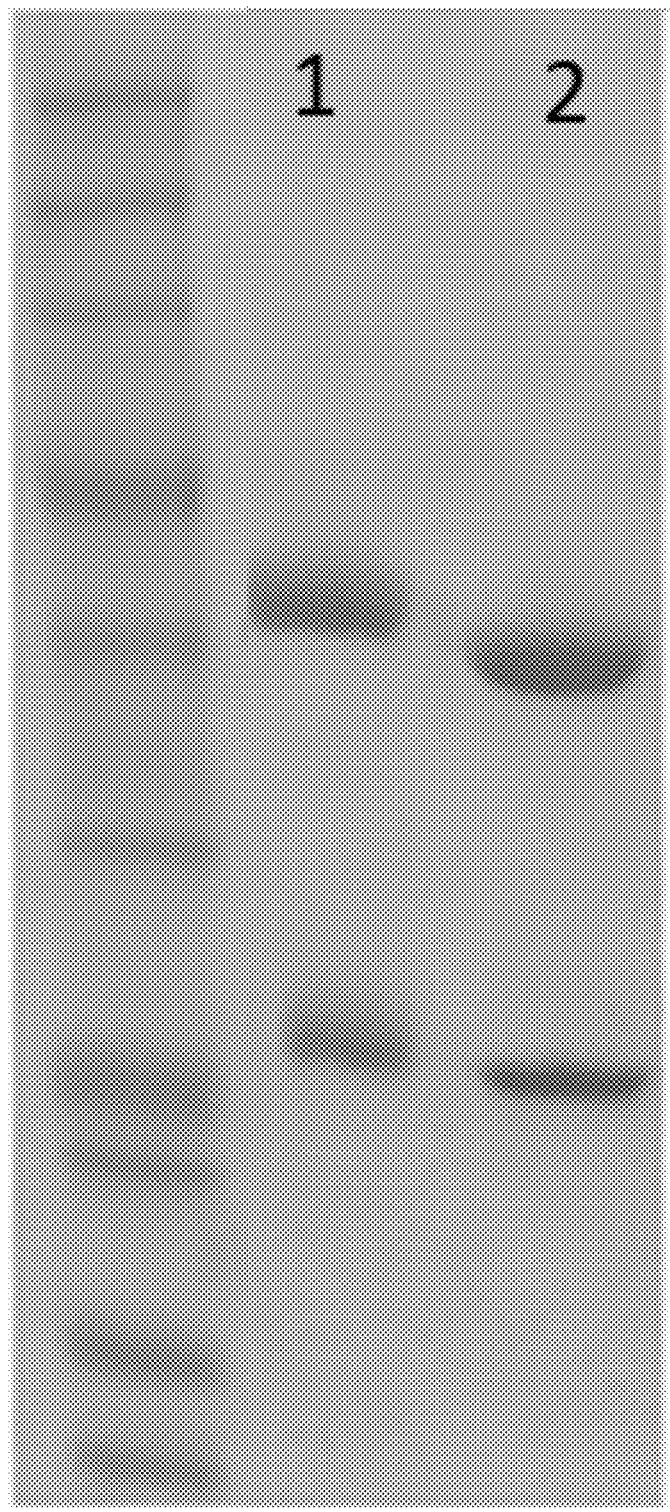
(FIG. 3B) SDS-PAGE analysis of Example 3 (lane 1) and Cetuximab (lane 2).

SEC Analysis: Rt=14.60 minutes, 99.7% monomer content (FIGS. 3A-3C).

Example 4

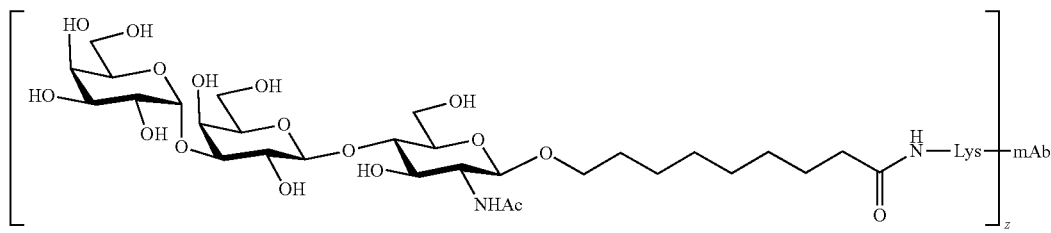

Example 4 was prepared according to the General Lysine Conjugation Method using 60 equivalents of Preparation 1 (with 20% v/v DMF) for 2 hours followed by a further 40 eq of Preparation 1 (with 4% v/v DMF) for 2 hours.

Figure 4A:
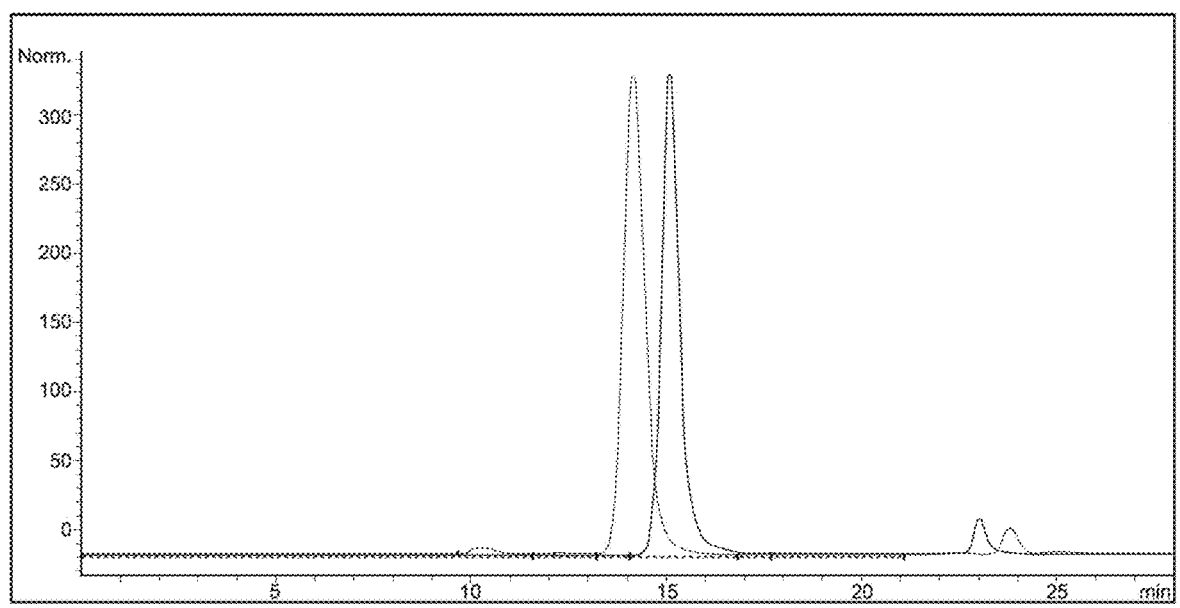
(FIG. 4A) SEC analysis of Example 4 (peak labelled "1") and Cetuximab (peak labelled "2")
Figure 4B:
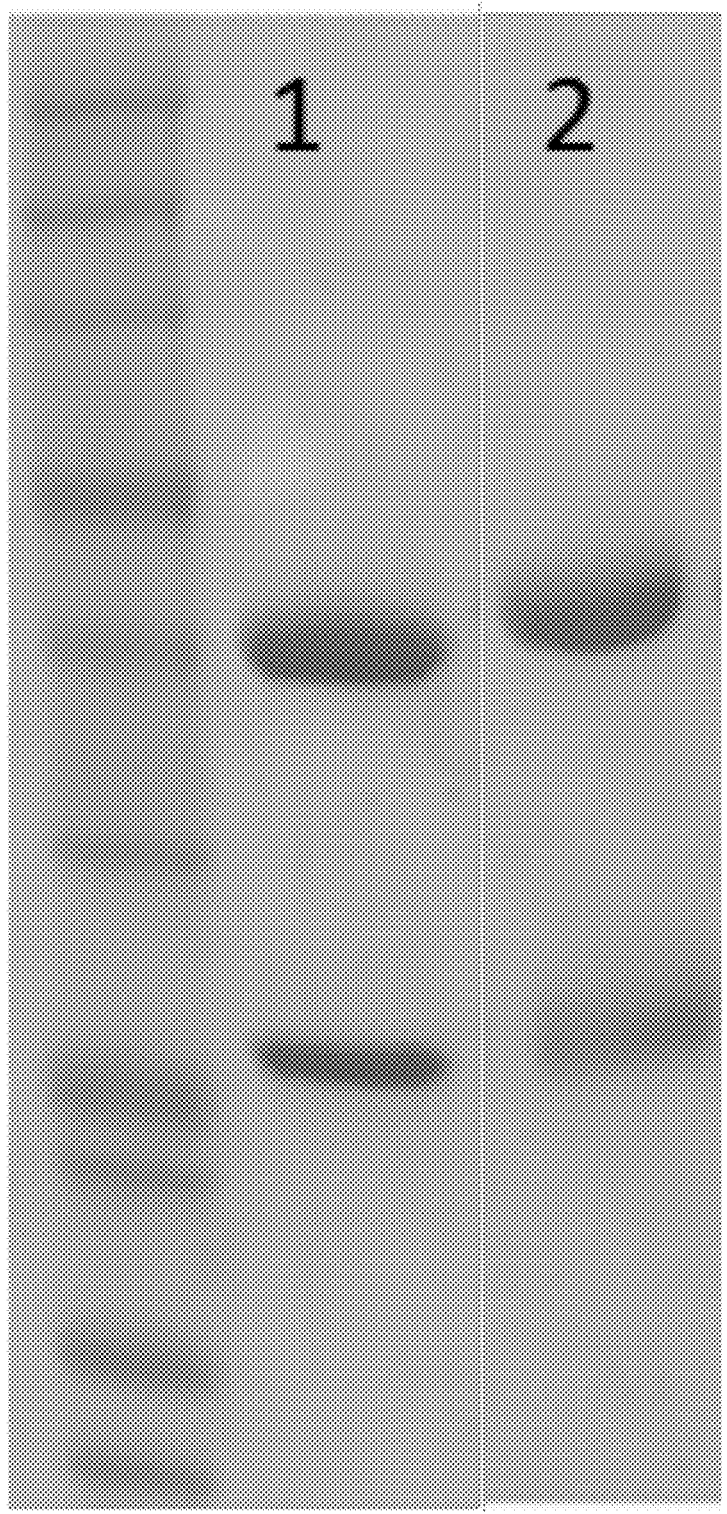
(FIG. 4B) SDS-PAGE analysis of Example 4 (lane 2) and Cetuximab (lane 1).

Estimated Av. LAR: n=18+; Av. total no of alpha-Gal units: 18+SEC Analysis: Rt=14.16 minutes, 99.7% monomer content (FIGS. 4A-4B).

Example 5

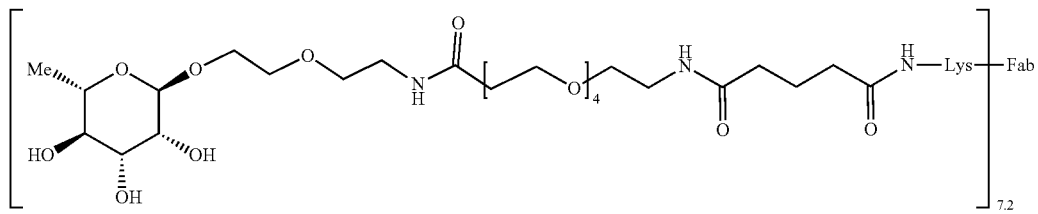

Example 5 was prepared according to the General Lysine Conjugation Method using 20 equivalents of Preparation 2 and cetuximab-Fab.

Av. LAR: 7.2; Av. total no of alpha-Gal units: 7.2

Figure 5A:
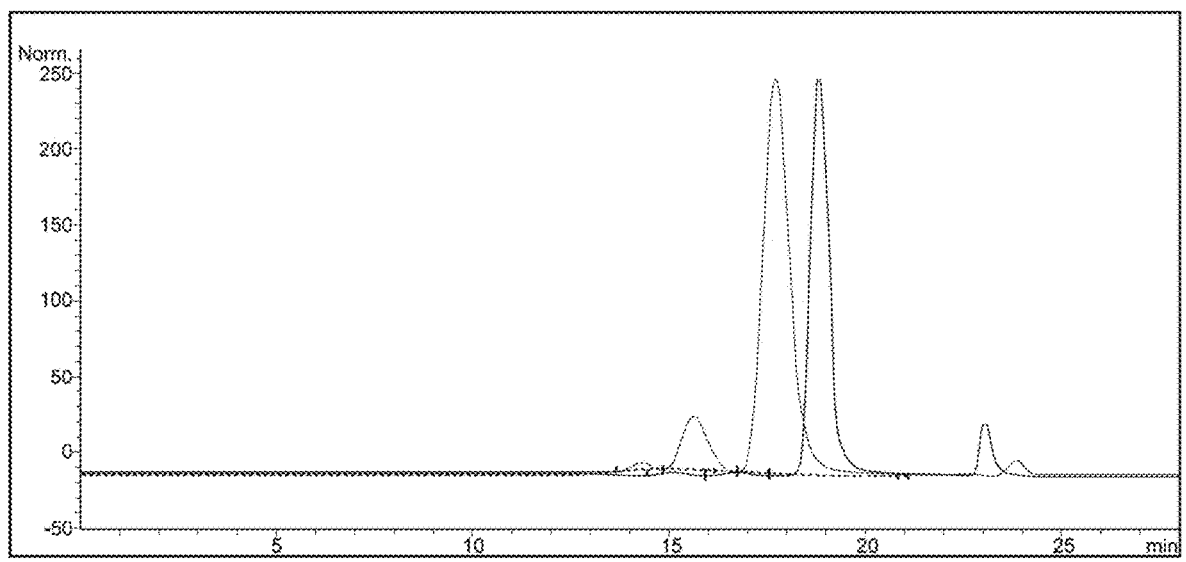
(FIG. 5A) SEC analysis of Example 5 (peak labelled "1") and Cetuximab-Fab (peak labelled "2")
Figure 5B:
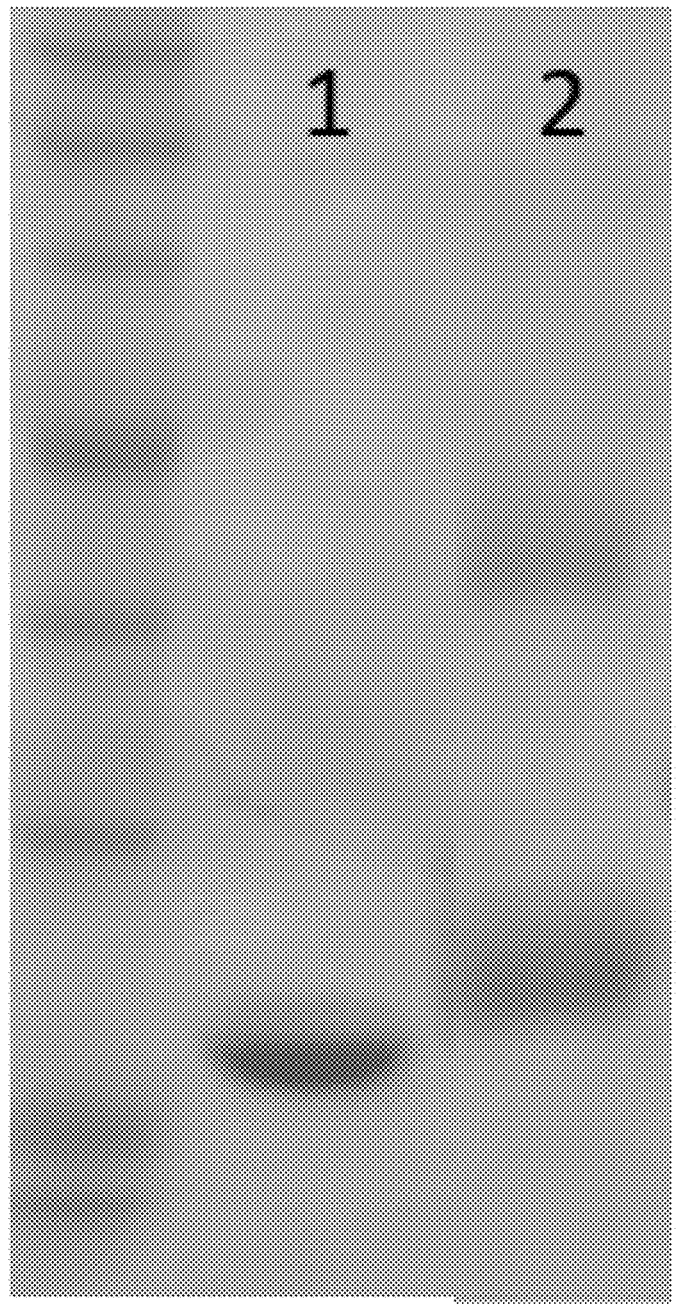
(FIG. 5B) SDS-PAGE analysis of Example 5 (lane 2) and Cetuximab-Fab (lane 1)
Figure 5C:
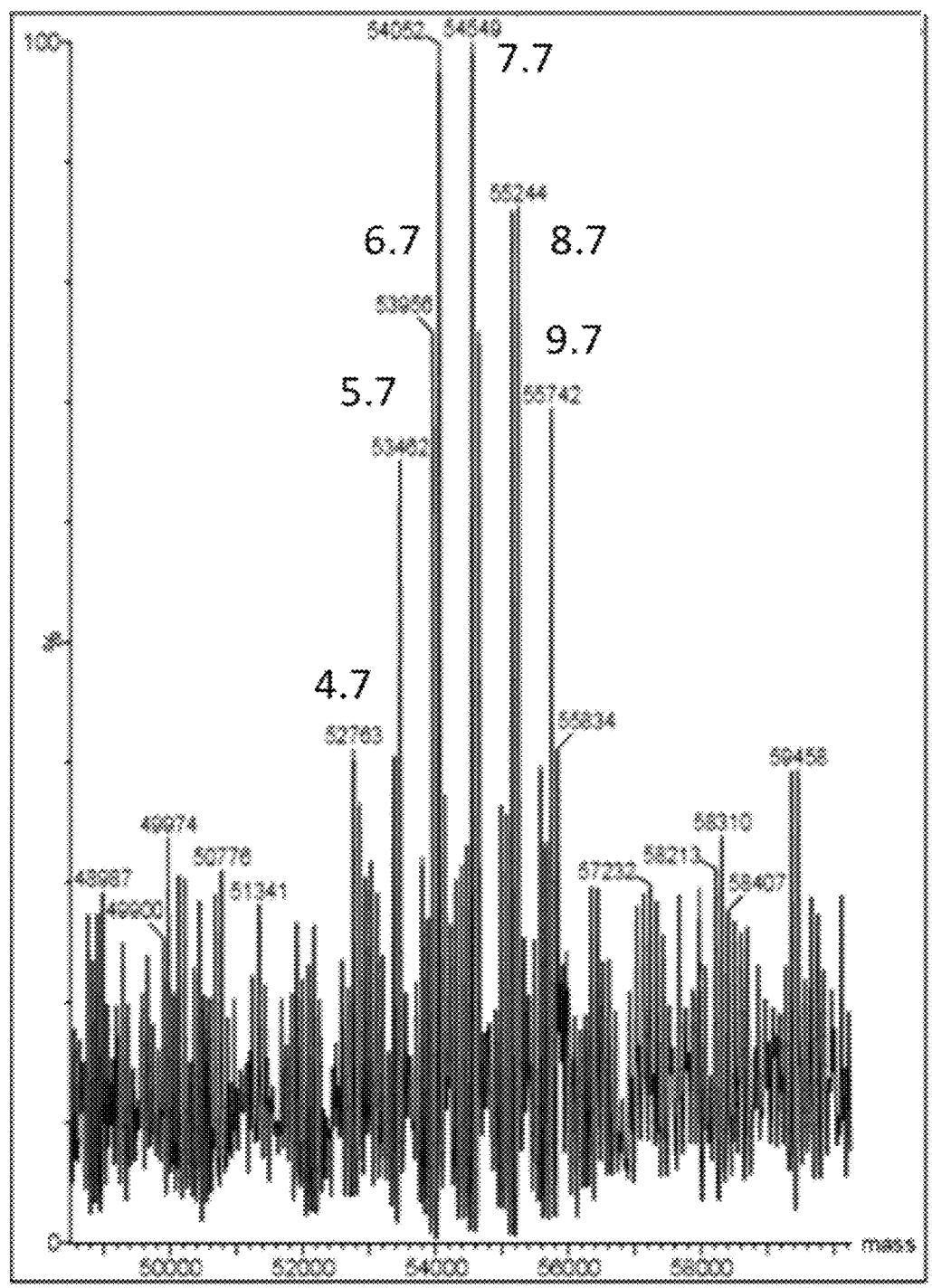
(FIG. 5C) MS analysis of Example 5.

SEC Analysis: Rt=17.704 minutes, 85.7% monomer content (FIGS. 5A-5C).

Example 6

Example 6 was prepared according to the General Lysine Conjugation Method using 40 equivalents of Preparation 2 and cetuximab.

Estimated Av. LAR: z=12+; Av. total no of alpha-Gal units: 12

Figure 6A:
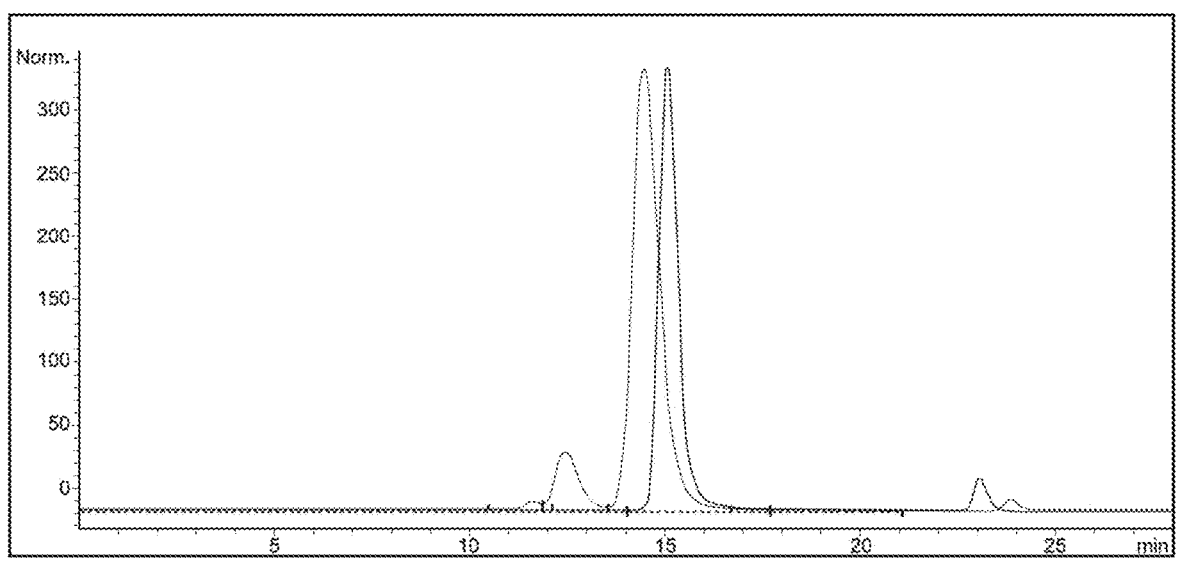
(FIG. 6A) SEC analysis of Example 6 (peak labelled "1") and Cetuximab (peak labelled "2")
Figure 6B:
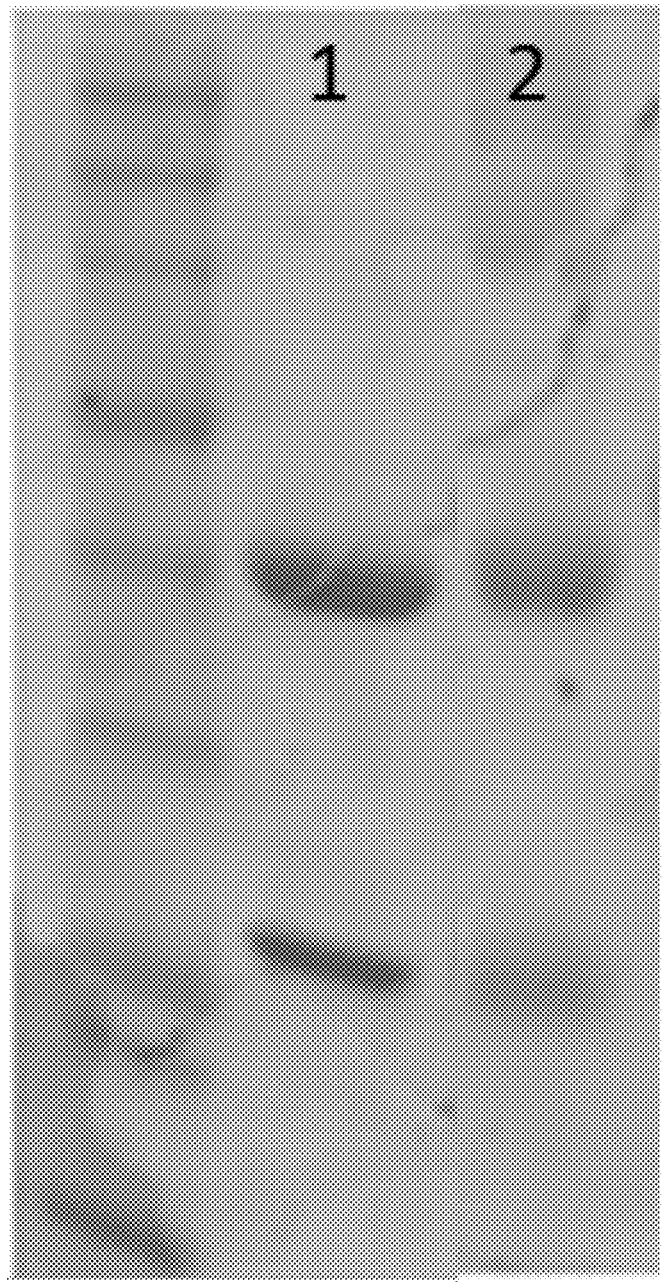
(FIG. 6B) SDS-PAGE analysis of Example 6 (lane 2) and Cetuximab (lane 1).

SEC Analysis: Rt=14.47 minutes, 88.4% monomer content (FIGS. 6A-6B).

Prophetic Examples

Variation of the loading for Examples 1-6 may be effected by altering the numbers of equivalents of linker-NHS or linker-Mal as required. Further examples include LAR ranges from 2 to 20 depending on using 2-60 equivalents of desired linker as described above. Alternatively, PEG 4 may be extended to PEG 12 and substituted in the Preparations described above.

Biological Assays

Flow Cytometry Assay Using Alpha-Galactosyl lgG Antibodies

Flow cytometry was used to demonstrate binding of the compound to the EGFR receptor on a human cell line (as cetuximab) and recruitment of the human alpha-galactosyl antibody. A431 cells are used to capture the EGFR binding mAb (cetuximab) as it is well known that the cells significantly over-express the EGFR receptor. Human IVIG, an anti-Gal IgG antibody, and phycoerythrin (PE) labelled

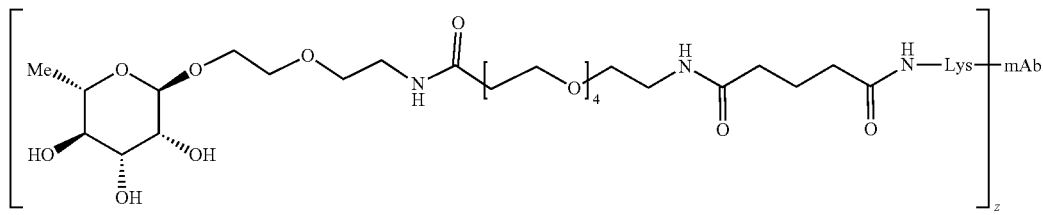

alpha-galactosyl IgG antibodies were used to detect binding of the compound to the cell line.

A431 cells (ATCC CRL-1555) were harvested and resuspended at 5×10⁶ cells/mL in phosphate buffered saline (PBS) (Sigma D8537). 2.5×10⁵ cells were then incubated with compound at 100 nM (top dose), buffer alone or 100 nM Cetuximab/Cetuximab Fab Fragment at room temperature, shaking at 450 rpm for 1 hour. The cells were washed with 200 μL PBS (Sigma D8662)+0.1% BSA (Bovine Serum Albumin-Sigma A2153), prior to adding 50 μL of hIVIG anti-Gal IgG (50 μg/ml) (Rockland Ab) in PBS+0.1% BSA and incubating at 4° C. for 30 min.

The cells were washed with 200 μL PBS+0.1% BSA, prior to adding 100 μL of secondary anti-lgG-PE (clone HP6017, Biolegend 409304). The cells were incubated at 4° C. for 30 minutes in dark.

After a final wash of 200 μL PBS+0.1% BSA the cells were resuspended in 100 μL PBS+0.1% BSA and evaluated on a flow cytometer (CytoFLEX Beckman Coulter). Data from all samples were analysed in the FlowJo software package (Version 10, FlowJo, LLC).

FIGS. 8A-8D demonstrate the capture of anti-alpha galactosyl IgG antibodies to the cell surface using Examples 1 to 4, respectively. The shift in fluorescence intensity (PE) occurs due to the binding event at each end of the molecule.

Figure 9A:
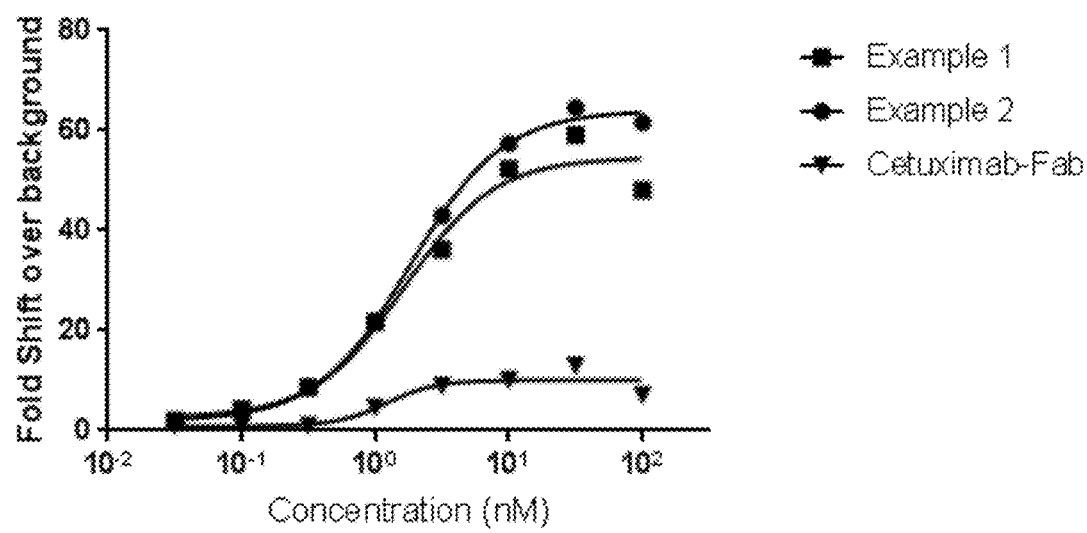
FIG. 9: Demonstrates the level of the compound recruitment of anti-Gal IgG for Examples 1-4, (FIGS. 9A-9D, respectively) compared with the unconjugated Fab fragment or cetuximab in dose response from 100 to 0 nM.
Figure 9B:
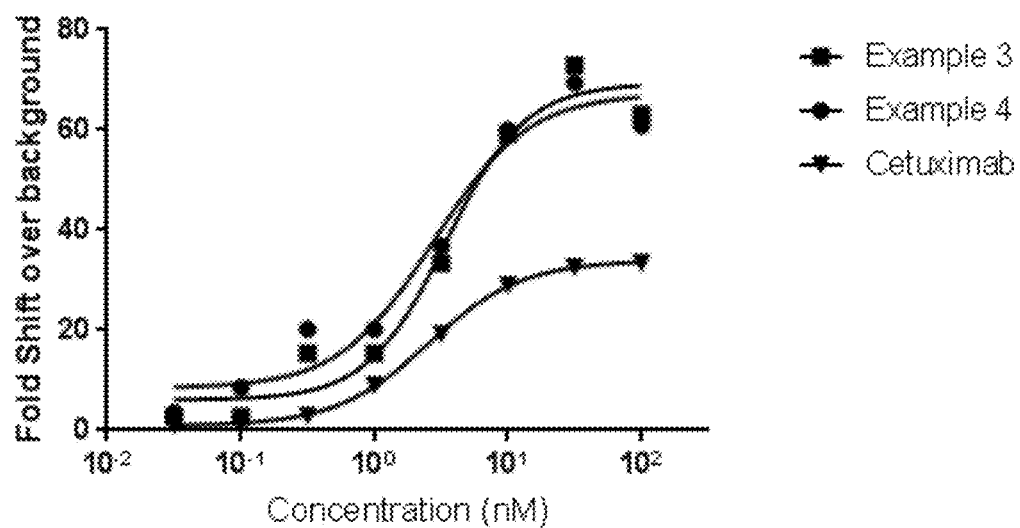
Figure 10A:
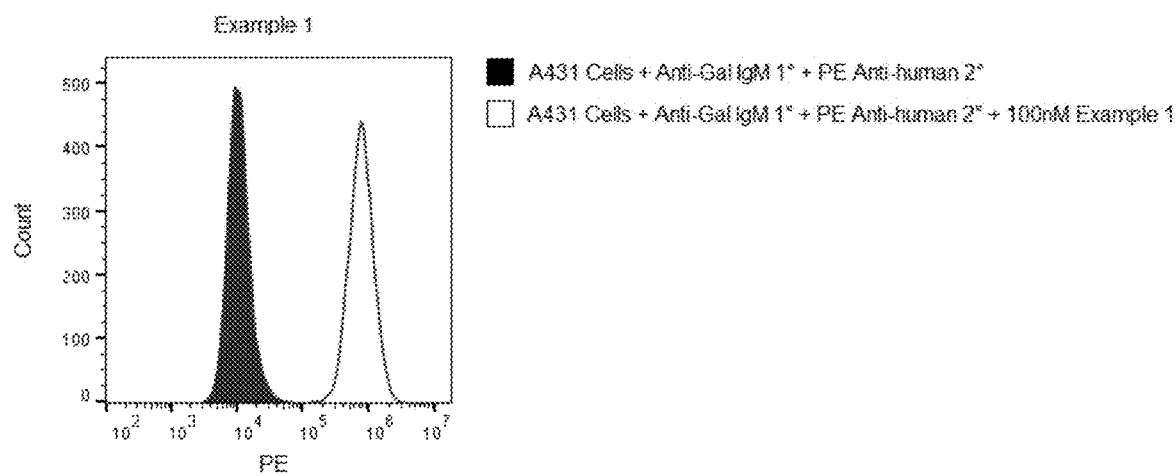
FIG. 10: Demonstrates the capture of anti-alpha galactosyl IgM antibodies to the cell surface using Examples 1-4, (FIGS. 10A-10D, respectively). The shift in fluorescence intensity (PE) occurs due to the binding event at each end of the molecule.
Figure 10B:
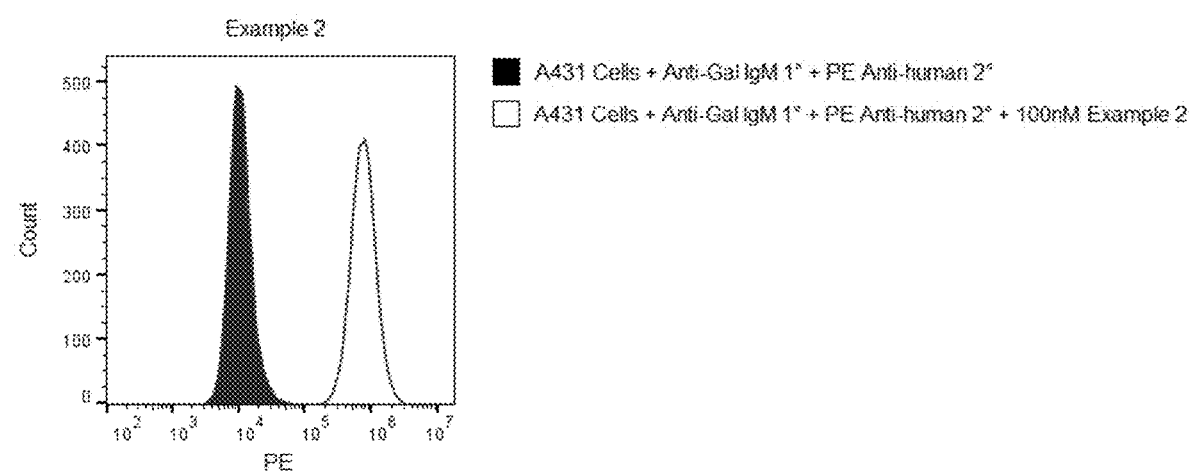
Figure 10C:
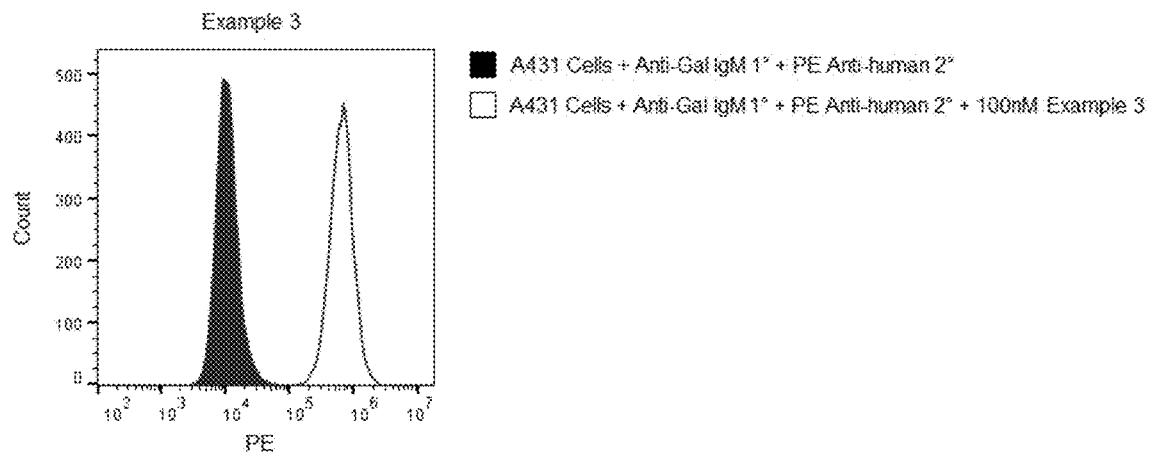
Figure 10D:
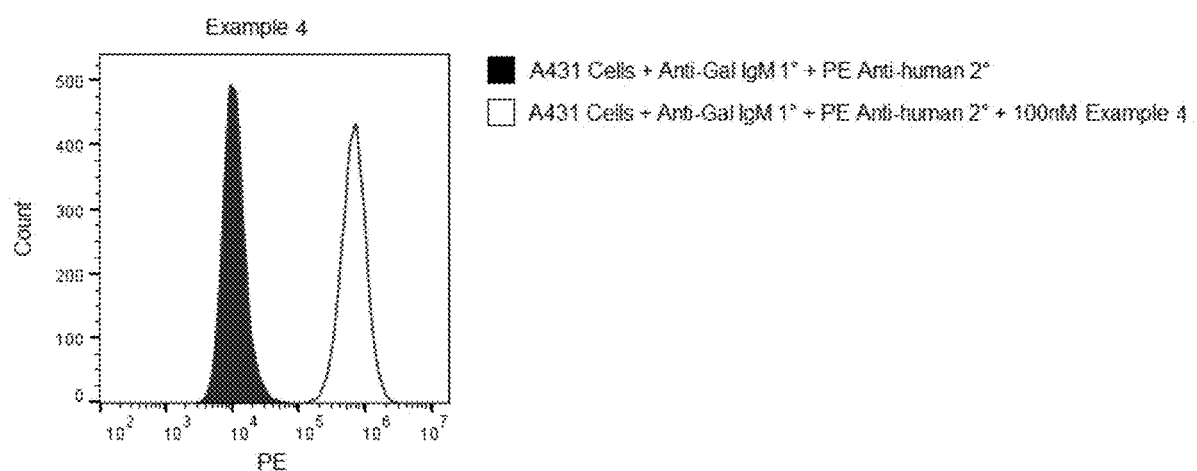

FIGS. 9A and 9B demonstrate the level of the compound recruitment of anti-Gal IgG for Examples 1-2 (FIG. 9A) and 3-4 (FIG. 9B) compared with the unconjugated Fab fragment or cetuximab in dose response from 100 to 0 nM. The results in FIGS. 9A and 9B demonstrate the dose related, compound driven recruitment of anti-Gal IgG antibodies to A431 cells for Examples 1~4 compared to cetuximab and cetuximab-Fab where minimal recruitment is observed.

Flow Cytometry Assay Using Alpha-Galactosyl IgM Antibodies

Flow cytometry was used to demonstrate binding of compound (anti-EGFR specific, as cetuximab) to an EGFR receptor on a human cell line and recruitment of the human alpha-galactosyl antibody.

A431 cells are used to capture the EGFR binding mAb (cetuximab) as it is well known that the cells significantly over-express the EGFR receptor. M86 IgM and phycoerythrin (PE) labelled alpha-galactosyl IgG antibodies were used to detect binding of the compound.

A431 cells (ATCC CRL-1555) were harvested and resuspended at 5×10⁶ cells/mL in phosphate buffered saline (PBS) (Sigma D8537). 2.5×10⁵ cells were then incubated with compound at 100 nM (top dose), buffer alone or 100 nM Cetuximab/Cetuximab Fab Fragment at room temperature, shaking at 450 rpm for 1 hour. The cells were washed with 150 μL PBS (Sigma D8662)+0.1% BSA (Bovine Serum Albumin-Sigma A2153), prior to adding 50 μL of anti-Gal M86 IgM (Absolute Ab Ab00532-15.0) (15.6 μg/ml) in PBS+0.1% BSA and incubating at 4° C. for 30 minutes.

The cells were washed with 150 μL PBS+0.1% BSA, prior to adding 100 μL of secondary anti-IgM-PE Ab (Clone MHM-88, Biolegend 314508). The cells were incubated at 4° C. for 30 minutes in dark.

After a final wash of 150 μL PBS+0.1% BSA the cells were resuspended in 100 μL PBS+0.1% BSA and evaluated on a flow cytometer (CytoFLEX Beckman Coulter). Data from all samples were analysed in the FlowJo software package (Version 10, FlowJo, LLC).

FIGS. 10A-10D demonstrate the capture of anti-alpha galactosyl IgM antibodies to the cell surface using Examples 1-4, respectively. The shift in fluorescence intensity (PE) occurs due to the binding event at each end of the molecule.

Figure 11A:
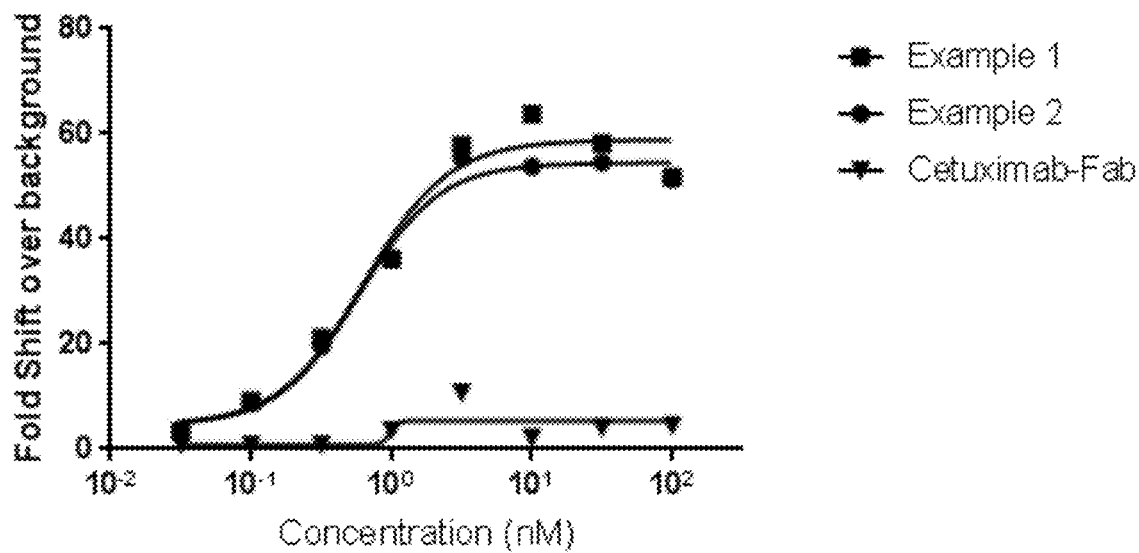
FIG. 11: Demonstrates the level of the compound recruitment of anti-Gal IgM for Examples 1-2, (FIG. 11A) and Examples 3-4 (FIG. 11B) compared with the unconjugated Fab fragment or cetuximab in dose response from 100 to 0 nM.
Figure 11B:
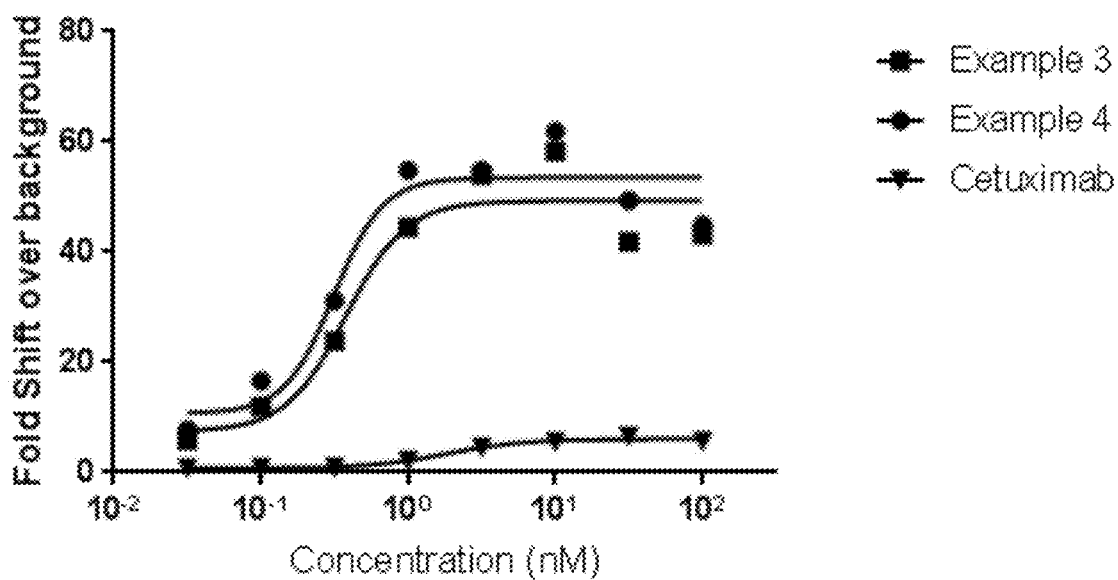

FIGS. 11A and 11B demonstrate the level of the compound recruitment of anti-Gal IgM for Examples 1-2 (FIG. 11A) and 3-4 (FIG. 11B) compared with the unconjugated Fab fragment or cetuximab in dose response from 100 to 0 nM. The results in FIG. 11 demonstrate the dose related, compound driven recruitment of anti-Gal IgM antibodies to A431 cells for Examples 1~4 compared to cetuximab and cetuximab-Fab where minimal recruitment is observed.

Flow Cytometry Assay Using Rhamnose lgG Antibodies

Flow cytometry was used to demonstrate binding of the compound to the EGFR receptor on a human cell line (as cetuximab) and recruitment of the human rhamnose antibody.

A431 cells are used to capture the EGFR binding mAb (cetuximab) as it is well known that the cells significantly over-express the EGFR receptor. An anti-rhamnose IgG antibody, and phycoerythrin (PE) labelled alpha-galactosyl IgG antibodies were used to detect binding of the compound to the cell line.

A431 cells (ATCC CRL-1555) were harvested and resuspended at 5×10⁶ cells/mL in phosphate buffered saline (PBS) (Sigma D8537). 2.5×10⁵ cells were then incubated with compound at 100 nM (top dose), buffer alone or 100 nM Cetuximab/Cetuximab Fab Fragment at room temperature, shaking at 450 rpm for 1 hour. The cells were washed with 150 μL PBS (Sigma D8662)+0.1% BSA (Bovine Serum Albumin-Sigma A2153), prior to adding 50 μL of anti-Rhamnose IgG (50 μg/ml) (Rockland Ab) in PBS+0.1% BSA and incubating at 4° C. for 30 minutes.

The cells were washed with 150 μL PBS+0.1% BSA, prior to adding 100 μL of secondary anti-lgG-PE (clone HP6017, Biolegend 409304). The cells were incubated at 4° C. for 30 minutes in dark.

After a final wash of 150 μL PBS+0.1% BSA the cells were resuspended in 100 μL PBS+0.1% BSA and evaluated on a flow cytometer (CytoFLEX Beckman Coulter). Data from all samples were analysed in the FlowJo software package (Version 10, FlowJo, LLC).

Figure 12A:
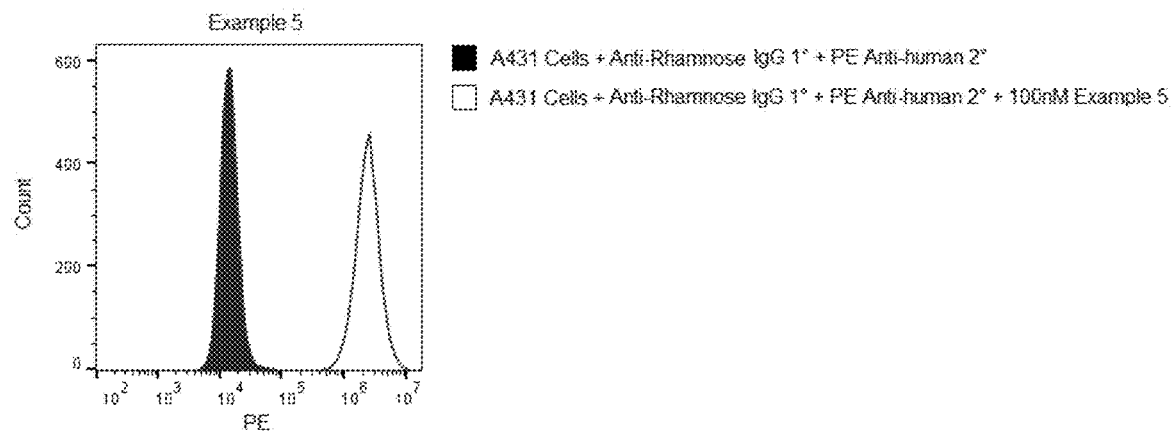
FIG. 12: Demonstrates the capture of anti-rhamnose IgG antibodies to the cell surface using Examples 5 (FIG. 12A) and 6 (FIG. 12B). The shift in fluorescence intensity (PE) occurs due to the binding event at each end of the molecule.
Figure 12B:
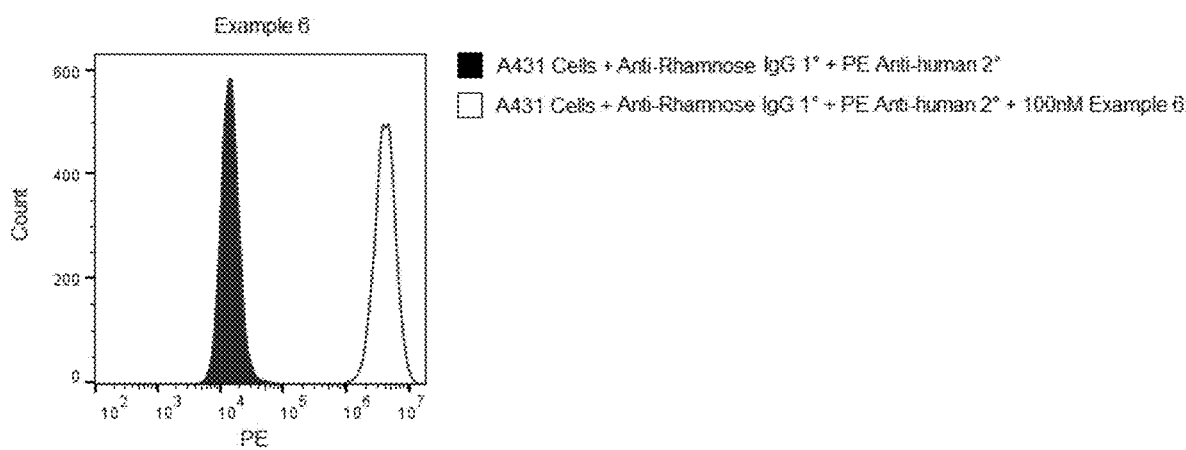

FIGS. 12A and 12B demonstrate the capture of anti-rhamnose IgG antibodies to the cell surface using Examples 5 and 6, respectively. The shift in fluorescence intensity (PE) occurs due to the binding event at each end of the molecule.

Figure 13A:
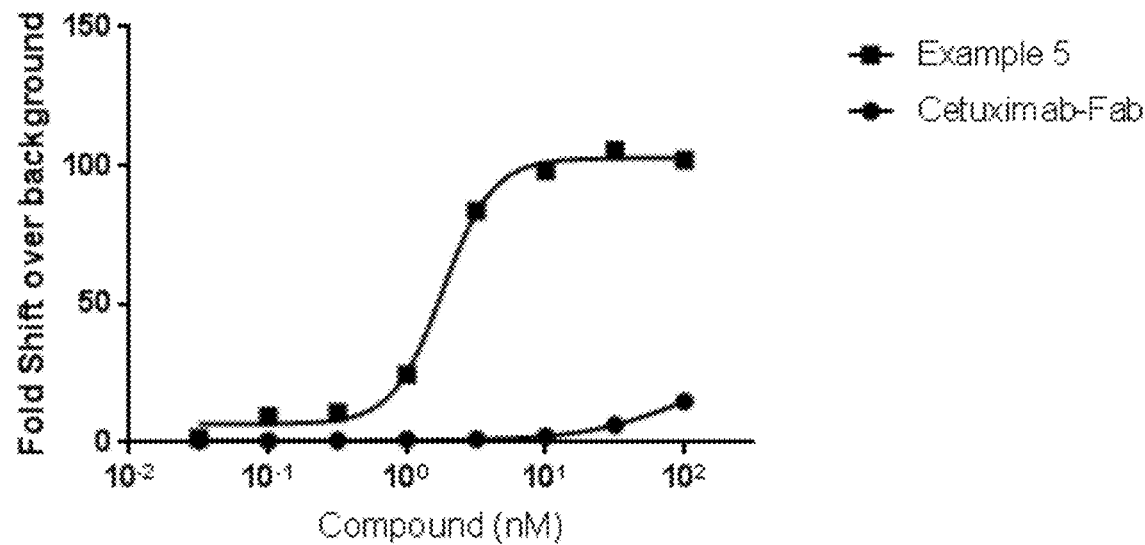
FIG. 13: Demonstrates the level of the compound recruitment of anti-rhamnose IgG for Examples 5 (FIG. 13A) and 6 (FIG. 13B) compared with the unconjugated Fab fragment or cetuximab in dose response from 100 to 0 nM.
Figure 13B:
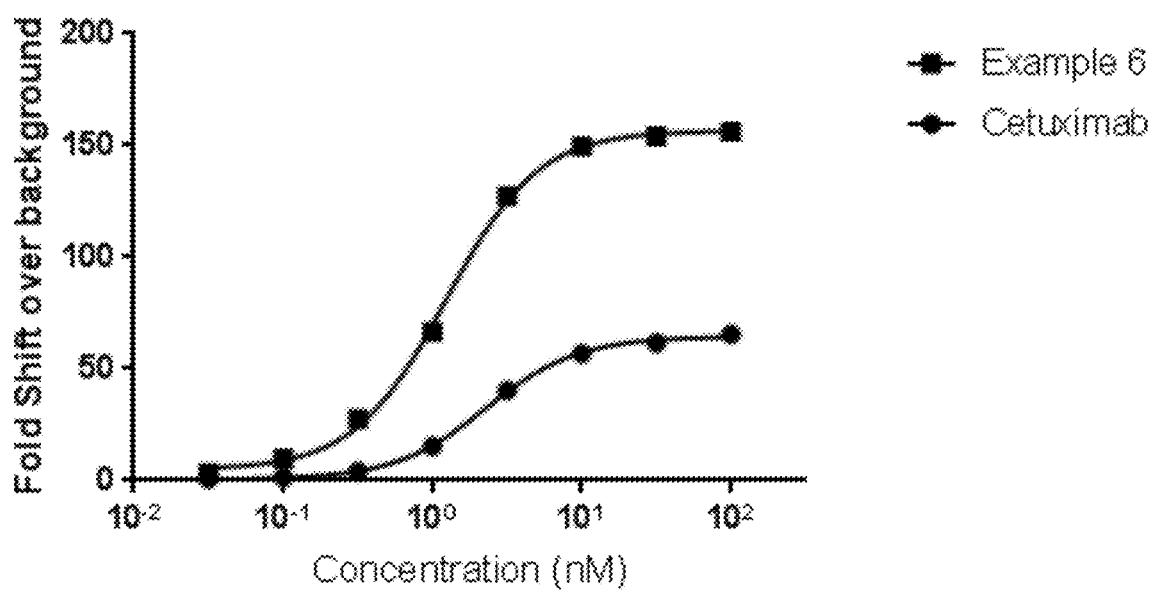
Figure 14A:
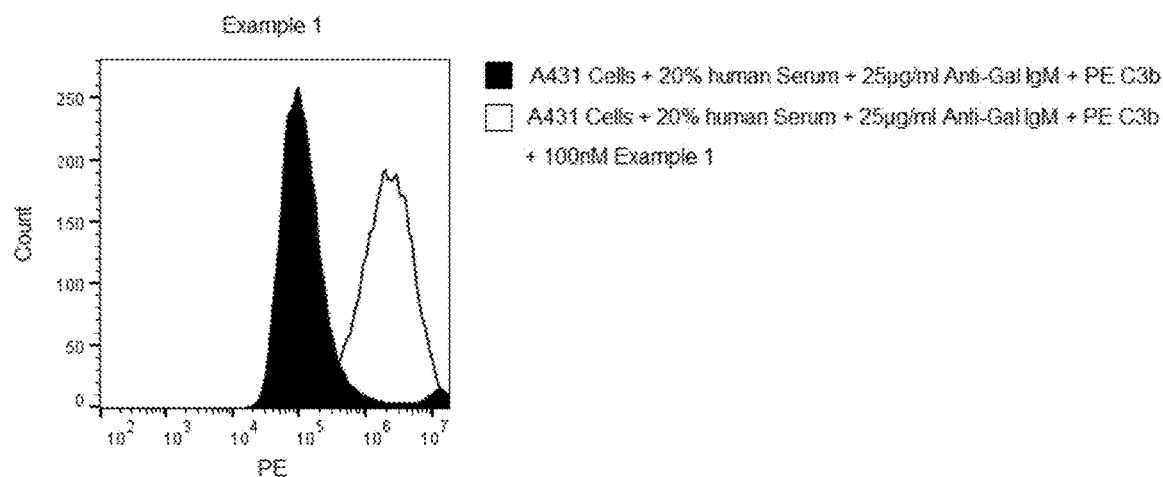
FIG. 14: Demonstrates the level of C3b deposition on A431 using Examples 1 to 4, (FIGS. 14A-14D, respectively).
Figure 14B:
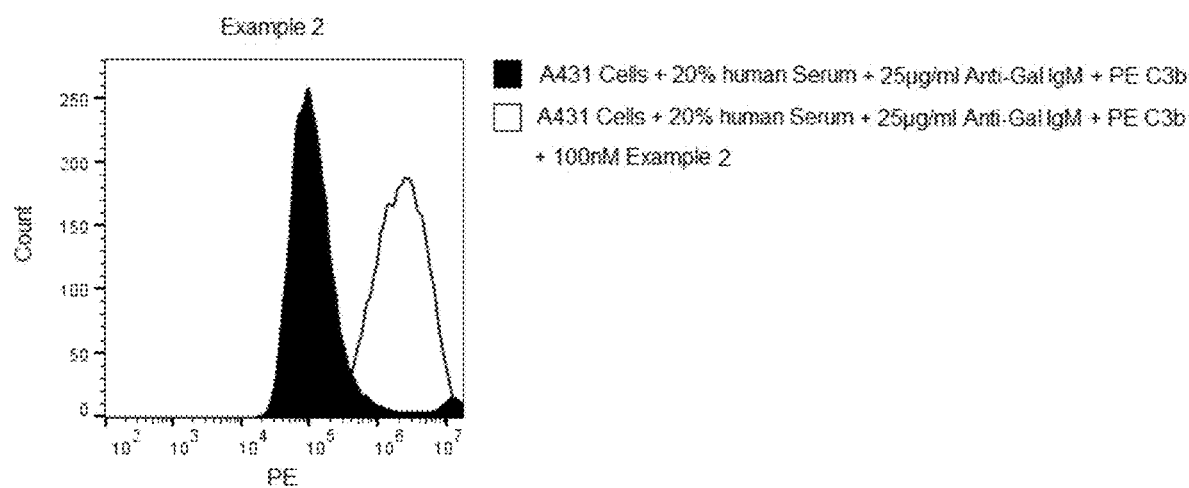
Figure 14C:
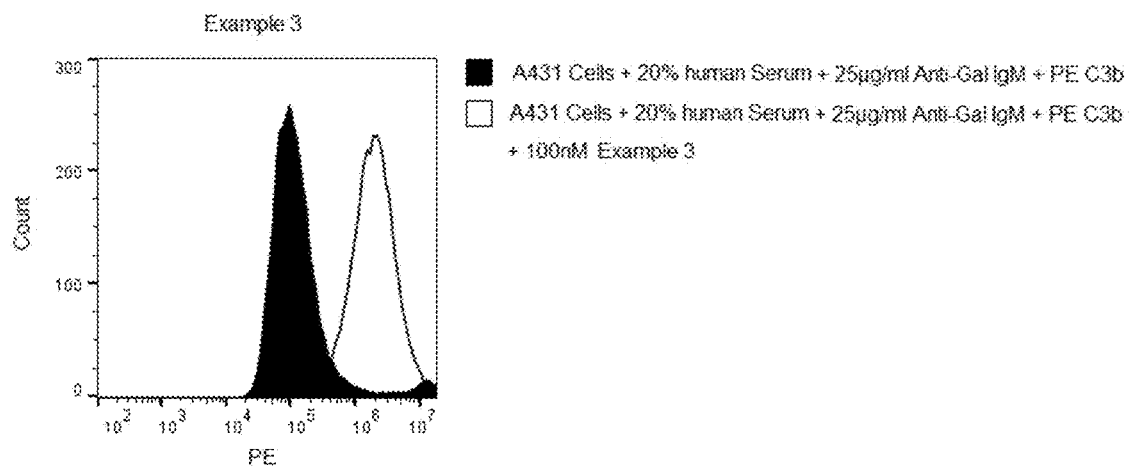
Figure 14D:
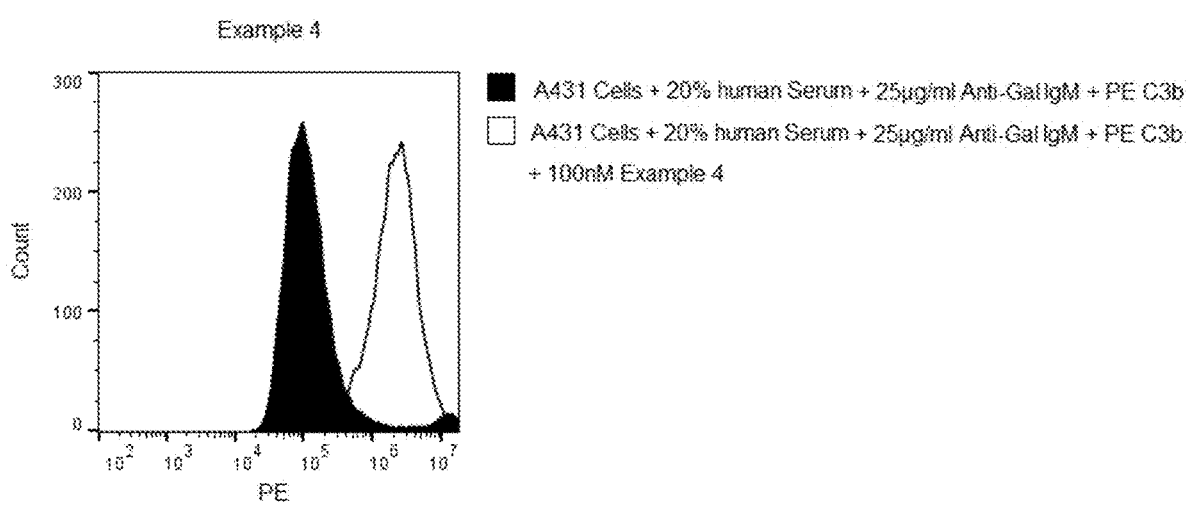

FIGS. 13A and 13B demonstrate the level of the compound recruitment of anti-rhamnose lgG for Examples 5 and 6, respectively, compared with the unconjugated Fab fragment or cetuximab in dose response from 100 to 0 nM. The results in FIG. 13 demonstrate the dose related, compound driven recruitment of anti-Rhamnose IgG antibodies to A431 cells for Examples 5 and 6 compared to cetuximab and cetuximab-Fab where minimal recruitment is observed.

Flow Cytometry Assay Using c3b Antibodies

Flow cytometry was used to demonstrate binding of the compounds to a cell line of interest and recruitment of the C3b complement component to the cell and subsequent cell viability. A431 cells are used to capture the EGFR binding mAb (cetuximab) or antibody fragment, as it is well known that the cells significantly over-express the EGFR receptor. Anti-C3b antibody conjugated to phycoerythrin (PE) was used to detect recruitment of C3b molecules to cells from serum after addition of the compounds at various concentrations. The addition of SYTOX Blue also allows for evaluation of the cell viability after addition of the compounds at various concentrations.

A431 cells (ATCC CRL-1555) were harvested and resuspended at 5×10⁶ cells/mL in phosphate buffered saline (PBS)

(Sigma D8537). 5×10⁵ cells were then incubated with compound at 100 nM (top dose), buffer alone or 100 nM (top dose) Cetuximab/Cetuximab Fab Fragment at room temperature, shaking at 450 rpm for 1 hour. The cells were washed with 150 μL PBS (Sigma D8662)+0.1% BSA (Bovine Serum Albumin-Sigma A2153), prior to adding 100 μL PBS and 50 μL of 60% Human Serum (HS) (Patricell 23590) or Heat Inactivated Human Serum (HI HS) with 75 μg/ml M86 anti-Gal IgM (Absolute Antibody Ab00532.10.0) or 75 μg/ml of anti-Rhamnose IgG (Rockland Ab) and incubated at 37° C. for 30 minutes.

The cells were washed with 2×150 μL PBS+0.1% BSA, prior to adding 100 μL of anti-C3b-PE (Biolegend 846104). The cells were incubated at 4° C. for 30 minutes in dark.

After a final wash of 150 μL PBS+0.1% BSA the cells were resuspended in 100 μL PBS+0.1% BSA+1:1000 dilution of viability stain SYTOX Blue (Invitrogen S34857) and evaluated on a flow cytometer (CytoFLEX Beckman Coulter). Data from all samples were analysed in the FlowJo software package (Version 10, FlowJo, LLC).

FIGS. 14A-14D demonstrate the level of C3b deposition on A431 cells using Examples 1-4, respectively.

Figure 15A:
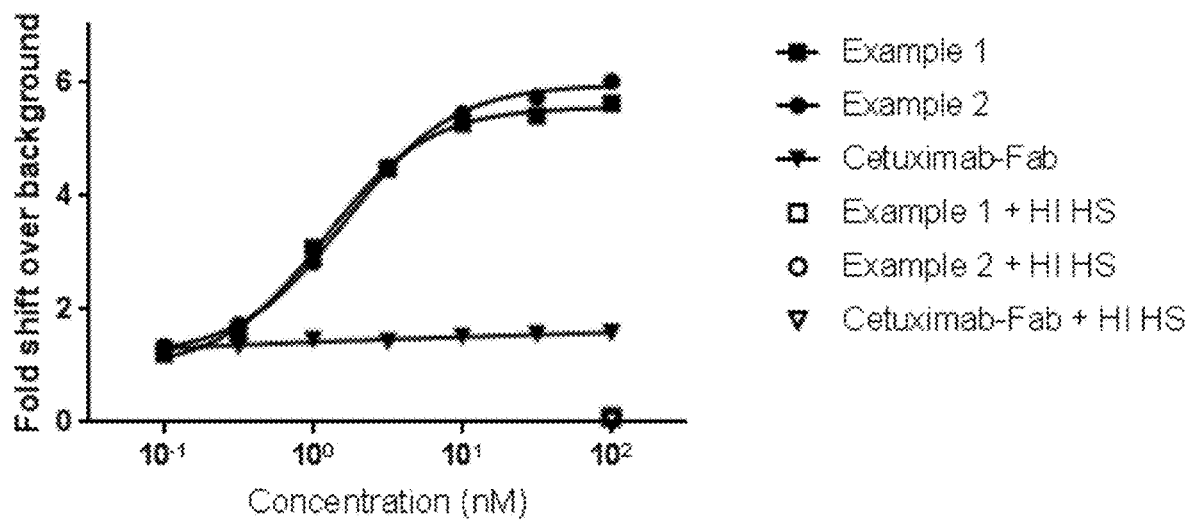
FIG. 15: Demonstrates the level of C3b deposition on A431 cells with varying concentrations of Examples 1-2 (FIG. 15A) and Examples 3-4 (FIG. 15B), compared to cetuximab Fab fragment and/or cetuximab.
Figure 15B:
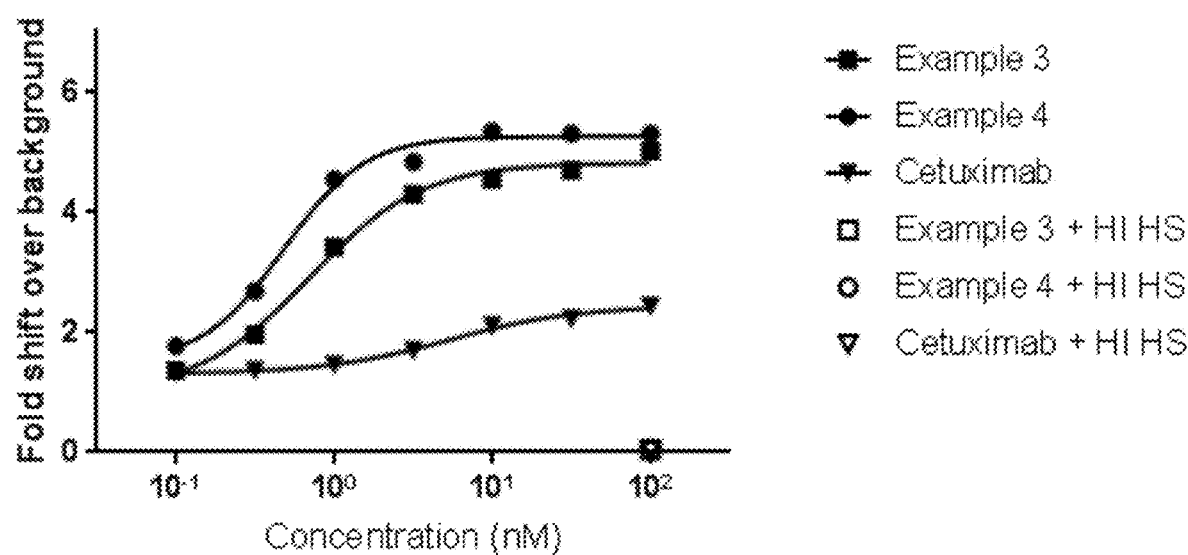

FIGS. 15A and 15B demonstrate the level of C3b deposition on A431 cells with varying concentrations of Examples 1-2 (FIG. 15A) and 3-4 (FIG. 15B), compared to cetuximab or cetuximab-Fab. The results in FIG. 15 demonstrate the dose-related level of C3b deposition observed for Examples 1-4. The data demonstrates that C3b deposition is much higher for Examples 1~4 when compared to cetuximab or cetuximab-Fab.

Figure 16A:
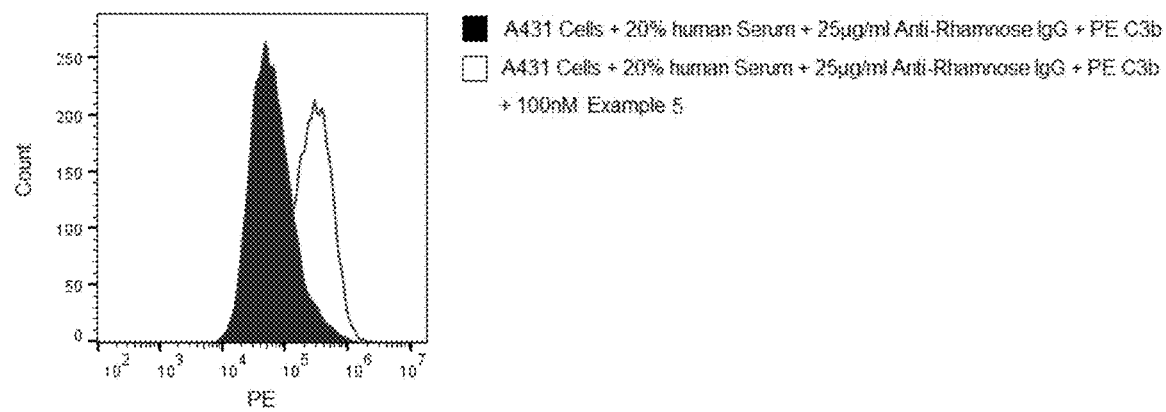
FIG. 16: Demonstrates the level of C3b deposition on A431 cells using Examples 5 (FIG. 16A) and 6 (FIG. 16B).
Figure 16B:
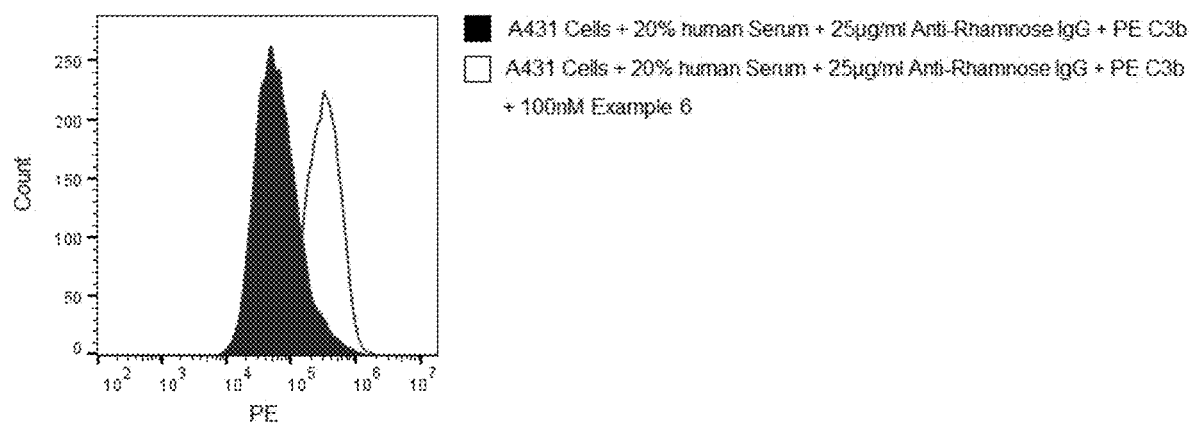

FIGS. 16A and 16B demonstrate the level of C3b deposition on A431 using Examples 5 and 6, respectively.

Figure 17A:
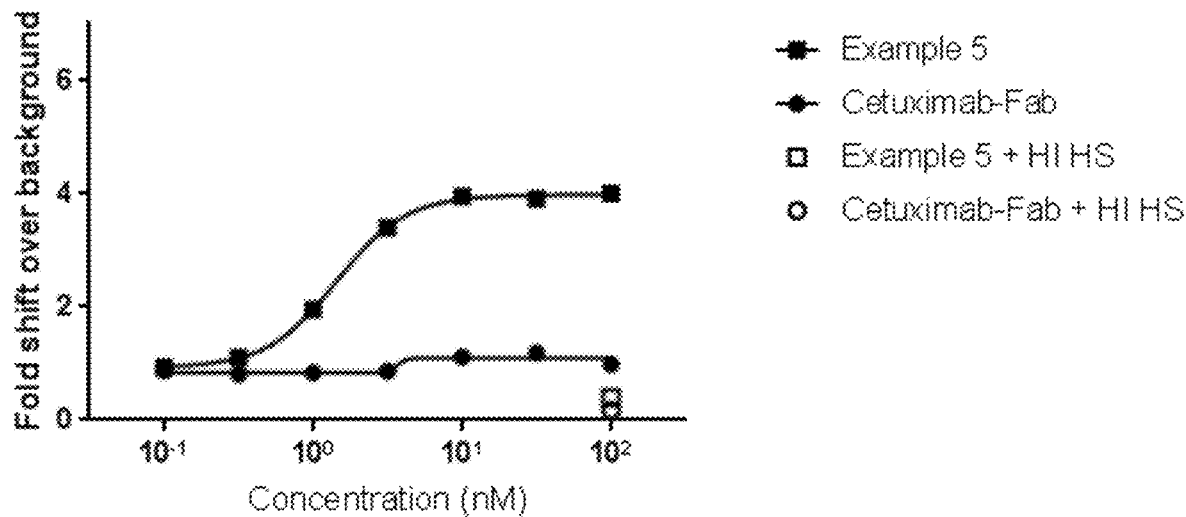
FIG. 17: Demonstrates the level of C3b deposition on A431 cells with varying concentrations of Examples 5 (FIG. 17A) and 6 (FIG. 17B), compared to cetuximab Fab fragment and/or cetuximab.
Figure 17B:
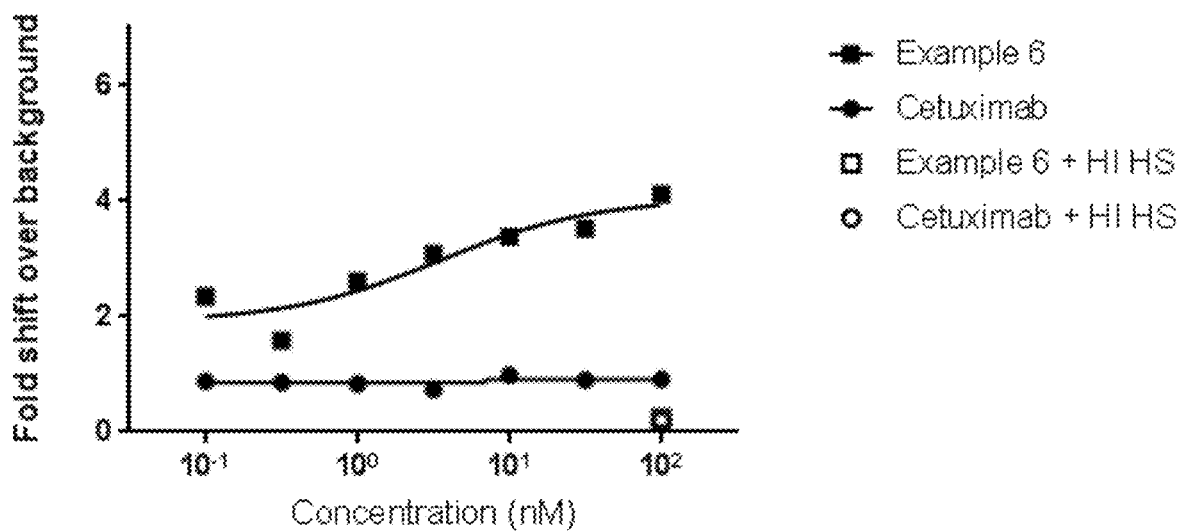

FIGS. 17A and 17B demonstrate the level of C3b deposition on A431 cells with varying concentrations of Examples 5 and 6, respectively, compared to cetuximab Fab fragment and/or cetuximab. The results in FIG. 17 demonstrate the dose-related level of C3b deposition observed for Examples 5 and 6. The data demonstrates that C3b deposition is much higher for Examples 5 and 6 when compared to cetuximab or cetuximab-Fab.

---

The invention claimed is:
1. A compound of formula (I) or a pharmaceutically acceptable salt thereof:

[F—S$_1$—X]$_z$-L  (I)

wherein:
F represents rhamnose or F represents a carbohydrate molecule that binds to a human anti-alpha-galactosyl antibody;
S$_1$ represents a spacer selected from a —(CH$_2$)$_a$— or —(CH$_2$)$_b$—(CH$_2$—CH$_2$—O)$_c$—(CH$_2$)$_d$— group, wherein one to ten of said —CH$_2$— groups may optionally be substituted by one or more groups selected from —O—, —S—, =N(H)—, —C(=O)—, —C(O) NH—, —NHC(O)—;
a represents an integer selected from 1 to 35;
b represents an integer selected from 0 to 10;
c represents an integer selected from 1 to 20;
d represents an integer selected from 1 to 20;
X represents an antibody or antigen binding fragment attachment moiety;
z is selected from 1 to 50; and
L represents a binding moiety selected from an antibody or antigen binding fragment thereof.

2. The compound as defined in claim 1, wherein S$_1$ represents a spacer selected from:
—(CH$_2$)$_a$— wherein one of said —CH$_2$— groups may optionally be substituted by one or more groups selected from —O—, —S—, =N(H)—, —C(=O)—, —C(O)NH— and —NHC(O)—; or
—(CH$_2$)$_b$—(CH$_2$—CH$_2$—O)$_c$—(CH$_2$)$_d$—, wherein one to five of said-CH$_2$-groups may optionally be substituted by one or more groups selected from —O—, —S—, =N(H)—, —C(=O)—, —C(O)NH— and —NHC(O)—;
or S$_1$ represents a spacer selected from:
—(CH$_2$)$_a$— wherein one of said —CH$_2$— groups may optionally be substituted by one or more groups selected from —C(=O)—; or
—(CH$_2$)$_b$—(CH$_2$—CH$_2$—O)$_c$—(CH$_2$)$_d$—, wherein four of said —CH$_2$— groups may optionally be substituted by one or more groups selected from —O—, —C(=O)— and —NHC(O)—.

3. The compound as defined in claim 2, wherein S$_1$ represents a spacer selected from:

—(CH$_2$)$_8$—CO—);

—(CH$_2$)$_2$—O—(CH$_2$)$_2$—NHCO—(CH$_2$CH$_2$O)$_4$—(CH$_2$)$_2$—NHCO—(CH$_2$)$_3$—CO—);

—(CH$_2$)$_8$—CO—); or

—(CH$_2$)$_2$—O—(CH$_2$)$_2$—NHCO—(CH$_2$CH$_2$O)$_4$—(CH$_2$)$_2$—NHCO—(CH$_2$)$_3$—CO—).

4. The compound as defined in claim 1, wherein a represents an integer selected from 1 to 30; or 5 to 25; or 8 to 20; or 9 to 15; or 9.

5. The compound as defined in claim 1, wherein b represents an integer selected from 0 to 8; or 2 to 6; or 6.

6. The compound as defined in claim 1, wherein c represents an integer selected from 1 to 10; or 1 to 5; or 4.

7. The compound as defined in claim 1, wherein d represents an integer selected from 1 to 15; or 1 to 10; or 2 to 8; or 7.

8. The compound as defined in claim 1, wherein z is selected from 1 to 40; or 1 to 36; or 4 to 30; or 4.3, 7.2, 8.3, 12 and 12-18.

9. The compound as defined in claim 1, wherein F represents rhamnose and has the following structure:

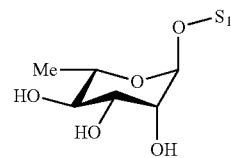

wherein S$_1$ refers to the point of attachment to the S$_1$ group.

10. The compound as defined in claim 1, wherein F represents a carbohydrate molecule that binds to a human anti-alpha-galactosyl antibody.

11. The compound as defined in claim 10, wherein F has a structure as shown in one of the following formulae:

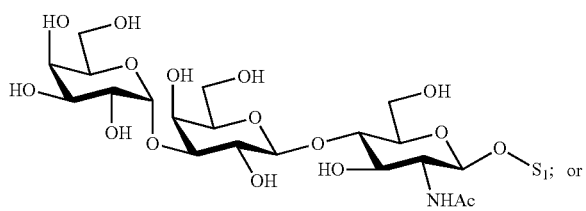

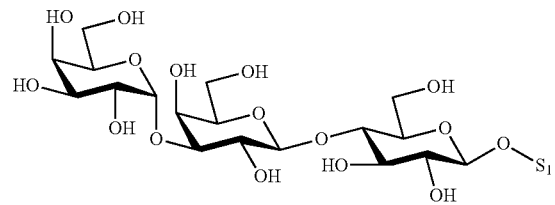

wherein S$_1$ refers to the point of attachment to the S$_1$ group.

12. The compound as defined in claim 11, wherein F has a structure as shown in the following formulae:

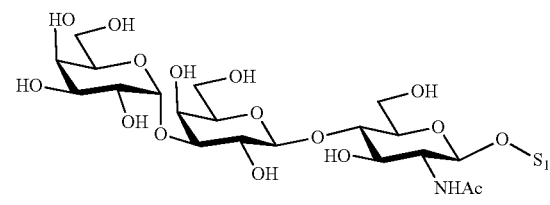

wherein S$_1$ refers to the point of attachment to the S$_1$ group.

13. The compound as defined in claim 1, wherein said antibody is a polyclonal antibody, a humanized antibody, a human antibody, a murine antibody, a chimeric antibody, or a single domain antibody (sdAb).

14. The compound as defined in claim 1, wherein said antigen binding fragment thereof is an antigen-binding fragment (Fab) or a single-chain variable fragment (scFv).

15. The compound as defined in claim 1, wherein said antigen binding fragment is selected from the group consisting of Fab, Fab', F(ab)2, F(ab')2, and scFv.

16. The compound as defined in claim 1, wherein said antibody or antigen binding fragment thereof is an EGFR antibody comprising the amino acid sequences of SEQ ID NOS: 1 and 2; CD20 antibody comprising the amino acid sequences of SEQ ID NOS: 3 and 4; or a HER2 antibody comprising the amino acid sequences of SEQ ID NOS: 5 and 6.

17. The compound as defined in claim 1, wherein said antibody or antigen binding fragment thereof is selected from a pathogen specific antibody or a fragment thereof.

18. A pharmaceutical composition comprising a compound as defined in claim 1 or a pharmaceutically acceptable salt thereof.

19. The pharmaceutical composition as defined in claim 18, which additionally comprises one or more further therapeutic agents.

20. A method of treating cancer or a bacterial infection comprising administering to an individual in need thereof a compound as defined in claim 1 or a pharmaceutically acceptable salt thereof.

21. A process for preparing a compound as defined in claim 1 which comprises:
(a) preparing a compound of formula (I) wherein X represents —NH— by reacting a compound of formula (IIA) wherein $S_1$ is terminated with a N-hydroxysuccinimide group with compounds of formula (IIIA) wherein the antibody or antigen binding fragment contains at least one reactive amino group:

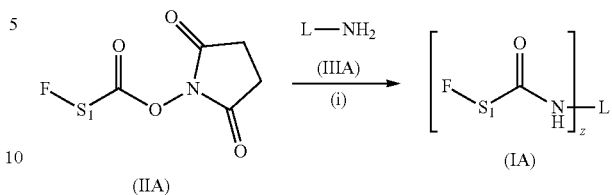

wherein F, $S_1$ and L are as defined in claim 1; or
(b) preparing a compound of formula (I) wherein X represents —S— by reacting a compound of formula (IIIB) wherein the antibody or antigen binding fragment contains at least one reactive thiol group with a compound of formula (IIB) wherein $S_1$ is terminated with maleimide:

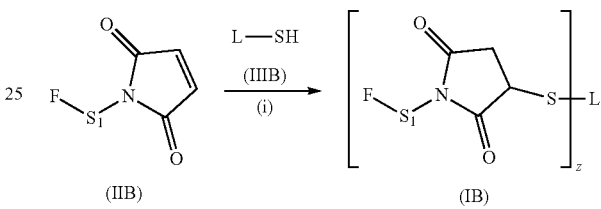

wherein F, $S_1$ and L are as defined in claim 1; and/or
(c) interconversion of a compound of formula (I) or protected derivative thereof to an alternative compound of formula (I) or protected derivative thereof.

* * * * *